(12) United States Patent
Hennequin et al.

(10) Patent No.: US 7,160,889 B2
(45) Date of Patent: Jan. 9, 2007

(54) QUINAZOLINE COMPOUNDS

(75) Inventors: Laurent Francois Andre Hennequin, Reims (FR); Elaine Sophie Elizabeth Stokes, Macclesfield (GB)

(73) Assignee: AstraZeneca AB, Sodertalje (SE)

( * ) Notice: Subject to any disclaimer, the term of this patent is extended or adjusted under 35 U.S.C. 154(b) by 346 days.

(21) Appl. No.: 10/240,658

(22) PCT Filed: Apr. 3, 2001

(86) PCT No.: PCT/GB01/01514

§ 371 (c)(1),
(2), (4) Date: Oct. 3, 2002

(87) PCT Pub. No.: WO01/77085

PCT Pub. Date: Oct. 18, 2001

(65) Prior Publication Data

US 2003/0191308 A1    Oct. 9, 2003

(30) Foreign Application Priority Data

| Apr. 7, 2000 | (EP) | ................... | 00400967 |
| Apr. 7, 2000 | (EP) | ................... | 00400968 |
| Apr. 13, 2000 | (EP) | ................... | 00401033 |
| Apr. 13, 2000 | (EP) | ................... | 00401034 |

(51) Int. Cl.
*C07D 239/00* (2006.01)
*C07D 239/70* (2006.01)
*A01N 47/40* (2006.01)

(52) U.S. Cl. ................... 514/258.1; 514/258; 544/242; 544/253

(58) Field of Classification Search ................ 544/242, 544/253; 514/258, 258.1
See application file for complete search history.

(56) References Cited

U.S. PATENT DOCUMENTS

| 3,266,990 A | 8/1966 | Lutz et al. |
| 3,376,195 A | 4/1968 | Allais et al. |
| 4,343,940 A | 8/1982 | Kreighbaum et al. |
| 4,421,920 A | 12/1983 | Baudouin et al. |
| 5,373,011 A | 12/1994 | Haley |
| 5,409,930 A | 4/1995 | Spada et al. |
| 5,411,963 A | 5/1995 | Dreikorn et al. |
| 5,457,105 A | 10/1995 | Barker |
| 5,475,001 A | 12/1995 | Barker |
| 5,480,883 A | 1/1996 | Spada et al. |
| 5,569,658 A | 10/1996 | Barker |
| 5,571,815 A | 11/1996 | Schaper et al. |
| 5,580,870 A | 12/1996 | Barker et al. |
| 5,616,582 A | 4/1997 | Barker |
| 5,646,153 A | 7/1997 | Spada et al. |
| 5,650,415 A | 7/1997 | Tang et al. |
| 5,656,643 A | 8/1997 | Spada et al. |
| 5,710,158 A | 1/1998 | Myers et al. |
| 5,712,395 A | 1/1998 | App et al. |
| 5,714,493 A | 2/1998 | Myers et al. |
| 5,721,237 A | 2/1998 | Myers et al. |
| 5,736,534 A | 4/1998 | Arnold |
| 5,747,498 A | 5/1998 | Schnur et al. |
| 5,770,599 A | 6/1998 | Gibson |
| 5,770,603 A | 6/1998 | Gibson |
| 5,792,771 A | 8/1998 | App et al. |
| 5,814,630 A | 9/1998 | Barker et al. |
| 5,821,246 A | 10/1998 | Brown et al. |
| 5,866,572 A | 2/1999 | Barker et al. |
| 5,929,080 A | 7/1999 | Frost |
| 5,932,574 A | 8/1999 | Barker |
| 5,942,514 A | 8/1999 | Barker |
| 5,952,333 A | 9/1999 | Barker |
| 5,955,464 A | 9/1999 | Barker |
| 5,962,458 A | 10/1999 | Lohmann et al. |

(Continued)

FOREIGN PATENT DOCUMENTS

DE    02213558    10/1972

(Continued)

OTHER PUBLICATIONS

Hennequin et al., "Design and Structure . . . ", J. Med. Chem 1999, 42, 5369-5389.*

(Continued)

*Primary Examiner*—James O. Wilson
*Assistant Examiner*—Paul V. Ward
(74) *Attorney, Agent, or Firm*—Morgan Lewis & Bockius LLP

(57) ABSTRACT

The invention concerns quinazoline derivatives of Formula (I)

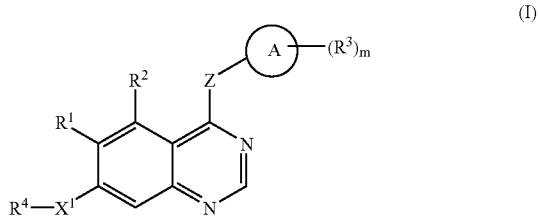

wherein ring A is phenyl or a 5-or 6-membered heterocyclic ring which may be saturated, partially saturated or unsaturated and may be aromatic or non-aromatic and which contains 1, 2 or 3 ring heteroatoms selected from O, N and S; Z is —O—, —NH— or —S—; and $X^1$, $R^1$, $R^2$, $R^3$, m and $R^4$ have any of the meanings defined in the description; processes for their preparation, pharmaceutical compositions containing them and their use in producing an antiangiogenic and/or vascular permeability reducing effect in warm-blooded animals, and in the treatment of disease states such as cancer, rheumatoid arthritis and psorlasis.

14 Claims, No Drawings

U.S. PATENT DOCUMENTS

| | | | |
|---|---|---|---|
| 6,002,008 | A | 12/1999 | Wissner et al. |
| 6,015,814 | A | 1/2000 | Barker |
| 6,057,320 | A | 5/2000 | Spada et al. |
| 6,071,921 | A | 6/2000 | Lohmann et al. |
| 6,184,225 | B1 | 2/2001 | Thomas et al. |
| 6,258,951 | B1 | 7/2001 | Lohmann et al. ............ 544/283 |
| 6,265,411 | B1 | 7/2001 | Thomas et al. .......... 514/266.2 |
| 6,291,455 | B1 | 9/2001 | Thomas et al. .......... 514/231.5 |
| 6,294,532 | B1 | 9/2001 | Thomas et al. .......... 514/228.2 |
| 6,362,336 | B1 | 3/2002 | Lohmann et al. ........... 544/283 |
| 6,414,148 | B1 | 7/2002 | Thomas et al. ............. 544/283 |
| 6,514,971 | B1 | 2/2003 | Thomas et al. .......... 514/234.5 |
| 6,673,803 | B1 | 1/2004 | Thomas et al. .......... 514/263.4 |
| 6,809,097 | B1 | 10/2004 | Thomas et al. .......... 514/235.2 |
| 6,887,874 | B1 | 5/2005 | Hennequin .................. 514/248 |
| 6,897,210 | B1 | 5/2005 | Thomas et al. ............. 514/183 |
| 2003/0144298 | A1 | 7/2003 | Curwen et al. ........ 514/252.17 |
| 2003/0199491 | A1 | 10/2003 | Hennequin ............. 514/210.21 |
| 2003/0199513 | A1 | 10/2003 | Thomas et al. ............. 514/248 |
| 2003/0207878 | A1 | 11/2003 | Hennequin ............. 514/228.2 |
| 2003/0225111 | A1 | 12/2003 | Hennequin et al. ....... 514/260.1 |
| 2005/0043395 | A1 | 2/2005 | Wedge ........................ 514/449 |
| 2005/0085465 | A1 | 4/2005 | Hennequin ............... 514/227.8 |
| 2005/0222183 | A1 | 10/2005 | Wedge .................. 514/266.22 |
| 2005/0239777 | A1 | 10/2005 | Thomas et al. .......... 514/227.8 |

FOREIGN PATENT DOCUMENTS

| | | |
|---|---|---|
| DE | 19614718 | 10/1997 |
| DE | 199 11 509 A | 9/2000 |
| DE | 19911509 | 9/2000 |
| EP | 0 326 307 A2 | 8/1989 |
| EP | 0 326 330 A2 | 8/1989 |
| EP | 0 520 722 A1 | 12/1992 |
| EP | 0 566 226 A | 10/1993 |
| EP | 0 602 851 A1 | 6/1994 |
| EP | 0 635 498 A1 | 1/1995 |
| EP | 0 635 507 A1 | 1/1995 |
| EP | 0 743 308 | 11/1996 |
| EP | 0 787 722 A1 | 8/1997 |
| EP | 0 837 063 A1 | 4/1998 |
| FR | 2077455 | 9/1969 |
| GB | 2 033 894 A | 5/1980 |
| GB | 2 160 201 A | 12/1985 |
| JP | 54-2327 | 9/1979 |
| WO | WO 87/04321 | 7/1987 |
| WO | WO 92/14716 | 9/1992 |
| WO | WO 92/16527 | 10/1992 |
| WO | WO 92/20642 | 11/1992 |
| WO | WO 93/03030 | 2/1993 |
| WO | WO 93/13097 | 7/1993 |
| WO | WO 95/15758 | 6/1995 |
| WO | WO 95/19169 | 7/1995 |
| WO | WO 95/21613 | 8/1995 |
| WO | WO 95/23141 | 8/1995 |
| WO | WO 95/24190 | 9/1995 |
| WO | WO 96/09294 | 3/1996 |
| WO | WO 96/15118 | 5/1996 |
| WO | WO 96/16960 | 6/1996 |
| WO | WO 96/29331 | 9/1996 |
| WO | WO 96/30347 | 10/1996 |
| WO | WO 96/30370 | 10/1996 |
| WO | WO 96/33977 | 10/1996 |
| WO | WO 96/33978 | 10/1996 |
| WO | WO 96/33979 | 10/1996 |
| WO | WO 96/33980 | 10/1996 |
| WO | WO 96/33981 | 10/1996 |
| WO | WO 96/39145 | 12/1996 |
| WO | WO 96/40648 | 12/1996 |
| WO | WO 96/40673 | 12/1996 |
| WO | WO 97/02266 | 1/1997 |
| WO | WO 97/03069 | 1/1997 |
| WO | WO 97/17329 | 5/1997 |
| WO | 97/22596 A | 6/1997 |
| WO | WO 97/22596 | 6/1997 |
| WO | 97/30035 A | 8/1997 |
| WO | WO 97/28161 | 8/1997 |
| WO | WO 97/30034 | 8/1997 |
| WO | WO 97/30035 * | 8/1997 |
| WO | WO 97/30044 | 8/1997 |
| WO | 97/32856 A | 9/1997 |
| WO | WO 97/32856 * | 9/1997 |
| WO | WO 97/34876 | 9/1997 |
| WO | 97/38983 A | 10/1997 |
| WO | WO 97/37999 | 10/1997 |
| WO | WO 97/38983 | 10/1997 |
| WO | WO 97/38994 | 10/1997 |
| WO | WO 97/42187 | 11/1997 |
| WO | WO 97/49689 | 12/1997 |
| WO | WO 98/02434 | 1/1998 |
| WO | WO 98/10767 | 3/1998 |
| WO | 98/13354 A | 4/1998 |
| WO | WO 98/13350 | 4/1998 |
| WO | WO 98/13354 | 4/1998 |
| WO | WO 98/14431 | 4/1998 |
| WO | WO 98/23613 | 6/1998 |
| WO | WO 98/35958 | 8/1998 |
| WO | WO 98/43960 | 10/1998 |
| WO | WO 98/50038 | 11/1998 |
| WO | WO 99/06378 | 2/1999 |
| WO | WO 99/06396 | 2/1999 |
| WO | WO 99/09016 | 2/1999 |
| WO | WO 99/09024 | 2/1999 |
| WO | WO 99/10349 | 3/1999 |
| WO | WO 00/12497 | 3/2000 |
| WO | WO 00/21955 | 4/2000 |
| WO | WO 00/47212 | 8/2000 |
| WO | WO 01/32651 | 5/2001 |
| WO | WO 01/66099 | 9/2001 |
| WO | WO 01/74360 | 10/2001 |
| WO | WO 02/12226 | 2/2002 |
| WO | WO 02/12227 | 2/2002 |
| WO | WO 02/12228 | 2/2002 |
| WO | WO 03/039551 | 5/2003 |
| WO | WO 03/064413 | 8/2003 |
| WO | WO 04/014383 | 2/2004 |
| WO | WO 04/014426 | 2/2004 |
| WO | WO 04/032937 | 4/2004 |
| WO | WO 04/071397 | 8/2004 |

OTHER PUBLICATIONS

US RE36265, 08/1999, Spada et al. (withdrawn).
Arya et al., Nitroimidazoles: Part XVI—Some 1-Methyl-4-nitro-5-substituted Imidazoles, Indian Journal of Chemistry, vol. 21B, Dec. 1982, pp. 1115-1117.
Bridges, "The current status of tyrosine kinase inhibitors . . . ," Exp.Opin.Ther.Patents (1995), 5(12): 1245-1257, Editorial, Oncologic, Endocrine & Metabolic, 1995 Ashley Publications Ltd ISSN 1354-3776.
Bridges, et al., "Enantioselective Inhibition of the Epidermal Growth Factor Receptor Tyrosine Kinase by 4-(a-Phenethylamino)quinazolines," Bioorganic & Medicinal Chemistry, vol. 3, No. 12, pp. 1651-1656, 1995.
Connolly, et al., "Human Vascular Permeability Factor," J.Bio. Chem., vol. 264, No. 33, Nov. 1989, pp. 20017-20024.
Cullinan-Bove, et al., "Vascular Endothelial Growth Factor/Vascular Permeability Factor Expression in the Rat Uterus . . . ," Endocrinology, vol. 133, No. 2, 1993, pp. 829-837.
Fan, et al., "Controlling the Vasculature: Angiogenesis, Anti-Angiogenesis . . . ," TiPS Review, vol. 16, Feb. 1995, pp. 57-65.
Folkman, "Angiogenesis in Cancer, Vascular, Rheumatoid and Other Disease," Nature Medicine, vol. 1, No. 1, 1995, pp. 27-30.

Fry et al., "A Specific Inhibitor of the Epidermal Growth Factor Receptor Tyrosine Kinase," SCIENCE, vol. 265, Aug. 19, 1994, pp. 1093-1095.

Gazit et al., Tyrophostins IV-Highly Potent Inhibitors . . . Relationship Study of 4-Anilidoquinazolines, Bioorganic & Medicinal Chemistry, vol. 4. No. 8, 1996, pp. 1203-1207.

Golovkin et al., Nauchin TR-VSES-NAUCHNO-ISSLED INST FARM, 1990, 28, 70-75.

Hara et al., On the Amination of Azaheterocycles. A New Procedure for the Introduction of an Amino Group (1), J. Heterocyclic Chem. vol. 19, 1982, pp. 1285-1287.

Higashino, Chem. Pharm. Bull., 1985, 33, 3, 950-961.

Iyer, et al., "Studies in Potential Amoebicides: Part III-Synthesis of 4-Substituted Amino-8-Hydroxy) Quinazolines & 3-Substituted 8-Hydroxy(&8-Methoxy)-4-Quinazolones," J.Sci.Industr.Res., vol. 15C, Jan. 1956, pp. 1-7.

Jakeman, et al., "Developmental Expression of Binding Sites and Messenger Ribonucleic Acid . . . ," Endocrinology, vol. 133, No. 2, 1993, pp. 848-859.

Karminski et al., The Synthesis of Some Quinazoline Derivatives and Their Biological Properties; J. Environ. Sci. Health, vol. B18, 1983, pp. 599-610.

Klohs WD et al., "Antiangiogenic agents" Curr Opin Biotechnol. vol. 10 No. 6, 1999, pp. 544-549.

Kim, et al., "Inhibition of Vascular Endothelial Growth Factor-Induced Angiogenesis Suppresses Tumour Growth in Vivo," Nature, vol. 362, Apr. 1993, pp. 841-844.

Kobayashi, Derwent Abstract 82-87077, vol. 6, No. 244, Dec. 1982, JP 57-144266, Sep. 1982, "4-Anilinoquinazoline Derivative, its Preparation and Analgesic and Antiphlogistic Agent Containing Said Derivative as Active Component". (n.7).

Kolch, et al., "Regulation of the Expression of the VEGF/VPS and its Receptors: Role in Tumor Angiogenesis," Breast Cancer Research and Treatment, vol. 36, 1995, pp. 139-155.

Kumar et al., Reactions of Diazines with Nucleophiles-IV.1 The Reactivity . . . Single Electron Transfer Reactions, Bioorganic & Medicinal Chemistry, vol. 3, No. 7, 1995, pp. 891-897.

Kyorin, Derwent Abstract 84-53835, JP 59-13765, Jan. 1984, "2-(4-Quinazolinyl)amino benzoic acid derivs . . . having analgesic and antiinflammatory activities". (n.8).

Li, et al., Chem.Abs., vol. 92:76445u, 1980, p. 674-675.

Lin et al., Chem.Abs., vol. 96:122728w, 1982, p. 695.

Nagarajan et al., Nitroimidazoles: Part XIX†-Structure Activity Relationships‡, Indian Journal of Chemistry, vol. 23B, Apr. 1984, pp. 342-362.

Nomoto et al., Studies on Cardiotonic Agents. VII.1)Potent Cardiotonic Agent KF15232 with Myofibrillar CA2+ Sensitizing Effect, Chem. Pharm. Bull., vol. 39(4), 1991, pp. 900-910.

Rewcastle et al., "Tyrosine Kinase Inhibitors. 5 . . . 4-(Phenylamino)quinazolines as Potent . . . Inhibitors of the Tyrosine Kinase Domain of the Epidermal Growth Factor Receptor," J.Med.Chem. 1995, vol. 38, pp. 3482-3487.

Sankyo and Ube, Derwent Abstract 81-28290, JP 56-20577, Feb. 1981, "4-(N-alkyl:anilino) quinazoline derivs . . . having analgesic antiinflammatory actions". (n.9)

Schonowsky et al., Chinazolinderivate, ihre Herstellung und biologische Wirkung, Quinzaolines, their Preparation and Biological Activity, Z. Naturforsch, 37b, 1982, pp. 907-911.

Senger, et al., "Vascular Permeability Factor (VPF, VEGF) in Tumor Biology," Cancer and Metastasis Reviews, vol. 12, 1993, pp. 303-324.

Sinyak, et al., Synthesis and Biological Properties of Derivatives of 4-Heterylmercaptoquinazoline, Zaporozh'e Medical Institute pp. 103-106, translated from Khimiko-farmatsevticheskii Zhurnal, vol. 20, No. 2, Feb. 1986, 168-171, original article submitted Dec. 29, 1984.

Spada, et al., Small molecule inhibitors of tyrosine Kinase activity, Exp.Opin.Ther.Patents (1995), 5(8):805-817, Patent Update, Oncologic, Endocrine & Metabolic, Ashley Publications Ltd ISSN 1354-3776.

Stets et al., Investigation of Anti-Arrhythmic Action of Quinazopyrine, Pharmacology Dept., Zaporozhye Medical Institute, Zaporozhye, and Vinnitsa Medical Institute, Vinnitsa, pp. 94-96, translated from Farmakol. 1 toksik., vol. 53, No. 3, 1990, pp. 15-17.

Traxler, et al., "Recent advances in protein tyrosine kinase inhibitors," Drugs of the Future 1995, vol. 20(12, pp. 1261-1274.

Vinogradoff et a;/, Development of a New Synthesis of . . . Sodium Salt via an Amidine Intermediate, J. Heterocyclic Chem. vol. 26, 97, Jan.-Feb. 1989, pp. 97-103.

Ward, et al., "Epidermal Growth Factor Receptor Tyrosine Kinase—Investigation of Catalytic Mechanism, Structure-Based Searching and Discovery of a Potent Inhibitor," Biochem.Pharmacology, vol. 48, No. 4, pp. 659-666 (1994).

Wolfe et al., A Facile One-Step Synthesis of Certain 4-(4-Pyrimidinylmethyl)quinazolines, J. Heterocyclic Chem., vol. 13, 1976, pp. 383-385.

* cited by examiner

QUINAZOLINE COMPOUNDS

The present invention relates to quinazoline derivatives, processes for their preparation, pharmaceutical compositions containing them as active ingredient, methods for the treatment of disease states associated with angiogenesis and/or increased vascular permeability, to their use as medicaments and to their use in the manufacture of medicaments for use in the production of antiangiogenic and/or vascular permeability reducing effects in warm-blooded animals such as humans.

Normal angiogenesis plays an important role in a variety of processes including embryonic development, wound healing and several components of female reproductive function. Undesirable or pathological angiogenesis has been associated with disease states including diabetic retinopathy, psoriasis, cancer, rheumatoid arthritis, atheroma, Kaposi's sarcoma and haemangioma (Fan et al, 1995, Trends Pharmacol. Sci. 16: 57–66; Folkman, 1995, Nature Medicine 1: 27–31). Alteration of vascular permeability is thought to play a role in both normal and pathological physiological processes (Cullinan-Bove et al, 1993, Endocrinology 133: 829–837; Senger et al, 1993, Cancer and Metastasis Reviews, 12: 303–324). Several polypeptides with in vitro endothelial cell growth promoting activity have been identified including, acidic and basic fibroblast growth factors (aFGF & bFGF) and vascular endothelial growth factor (VEGF). By virtue of the restricted expression of its receptors, the growth factor activity of VEGF, in contrast to that of the FGFs, is relatively specific towards endothelial cells. Recent evidence indicates that VEGF is an important stimulator of both normal and pathological angiogenesis (Jakeman et al, 1993, Endocrinology, 133: 848–859; Kolch et al, 1995, Breast Cancer Research and Treatment, 36:139–155) and vascular permeability (Connolly et al, 1989, J. Biol. Chem. 264: 20017–20024). Antagonism of VEGF action by sequestration of VEGF with antibody can result in inhibition of tumour growth (Kim et al, 1993, Nature 362: 841–844).

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine linase domain. Binding of ligand to the receptor results in stimulation of the receptor-associated tyrosine kinase activity which leads to phosphorylation of tyrosine residues on both the receptor and other intracellular molecules. These changes in tyrosine phosphorylation initiate a signalling cascade leading to a variety of cellular responses. To date, at least nineteen distinct RTK subfamilies, defined by amino acid sequence homology, have been identified. One of these subfamilies is presently comprised by the fms-like tyrosine kinase receptor, Flt or Flt1, the kinase insert domain-containing receptor, KDR (also referred to as Flk-1), and another fms-like tyrosine kinase receptor, Flt4. Two of these related RTKs, Flt and KDR, have been shown to bind VEGF with high affinity (De Vries et al, 1992, Science 255: 989–991; Terman et al, 1992, Biochem. Biophys. Res. Comm. 1992, 187: 1579–1586). Binding of VEGF to these receptors expressed in heterologous cells has been associated with changes in the tyrosine phosphorylation status of cellular proteins and calcium fluxes.

Compounds of the present invention inhibit the effects of VEGF, a property of value in the treatment of disease states associated with angiogenesis and/or increased vascular permeability such as cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation.

Compounds of the present invention possess higher potency against VEGF receptor tyrosine kinase whilst possessing some activity against EGF receptor tyrosine kinase. Furthermore, compounds of the present invention, possess substantially higher potency against VEGF receptor tyrosine kinase than against EGF receptor tyrosine kinase or FGF $R^1$ receptor tyrosine kinase.

According to the present invention there is provided a quinazoline derivative of the formula I:

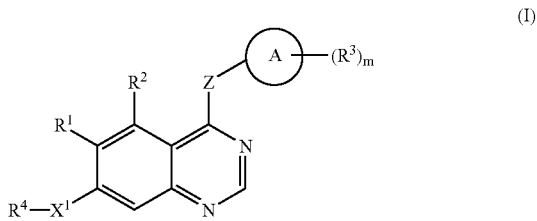

[wherein:
ring A is phenyl or a 5-or 6-membered heterocyclic ring which may be saturated, partially saturated or unsaturated and may be aromatic or non-aromatic and which contains 1, 2 or 3 ring heteroatoms selected from O, N and S;
Z is —O—, —NH— or —S—;
m is an integer from 0 to 5 inclusive;
$R^1$ is hydrogen, hydroxy, halogeno, nitro, trifluoromethyl, cyano, $C_{1-3}$alkyl, $C_{1-3}$alkoxy, $C_{1-3}$alkylthio, or —$NR^5R^6$ (wherein $R^5$ and $R^6$, which may be the same or different, are hydrogen or $C_{1-3}$alkyl);
$R^2$ is hydrogen, hydroxy, halogeno, $C_{1-3}$alkyl, $C_{1-3}$alkoxy, trifluoromethyl, amino or nitro;
$R^3$ is hydroxy, halogeno, $C_{1-3}$alkyl, $C_{1-3}$alkoxy, $C_{1-3}$alkanoyloxy, trifluoromethyl, cyano, amino or nitro; provided that when ring A is a 5- or 6-membered heterocyclic ring, at least one $R^3$ is either hydroxy or halogeno;
$X^1$ is —O—, —$CH_2$—, —S—, —SO—, —$SO_2$—, —$NR^7$—, —$NR^7CO$—, —$CONR^7$—, —$SO_2NR^7$— or —$NR^7SO_2$—, (wherein $R^7$ is hydrogen, $C_{1-3}$alkyl or $C_{1-3}$alkoxy$C_{2-3}$alkyl);
$R^4$ is selected from one of the following groups:
1) —$Y^1X^2COR^8$ [wherein —$Y^1$— is a $C_{2-5}$alkylene chain wherein each methylene group (other than that of the α-carbon) is optionally substituted by 1 substituent independently selected from hydroxy, halogeno, amino and $C_{1-4}$alkanoyloxy, provided that there is at least 1 and no more than 3 substituents on the $C_{2-5}$alkylene chain; $X^2$ is —O— or —$NR^9$— (in which $R^9$ is hydrogen, $C_{1-3}$alkyl or $C_{1-3}$alkoxy$C_{2-3}$alkyl) and $R^8$ is $C_{1-3}$alkyl, —$NR^{10}R^{11}$ or —$OR^{12}$ (wherein $R^{10}$, $R^{11}$ and $R^{12}$, which may be the same or different, are hydrogen, $C_{1-3}$alkyl or $C_{1-3}$alkoxy$C_{2-3}$alkyl)];
2) —$Y^2$—$X^3R^{13}$ [wherein —$Y^2$— is $C_{2-5}$alkylene, $C_{3-5}$alkenylene or $C_{3-5}$alkynylene wherein each methylene group (other than that of the α-carbon) is optionally substituted by 1 substituent independently selected from hydroxy, halogeno, amino and $C_{1-4}$alkanoyloxy, provided that there is at least 1 substituent and no more than 3 substituents on the alkylene, alkenylene or alkynylene chain; $X^3$ is —O—, —S—, —SO—, —SO$_2$—, —OCO—, —NR$^7$CO—, —CONR$^7$—, —SO$_2$NR$^7$—, —NR$^7$SO$_2$— or —NR$^7$— (wherein $R^7$ is as hereinabove defined) and $R^{13}$ is hydrogen or $C_{1-3}$alkyl, wherein the $C_{1-3}$alkyl group may bear one or two substituents selected from oxo, hydroxy, halogeno and $C_{1-4}$alkoxy;

3) —Y$^1$—X$^6$C$_{1-5}$alkylR$^{14}$ [wherein Y$^1$ is as hereinabove defined and $X^6$ is —O—, —S—, —SO—, —SO$_2$—, —NR$^7$CO—, —CONR$^7$—, —SO$_2$NR$^7$—, —NR$^7$SO$_2$— or —NR$^7$— (wherein $R^7$ is as hereinabove defined) and $R^{14}$ is $C_{1-7}$cycloalkyl or a 3 to 7 membered saturated or partially saturated heterocyclic group containing up to 3 ring heteroatoms selected independently from O, S and N, wherein the carbocyclic or heterocyclic group is optionally substituted by one or two substituents selected from oxo, hydroxy, halogeno, $C_{1-4}$alkyl, (wherein the $C_{1-4}$alkyl group is optionally substituted by 1 or 2 substituents selected from hydroxy, cyano, halogeno, amino, nitro, morpholino, $C_{3-5}$cycloalkyl, piperidin-1-yl and piperazin-1-yl), $C_{2-4}$alkenyl, $C_{2-4}$alkynyl, $C_{1-4}$hydroxyalkyl, $C_{1-4}$alkoxy, carbamoyl, $C_{1-3}$alkylcarbamoyl, N,N-di($C_{1-3}$alkyl)carbamoyl, $C_{1-4}$alkanoyl, $C_{1-4}$alkoxycarbonyl, $C_{1-4}$alkylthio, $C_{1-4}$alkylsulphinyl, $C_{1-4}$alkylsulphonyl, $C_{2-4}$alkanoylamino, N—$C_{1-3}$alkyl-$C_{2-4}$alkanoylamino, N—$C_{1-3}$alkylsulphamoyl, N,N-di-[$C_{1-3}$alkyl]sulphamoyl, $C_{1-3}$alkanesulphonylamino and N—$C_{1-3}$alkyl-$C_{1-3}$alkanesulphonylamino, or $R^{14}$ is a pyridone group, a phenyl group or a 5 or 6-membered aromatic heterocyclic group containing 1 to 3 ring heteroatoms independently selected from O, N and S, and wherein the pyridone, phenyl or heterocyclic group is optionally substituted by up to 5 substituents selected from halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, $C_{1-4}$alkylthio, $C_{1-4}$alkylsulphinyl, $C_{1-4}$alkylsulphonyl, N—$C_{1-3}$alkylsulphamoyl N,N-di-[$C_{1-3}$alkyl]sulphamoyl, $C_{1-3}$alkanesulphonylamino, N—$C_{1-3}$alkyl-$C_{1-3}$alkanesulphonylamino, —CONR$^{10}$R$^{11}$ and —NR$^{10}$COR$^{11}$ (wherein $R^{10}$ and $R^{11}$ are as hereinabove defined)];

4) —Y$^1$—X$^4$C$_{1-5}$alkylX$^5$R$^{15}$ [wherein Y$^1$ is as hereinabove defined and $X^4$ and) which may be the same or different are each —O—, —S—, —SO—, —SO$_2$—, —NR$^7$CO—, —CONR$^7$—, —SO$_2$NR$^7$—, —NR$^7$SO$_2$— or —NR$^7$— (wherein $R^7$, is as hereinabove defined and $R^{15}$ is hydrogen or $C_{1-3}$alkyl)];

5) —Y$^1$—O—C$_{1-3}$alkyl (wherein Y$^1$ is as hereinabove defined) provided that $X^1$ is —O—, —S—, —SO—or —SO$_2$—;

6) —Y$^2$—R$^{16}$ {wherein —Y$^2$— is as hereinabove defined and $R^{16}$ is a saturated or partially saturated 3 to 7 membered heterocyclic ring, containing up to 3 heteroatoms selected from O, S and N [wherein the heterocyclic ring is optionally substituted by up to 3 substituents selected from oxo, hydroxy, halogeno, $C_{1-4}$alkyl, $C_{2-4}$alkenyl, $C_{2-4}$alkynyl and $C_{3-7}$cycloalkyl (wherein $C_{1-4}$alkyl, $C_{2-4}$alkenyl, $C_{2-4}$alkynyl and $C_{3-7}$cycloalkyl are themselves optionally substituted by up to 3 substituents selected from hydroxy, halogeno, cyano, $C_{1-3}$alkyl, $C_{1-3}$alkoxy, $C_{1-3}$alkanoyloxy, trifluoromethyl, amino, nitro and $R^{14}$ as hereinabove defined), $C_{1-4}$alkoxy, carbamoyl, $C_{1-4}$alkylcarbamoyl, N—N-di($C_{1-4}$alkyl)carbamoyl, $C_{2-4}$alkanoyl, $C_{1-4}$alkoxycarbonyl, $C_{3-7}$cycloalkyl, $C_{1-4}$alkylthio, $C_{1-4}$alkylsulphinyl, $C_{1-4}$alkylsulphonyl, $C_{2-4}$alkanoylamino, N—$C_{1-3}$alkyl-$C_{2-4}$alkanoylamino, N—$C_{1-3}$alkylsulphamoyl, N,N-di-[$C_{1-3}$alkyl]sulphamoyl, $C_{1-3}$alkanesulphonylamino and N—$C_{1-3}$alkyl-$C_{1-3}$alkanesulphonylamino or $R^{16}$ is a pyridone group, a phenyl group or a 5 or 6-membered aromatic heterocyclic group containing 1 to 3 ring heteroatoms independently selected from O, N and S, and wherein the pyridone, phenyl or heterocyclic group is optionally substituted by up to 5 substituents selected from halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, $C_{1-4}$alkylthio, $C_{1-4}$alkylsulphinyl, $C_{1-4}$alkylsulphonyl, N—$C_{1-3}$alkylsulphamoyl, N,N-di-[$C_{1-3}$alkyl]sulphamoyl $C_{1-3}$alkanesulphonylamino, N—$C_{1-3}$alkyl-$C_{1-3}$alkanesulphonylamino, —CONR$^{10}$R$^{11}$ and —NR$^{10}$COR$^{11}$ (wherein $R^{10}$ and $R^{11}$ are as hereinabove defined)];

7) —Y$^2$X$^6$—R$^{14}$ (wherein Y$^2$, $X^6$ and $R^{14}$ are as hereinabove defined); and 8) —Y$^2$—NR$^{17}$R$^{18}$ [wherein Y$^2$ is as hereinabove defined and $R^{17}$ and $R^{18}$ are independently selected from hydrogen, $C_{1-6}$alkyl, $C_{2-16}$alkenyl, $C_{2-6}$alkynyl or $C_{1-3}$alkoxyC$_{1-6}$alkyl (wherein any alkyl group in $R^{17}$ or $R^{18}$ is optionally substituted by up to 2 substituents selected from hydroxy, halogeno, $C_{1-3}$alkyl, $C_{1-3}$alkoxy, $C_{1-3}$alkanoyloxy, trifluoromethyl, cyano, amino or nitro)];

9) —Y$^3$—R$^a$ (wherein Y$^3$ is $C_{1-5}$alkylene, $C_{2-5}$alkenylene or $C_{2-5}$alkynylene wherein each methylene group (other than that of the α-carbon) is optionally substituted by 1 substituent independently selected from hydroxy, halogeno, amino and $C_{1-4}$alkanoyloxy, provided that there are no more than 3 substituents on the alkylene, alkenylene or alkynylene chain; and $R^a$ is $C_{3-7}$cycloalkyl which is substituted by 1 substituent selected from hydroxy, amino and halogeno on the ring carbon linked to $Y^3$ and additionally optionally substituted by up to 3 substituents selected from oxo, hydroxy, halogeno, $C_{1-4}$alkyl, $C_{2-4}$alkenyl, $C_{2-4}$alkynyl, $C_{1-4}$alkoxy, carbamoyl, $C_{1-4}$alkylcarbamoyl, N—N-di($C_{1-4}$alkyl)carbamoyl, $C_{2-4}$alkanoyl, $C_{1-4}$alkoxycarbonyl and $C_{3-7}$cycloalkyl (wherein $C_{1-4}$alkyl, $C_{2-4}$alkenyl, $C_{2-4}$alkynyl and $C_{3-7}$cycloalkyl are themselves optionally substituted by up to 3 substitutents selected from hydroxy, halogeno, cyano, $C_{1-3}$alkyl, $C_{1-3}$alkoxy, $C_{1-3}$alkanoyloxy, trifluoromethyl, cyano, amino, nitro and $R^{14}$ as hereinabove defined)];

provided that when:

m is an integer from 1 to 3;

$R^1$ is methoxy; $R^2$ is hydrogen; Z is —NH—;

$R^3$ is halogeno or $C_{1-3}$alkyl; and $X^1$ is —O—; then $R^4$ is not selected from one of the following three groups:

a) —C$_{2-5}$alkylR$^{19}$ (wherein $R^{19}$ is piperidin-4-yl which may bear one or two substituents selected from hydroxy, halogeno, $C_{1-4}$alkyl, $C_{1-4}$hydroxyalkyl and $C_{1-4}$alkoxy);

b) —C$_{2-5}$alkenylR$^{19}$ (wherein $R^{19}$ is as defined hereinbefore);

c) —C$_{2-5}$alkynylR$^{19}$ (wherein $R^{19}$ is as defined hereinbefore);

wherein any alkylene, alkenylene or alkynylene chain in groups a) to c) above are optionally substituted by one or more substituents selected from hydroxy, halogeno and amino; or a pharmaceutically-acceptable salt or prodrug thereof.

According to another aspect of the present invention there is provided a quinazoline derivative of the formula I:

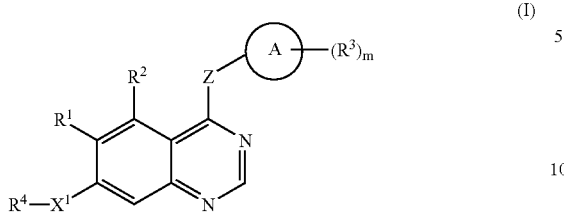

(I)

[wherein:
ring A is phenyl or a 5-or 6-membered heterocyclic ring which may be saturated, partially saturated or unsaturated and may be aromatic or non-aromatic and which contains 1, 2 or 3 ring heteroatoms selected from O, N and S;
Z is —O—, —NH— or —S—;
m is an integer from 0 to 5 inclusive;
$R^1$ is hydrogen, hydroxy, halogeno, nitro, trifluoromethyl, cyano, $C_{1-3}$alkyl, $C_{1-3}$alkoxy, $C_{1-3}$alkylthio, or —$NR^5R^6$ (wherein $R^5$ and $R^6$, which may be the same or different, are hydrogen or $C_{1-3}$alkyl);
$R^2$ is hydrogen, hydroxy, halogeno, $C_{1-3}$alkyl, $C_{1-3}$alkoxy, trifluoromethyl, amino or nitro;
$R^3$ is hydroxy, halogeno, $C_{1-3}$alkyl, $C_{1-3}$alkoxy, $C_{1-3}$alkanoyloxy, trifluoromethyl, cyano, amino or nitro; provided that when ring A is a 5- or 6-membered heterocyclic ring, at least one $R^3$ is either hydroxy or halogeno;
$X^1$ is —O—, —$CH_2$—, —S—, —SO—, —$SO_2$—, —$NR^7$—, —$NR^7CO$—, —$CONR^7$—, —$SO_2NR^7$— or —$NR^7SO_2$—, (wherein $R^7$ is hydrogen, $C_{1-3}$alkyl or $C_{1-3}$alkoxy$C_{2-3}$alkyl)
$R^4$ is selected from one of the following groups:
1) —$Y^1X^2COR^8$ [wherein —$Y^1$— is a $C_{2-5}$alkylene chain wherein each methylene group (other than that of the α-carbon) is optionally substituted by 1 substituent independently selected from hydroxy, halogeno and amino, provided that there is at least 1 and no more than 3 substituents on the $C_{2-5}$alkylene chain; $X^2$ is —O— or —$NR^9$— (in which $R^9$ is hydrogen, $C_{1-3}$alkyl or $C_{1-3}$alkoxy$C_{2-3}$alkyl) and $R^8$ is $C_{1-3}$alkyl, $NR^{10}R^{11}$ or —$OR^{12}$ (wherein $R^{10}$, $R^{11}$ and $R^{12}$, which may be the same or different, are hydrogen, $C_{1-3}$alkyl or $C_{1-3}$alkoxy$C_{2-3}$alkyl)];
2) —$Y^2$—$X^3R^{13}$ [wherein —$Y^2$— is $C_{2-5}$alkylene, $C_{3-5}$alkenylene or $C_{3-5}$alkynylene wherein each methylene group (other than that of the α-carbon) is optionally substituted by 1 substituent independently selected from hydroxy, halogeno and amino, provided that there is at least 1 substituent and no more than 3 substituents on the alkylene, alkenylene or alkynylene chain; $X^3$ is —O—, —S—, —SO—, —$SO_2$—, —OCO—, —$NR^7CO$—, —$CONR^7$—, —$SO_2NR^7$—, —$NR^7SO_2$— or —$NR^7$— (wherein $R^7$ is as hereinabove defined) and $R^{13}$ is hydrogen or $C_{1-3}$alkyl, wherein the $C_{1-3}$alkyl group may bear one or two substituents selected from oxo, hydroxy, halogeno and $C_{1-4}$alkoxy;
3) —Y—$X^6C_{1-5}$alkyl$R^{14}$ [wherein $Y^1$ is as hereinabove defined and $X^6$ is —O—, —S—, —SO—, —$SO_2$, —$NR^7CO$—, —$CONR^7$—, —$SO_2NR^7$—, —$NR^7SO_2$— or —$NR^7$— (wherein $R^7$ is as hereinabove defined) and $R^{14}$ is $C_{3-7}$cycloalkyl or a 3 to 7 membered saturated or partially saturated heterocyclic group containing up to 3 ring heteroatoms selected independently from O, S and N, wherein the carbocyclic or heterocyclic group is optionally substituted by one or two substituents selected from oxo, hydroxy, halogeno, $C_{1-4}$alkyl, (wherein the $C_{1-4}$alkyl group is optionally substituted by 1 or 2 substituents selected from hydroxy, cyano, halogeno, amino, nitro, morpholino, $C_{3-5}$cycloalkyl, piperidin-1-yl and piperazin-1-yl), $C_{2-4}$alkenyl, $C_{2-4}$alkynyl, $C_{1-4}$hydroxyalkyl, $C_{1-4}$alkoxy, carbamoyl, $C_{1-3}$alkylcarbamoyl, N,N-di($C_{1-3}$alkyl)carbamoyl, $C_{2-4}$alkanoyl, $C_{1-4}$alkoxycarbonyl, $C_{1-4}$alkylthio, $C_{1-4}$alkylsulphinyl, $C_{1-4}$alkylsulphonyl, $C_{2-4}$alkanoylamino, N—$C_{1-3}$alkyl-$C_{2-4}$alkanoylamino, N—$C_{1-3}$alkylsulphamoyl, N,N-di-[$C_{1-3}$alkyl]sulphamoyl, $C_{1-3}$alkanesulphonylamino and N—$C_{1-3}$alkyl-$C_{1-3}$alkanesulphonylamino,
or $R^{14}$ is a pyridone group, a phenyl group or a 5 or 6-membered aromatic heterocyclic group containing 1 to 3 ring heteroatoms independently selected from O, N and S, and wherein the pyridone, phenyl or heterocyclic group is optionally substituted by up to 5 substituents selected from halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, $C_{1-4}$alkylthio, $C_{1-4}$alkylsulphinyl, $C_{1-4}$alkylsulphonyl, N—$C_{1-3}$alkylsulphamoyl, N,N-di-[$C_{1-3}$alkyl]sulphamoyl, $C_{1-3}$alkanesulphonylamino, N—$C_{1-3}$alkyl-$C_{1-3}$alkanesulphonylamino, —$CONR^{10}R^{11}$ and —$NR^{10}COR^{11}$ (wherein $R^{10}$ and $R^{11}$ are as hereinabove defined)];
4) —$Y^1$—$X^4C_{1-5}$alkyl$X^5R^{15}$ [wherein $Y^1$ is as hereinabove defined and $X^4$ and $X^5$ which may be the same or different are each —O—, —S—, —SO—, —$SO_2$—, —$NR^7CO$—, —$CONR^7$—, —$SO_2NR^7$—, —$NR^7SO_2$— or —$NR^7$— (wherein $R^7$, is as hereinabove defined and $R^{15}$ is hydrogen or $C_{1-3}$alkyl)];
5) —$Y^1$—O—$C_{1-3}$alkyl (wherein $Y^1$ is as hereinabove defined) provided that $X^1$ is —O—, —S—, —SO— or —$SO_2$—;
6) —$Y^2$—$R^{16}$ {wherein —$Y^2$— is as hereinabove defined and $R^{16}$ is a saturated or partially saturated 3 to 7 membered heterocyclic ring containing up to 3 heteroatoms selected from O, S and N [wherein the heterocyclic ring is optionally substituted by up to 3 substitutents selected from oxo, hydroxy, halogeno, $C_{1-4}$alkyl, $C_{2-4}$alkenyl, $C_{2-4}$alkynyl and $C_{3-7}$cycloalkyl (wherein $C_{1-4}$alkyl, $C_{2-4}$alkenyl, $C_{2-4}$alkynyl and $C_{3-7}$cycloalkyl are themselves optionally substituted by up to 3 substitutents selected from hydroxy, halogeno, cyano, $C_{1-3}$alkyl, $C_{1-3}$alkoxy, $C_{1-3}$alkanoyloxy, trifluoromethyl, amino, nitro and $R^{14}$ as hereinabove defined), $C_{1-4}$alkoxy, carbamoyl, $C_{1-4}$alkylcarbamoyl, N—N-di($C_{1-4}$alkyl)carbamoyl, $C_{2-4}$alkanoyl, $C_{1-4}$alkoxycarbonyl, $C_{3-7}$cycloalkyl, $C_{1-4}$alkylthio, $C_{1-4}$alkylsulphinyl, $C_{1-4}$alkylsulphonyl, $C_{2-4}$alkanoylamino, N—$C_{1-3}$alkyl-$C_{2-4}$alkanoylamino, N—$C_{1-3}$alkylsulphamoyl, N,N-di-[$C_{1-3}$alkyl]sulphamoyl, $C_{1-3}$alkanesulphonylamino and N—$C_{1-3}$alkyl-$C_{1-3}$alkanesulphonylamino or $R^{16}$ is a pyridone group, a phenyl group or a 5 or 6-membered aromatic heterocyclic group containing 1 to 3 ring heteroatoms independently selected from O, N and S, and wherein the pyridone, phenyl or heterocyclic group is optionally substituted by up to 5 substituents selected from halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, $C_{1-4}$alkylthio, $C_{1-4}$alkylsulphinyl, $C_{1-4}$alkylsulphonyl, N—$C_{1-3}$alkylsulphamoyl, N,N-di-[$C_{1-3}$alkyl]sulphamoyl, $C_{1-3}$alkanesulphony-lamino, N—$C_{1-3}$alkyl-$C_{1-3}$alkanesulphonylamino, —$CONR^{10}R^{11}$ and —$NR^{10}COR^{11}$ (wherein $R^{10}$ and $R^{11}$ are as hereinabove defined)];

7) —Y$^1$—X$^6$—R$^{14}$ (wherein Y$^2$, X$^6$ and R$^{14}$ are as hereinabove defined); and
8) —Y$^2$—NR$^{17}$R$^{18}$ [wherein Y$^2$ is as hereinabove defined and R$^{17}$ and R$^{18}$ are independently selected from hydrogen, C$_{1-6}$alkyl, C$_{2-6}$alkenyl, C$_{2-6}$alkynyl or C$_{1-3}$alkoxyC$_{1-6}$alkyl (wherein any alkyl group in R$^{17}$ or R$^{18}$ is optionally substituted by up to 2 substituents selected from hydroxy, halogeno, C$_{1-3}$alkyl, C$_{1-3}$alkoxy, C$_{1-3}$alkanoyloxy, trifluoromethyl, cyano, amino or nitro)];
9) —Y$^3$—R$^a$ (wherein Y$^3$ is C$_{1-5}$alkylene, C$_{2-5}$alkenylene or C$_{2-5}$alkynylene wherein each methylene group (other than that of the α-carbon) is optionally substituted by 1 substituent independently selected from hydroxy, halogeno and amino, provided that there are no more than 3 substituents on the alkylene, alkenylene or alkynylene chain; and R$^a$ is C$_{3-7}$cycloalkyl which is substituted by 1 substituent selected from hydroxy, amino and halogeno on the ring carbon linked to Y$^3$ and additionally optionally substituted by up to 3 substituents selected from oxo, hydroxy, halogeno, C$_{1-4}$alkyl, C$_{2-4}$alkenyl, C$_{2-4}$alkynyl, C$_{1-4}$alkoxy, carbamoyl, C$_{1-4}$alkylcarbamoyl, N—N-di(C$_{1-4}$alkyl)carbamoyl, C$_{2-4}$alkanoyl, C$_{1-4}$alkoxycarbonyl and C$_{3-7}$cycloalkyl (wherein C$_{1-4}$alkyl, C$_{2-4}$alkenyl, C$_{2-4}$alkynyl and C$_{3-7}$cycloalkyl are themselves optionally substituted by up to 3 substituents selected from hydroxy, halogeno, cyano, C$_{1-3}$alkyl, C$_{1-3}$alkoxy, C$_{1-3}$alkanoyloxy, trifluoromethyl, cyano, amino, nitro and R$^{14}$ as hereinabove defined)];

provided that when:
m is an integer from 1 to 3;
R$^1$ is methoxy; R$^2$ is hydrogen; Z is —NH—;
R$^3$ is halogeno or C$_{1-3}$alkyl; and
X$^1$ is —O—; then
R$^4$ is not selected from one of the following three groups:
a) —C$_{2-5}$alkylR$^{19}$ (wherein R$^{19}$ is piperidin-4-yl which may bear one or two substituents selected from hydroxy, halogeno, C$_{1-4}$alkyl, C$_{1-4}$hydroxyalkyl and C$_{1-4}$alkoxy);
b) —C$_{2-5}$alkenylR$^{19}$ (wherein R$^{19}$ is as defined hereinbefore);
c) —C$_{2-5}$alkynylR$^{19}$ (wherein R$^{19}$ is as defined hereinbefore);

wherein any alkylene, alkenylene or alkynylene chain in groups a) to c) above are optionally substituted by one or more substituents selected from hydroxy, halogeno amino;
or a pharmaceutically-acceptable salt or prodrug thereof.

According to another aspect of the present invention there is provided a quinazoline derivative of the formula I:

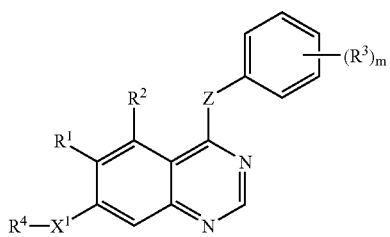

(I)

[wherein:
Z is —O—, —NH— or —S—;
m is an integer from 0 to 5 inclusive;

R$^1$ is hydrogen, hydroxy, halogeno, nitro, trifluoromethyl, cyano, C$_{1-3}$alkyl, C$_{1-3}$alkoxy, C$_{1-3}$alkylthio, or —NR$^5$R$^6$ (wherein R$^5$ and R$^6$, which may be the same or different, are hydrogen or C$_{1-3}$alkyl);
R$^2$ is hydrogen, hydroxy, halogeno, C$_{1-3}$alkyl, C$_{1-3}$alkoxy, trifluoromethyl, amino or nitro;
R$^3$ is hydroxy, halogeno, C$_{1-3}$alkyl, C$_{1-3}$alkoxy, C$_{1-3}$alkanoyloxy, trifluoromethyl, cyano, amino or nitro;
X$^1$ is —O—, —CH$_2$—, —S—, —SO—, —SO$_2$—, —NR$^7$—, —NR$^7$CO—, —CONR$^7$—, —SO$_2$NR$^7$— or —NR$^7$SO$_2$—, (wherein R$^7$ is hydrogen, C$_{1-3}$alkyl or C$_{1-3}$alkoxyC$_{2-3}$alkyl);
R$^4$ is selected from one of the following groups:
1) —Y$^1$X$^2$COR$^8$ [wherein —Y$^1$— is a C$_{2-5}$ alkylene chain wherein each methylene group (other than that of the α-carbon) is optionally substituted by 1 substituent independently selected from hydroxy, halogeno and amino, provided that there is at least 1 and no more than 3 substituents on the C$_{2-5}$alkylene chain; X$^2$ is —O— or —NR$^9$— (in which R$^9$ is hydrogen, C$_{1-3}$alkyl or C$_{1-3}$alkoxyC$_{2-3}$alkyl) and R$^8$ is C$_{1-3}$alkyl, —NR$^{10}$R$^{11}$ or —OR$^{12}$ (wherein R$^{10}$, R$^{11}$ and R$^{12}$, which may be the same or different, are hydrogen, C$_{1-3}$alkyl or C$_{1-3}$alkoxyC$_{2-3}$alkyl)];
2) —Y$^2$—X$^3$R$^{13}$ [wherein Y$^2$— is C$_{2-5}$alkylene, C$_{3-5}$alkenylene or C$_{3-5}$alkynylene wherein each methylene group (other than that of the α-carbon) is optionally substituted by 1 substituent independently selected from hydroxy, halogeno and amino, provided that there is at least 1 substituent and no more than 3 substituents on the alkylene, alkenylene or alkynylene chain; X$^3$ is —O—, —S—, —SO—, —SO$_2$—, —OCO—, —NR$^7$CO—, —CONR$^7$—, —SO$_2$NR$^7$—, —NR$^7$SO$_2$— or —NR$^7$— (wherein R$^7$ is as hereinabove defined) and R$^{13}$ is hydrogen or C$_{1-3}$alkyl, wherein the C$_{1-3}$alkyl group may bear one or two substituents selected from oxo, hydroxy, halogeno and C$_{1-4}$alkoxy;
3) —Y$^1$—X$^6$C$_{1-5}$alkylR$^{14}$ [wherein Y$^1$ is as hereinabove defined and X$^6$ is —O—, —S—, —SO—, —SO$_2$, —NR$^7$CO—, —CONR$^7$—, —SO$_2$NR$^7$—, —NR$^7$SO$_2$— or —NR$^7$— (wherein R$^7$ is as hereinabove defined) and R$^{14}$ is C$_{3-7}$ cycloalkyl or a 3 to 7 membered saturated or partially saturated heterocyclic group containing up to 3 ring heteroatoms selected independently from O, S and N, wherein the carbocyclic or heterocyclic group is optionally substituted by one or two substituents selected from oxo, hydroxy, halogeno, C$_{1-4}$alkyl, (wherein the C$_{1-4}$alkyl group is optionally substituted by 1 or 2 substituents selected from hydroxy, cyano, halogeno, amino, nitro, morpholino, C$_{3-5}$cycloalkyl, piperidin-1-yl and piperazin-1-yl), C$_{2-4}$alkenyl, C$_{2-4}$alkynyl, C$_{1-4}$alkoxy, carbamoyl, C$_{1-3}$alkylcarbamoyl, N,N-di(C$_{1-3}$alkyl)carbamoyl, C$_{2-4}$alkanoyl, C$_{1-4}$alkoxycarbonyl, C$_{1-4}$alkylthio, C$_{1-4}$alkylsulphinyl, C$_{1-4}$alkylsulphonyl, C$_{2-4}$alkanoylamino, N—C$_{1-3}$alkyl-C$_{2-4}$alkanoylamino N—C$_{1-3}$alkylsulphamoyl, N,N-di-[C$_{1-3}$alkyl]sulphamoyl, C$_{1-3}$alkanesulphonylamino and N—C$_{1-3}$alkyl-C$_{1-3}$alkanesulphonylamino, or R$^{14}$ is a pyridone group, a phenyl group or a 5 or 6-membered aromatic heterocyclic group containing 1 to 3 ring heteroatoms independently selected from O, N and S, and wherein the pyridone, phenyl or heterocyclic group is optionally substituted by up to 5 substituents selected from halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, cyano, C$_{1-4}$alkylthio, C$_{1-4}$alkylsulphinyl, C$_{1-4}$alkylsulphonyl, N—C$_{1-3}$alkylsulphamoyl, N,N-di-[C$_{1-3}$alkyl]sulphamoyl, C$_{1-3}$alkanesulphonylamino, N—C$_{1-3}$alkyl-C$_{1-3}$alkanesulphonylamino, —CONR$^{10}$R$^{11}$ and —NR$^{10}$COR$^{11}$ (wherein R$^{10}$ and R$^{11}$ are as hereinabove defined)];

4) —Y$^1$—X$^4$C$_{1-5}$alkylX$^5$R$^{15}$ [wherein Y$^1$ is as hereinabove defined and X$^4$ and X$^5$ which may be the same or different are each —O—, —S—, —SO—, —SO$_2$—, —NR$^7$CO—, —CONR$^7$—, —SO$_2$NR$^7$—, —NR$^7$SO$_2$— or —NR$^7$— (wherein R$^7$, is as hereinabove defined and R$^{15}$ is hydrogen or C$_{1-3}$alkyl)];

5) —Y$^1$—O—C$_{1-3}$alkyl (wherein Y$^1$ is as hereinabove defined) provided that X$^1$ is —O—, —S—, —SO— or —SO$_2$—;

6) —Y$^2$—R$^{16}$ {wherein —Y$^2$— is as hereinabove defined and R$^{16}$ is a saturated or partially saturated 3 to 7 membered heterocyclic ring containing up to 3 heteroatoms selected from O, S and N [wherein the heterocyclic ring is optionally substituted by up to 3 substituents selected from oxo, hydroxy, halogeno, C$_{1-4}$alkyl, C$_{2-4}$alkenyl, C$_{2-4}$alkynyl and C$_{3-7}$cycloalkyl (wherein C$_{1-4}$alkyl, C$_{2-4}$alkenyl, C$_{2-4}$alkynyl and C$_{3-7}$cycloalkyl are themselves optionally substituted by up to 3 substituents selected from hydroxy, halogeno, cyano, C$_{1-3}$alkyl, C$_{1-3}$alkoxy, C$_{1-3}$alkanoyloxy, trifluoromethyl, amino, nitro and R$^{14}$ as hereinabove defined), C$_{1-4}$alkoxy, carbamoyl, C$_{1-4}$alkylcarbamoyl, N—N-di(C$_{1-4}$alkyl)carbamoyl, C$_{2-4}$alkanoyl, C$_{1-4}$alkoxycarbonyl, C$_{3-7}$cycloalkyl, C$_{1-4}$alkylthio, C$_{1-4}$alkylsulphinyl, C$_{1-4}$alkylsulphonyl, C$_{2-4}$alkanoylamino, N—C$_{1-3}$alkyl-C$_{2-4}$alkanoylamino, N—C$_{1-3}$alkylsulphamoyl, N,N-di-[C$_{1-3}$alkyl]sulphamoyl, C$_{1-3}$alkanesulphonylamino and N—C$_{1-3}$alkyl-C$_{1-3}$alkanesulphonylamino or R$^{16}$ is a pyridone group, a phenyl group or a 5 or 6-membered aromatic heterocyclic group containing 1 to 3 ring heteroatoms independently selected from O, N and S, and wherein the pyridone, phenyl or heterocyclic group is optionally substituted by up to 5 substituents selected from halogeno, amino, C$_{1-4}$alkyl, C$_{1-4}$alkoxy, C$_{1-4}$hydroxyalkyl, C$_{1-4}$aminoalkyl, C$_{1-4}$alkylamino, C$_{1-4}$hydroxyalkoxy, carboxy, cyano, C$_{1-4}$alkylthio, C$_{1-4}$alkylsulphinyl, C$_{1-4}$alkylsulphonyl, N—C$_{1-3}$alkylsulphamoyl, N,N-di-[C$_{1-3}$alkyl]sulphamoyl, C$_{1-3}$alkanesulphonylamino, N—C$_{1-3}$alkyl-C$_{1-3}$alkanesulphonylamino, —CONR$^{10}$R$^{11}$ and —NR$^{10}$COR$^{11}$ (wherein R$^{10}$ and R$^{11}$ are as hereinabove defined)];

7) —Y$^2$—X$^6$—R$^{14}$ (wherein Y$^2$, X$^6$ and R$^{14}$ are as hereinabove defined); and 8) —Y$^2$—NR$^{17}$R$^{18}$ [wherein Y$^2$ is as hereinabove defined and R$^{17}$ and R$^{18}$ are independently selected from hydrogen, C$_{1-6}$alkyl, C$_{2-6}$alkenyl, C$_{2-6}$alkynyl or C$_{1-3}$alkoxy C$_{1-6}$alkyl (wherein any alkyl group in R$^{17}$ or R$^{18}$ is optionally substituted by up to 2 substituents selected from hydroxy, halogeno, C$_{1-3}$alkyl, C$_{1-3}$alkoxy, C$_{1-3}$alkanoyloxy, trifluoromethyl, cyano, amino or nitro)];

9) —Y$^3$—R$^a$ (wherein Y$^3$ is C$_{1-5}$alkylene, C$_{2-5}$alkenylene or C$_{2-5}$alkynylene wherein each methylene group (other than that of the α-carbon) is optionally substituted by 1 substituent independently selected from hydroxy, halogeno and amino, provided that there are no more than 3 substituents on the alkylene, alkenylene or alkynylene chain, and R$^a$ is C$_{3-7}$cycloalkyl which is substituted by 1 substituent selected from hydroxy, amino and halogeno on the ring carbon linked to Y$^3$ and additionally optionally substituted by up to 3 substituents selected from oxo, hydroxy, halogeno, C$_{1-4}$alkyl, C$_{2-4}$alkenyl, C$_{2-4}$alkynyl, C$_{1-4}$alkoxy, carbamoyl, C$_{1-4}$alkylcarbamoyl, N—N-di (C$_{1-4}$alkyl)carbamoyl, C$_{2-4}$alkanoyl, C$_{1-4}$alkoxycarbonyl and C$_{3-7}$cycloalkyl (wherein C$_{1-4}$alkyl, C$_{2-4}$alkenyl, C$_{2-4}$alkynyl and C$_{3-7}$cycloalkyl are themselves optionally substituted by up to 3 substituents selected from hydroxy, halogeno, cyano, C$_{1-3}$alkyl, C$_{1-3}$alkoxy, C$_{1-3}$alkanoyloxy, trifluoromethyl, cyano, amino, nitro and R$^{14}$ as hereinabove defined)];

provided that when:

m is an integer from 1 to 3;

R$^1$ is methoxy; R$^2$ is hydrogen; Z is —NH—;

R$^3$ is halogeno or C$_{1-3}$alkyl; and

X$^1$ is —O—; then

R$^4$ is not selected from one of the following three groups:

a) —C$_{2-5}$alkylR$^{19}$ (wherein R$^{19}$ is piperidin-4-yl which may bear one or two substituents selected from hydroxy, halogeno, C$_{1-4}$alkyl, C$_{1-4}$hydroxyalkyl and C$_{1-4}$alkoxy);

b) —C$_{2-5}$alkenylR$^{19}$ (wherein R$^{19}$ is as defined hereinbefore);

c) —C$_{2-5}$alkynylR$^{19}$ (wherein R$^{19}$ is as defined hereinbefore);

wherein any alkylene, alkenylene or alkynylene chain in groups a) to c) above are optionally substituted by one or more substituents selected from hydroxy, halogeno and amino, or a pharmaceutically-acceptable salt or prodrug thereof.

In this specification the generic term "alkyl" includes both straight-chain and branched-chain alkyl groups. However references to individual alkyl groups such as "propyl" are specific for the straight-chain version only and references to individual branched-chain alkyl groups such as "isopropyl" are specific for the branched-chain version only. An analogous convention applies to other generic terms.

It is to be understood that, insofar as certain of the compounds of Formula I defined above may exist in optically active or racemic forms by virtue of one or more asymmetric carbon atoms, the invention includes in its definition any such optically active or racemic form which possesses the above-mentioned activity. The synthesis of optically active forms may be carried out by standard techniques of organic chemistry well known in the art, for example by synthesis from optically active starting materials or by resolution of a racemic form. Similarly, the above-mentioned activity may be evaluated using the standard laboratory techniques referred to hereinafter.

In formula I, as hereinbefore defined, hydrogen will be present at positions 2 and 8 of the quinazoline group.

The drawings within this specification can represent only one of the possible tautomeric forms. It is to be understood that the invention encompasses any tautomeric form which inhibits VEGF receptor tyrosine kinase activity and is not to be limited merely to any one tautomeric form utilised within the formulae drawings.

It is also to be understood that certain quinazolines of the formula I and salts thereof can exist in solvated as well as unsolvated forms such as, for example, hydrated forms. It is to be understood that the invention encompasses all such solvated forms which inhibit VEGF receptor tyrosine kinase activity.

For the avoidance of any doubt, it is to be understood that when X$^1$ is, for example, a group of formula —NR$^7$CO—, it is the nitrogen atom bearing the R$^7$ group which is attached to the quinazoline ring and the carbonyl (CO) group is attached to R$^4$, whereas when X$^1$ is, for example, a group of formula —CONR$^7$—, it is the carbonyl group which is attached to the quinazoline ring and the nitrogen atom bearing the R$^7$ group is attached to R$^4$. A similar convention applies to the other two atom X$^1$ linking groups. When X$^1$ is —NR$^7$— it is the nitrogen atom bearing the R$^7$ group which is linked to the quinazoline ring and to $R^4$. An analogous convention applies to other groups. It is further to be understood that when $X^1$ is —$NR^7$— and $R^7$ is $C_{1-3}$alkoxy$C_{2-3}$alkyl it is the $C_{2-3}$alkyl moiety which is linked to the nitrogen atom of $X^1$ and an analogous convention applies to other groups.

The α-carbon in the alkylene, alkenylene or alkynylene chains in $Y^1$ and $Y^2$ is the carbon atom in the chain which is linked to $X^1$. The β-carbon is the carbon atom in the carbon chain linked to the α-carbon.

Preferred values for $Y^1$ include 2-acetoxypropylene, 2-hydroxyethylene, 2-hydroxypropylene, 3-hydroxypropylene, 2-hydroxybutylene, 3-hydroxybutylene and 4-hydroxybutylene.

Suitable values for $Y^1$ include 2-hydroxyethylene, 2-hydroxypropylene, 3-hydroxypropylene, 2-hydroxybutylene, 3-hydroxybutylene and 4-hydroxybutylene.

Suitable values for $Y^2$ include those mentioned above for $Y^1$ and 2-hydroxybut-3-enylene, 2-hydroxypent-3-enylene, 4-hydroxybut-2-enylene and 3-hydroxypent-4-enylene.

More preferred values of $Y^1$ are 2-hydroxypropylene and 2-acetoxypropylene.

More preferred values of $Y^2$ are 2-hydroxypropylene and 2-acetoxypropylene.

Examples of 5 or 6 membered aromatic heterocyclic groups for ring A include furan, pyrrole, thiophene, oxazole, isoxazole, imidazole, pyrazole, thiazole, isothiazole, oxadiazole, thiadiazole, triazole, tetrazole, pyridine, pyridazine, pyrimidine, pyrazine, 1,3,5-triazine, indole.

Examples of suitable 3 to 7 membered saturated or partially saturated heterocyclic groups for $R^{14}$ and $R^{16}$ include pyrrolidine, piperidine, aziridine, azetidine, piperazine, homopiperidine, pyrroline, morpholine, thiomorpholine, (tetrahydro-1,4-thiazine), thiazolidine, 1,2,6-tetrahydropyridine, tetrahydrofuran, tetrahydropyran, 1,1-dioxotetrahydro-1,4-thiazine, homopiperazine dihydropyridine, tetrahyrdropyridine, dihydropyrimidine and tetrahydropyrimidine.

Examples of suitable $C_{3-7}$cycloalkyl groups in $R^{14}$, $R^{16}$ and $R^a$ include, cyclopropyl, cyclobutyl, cyclopentyl, cyclohexyl and cycloheptyl. Particularly cyclopropyl, cyclopentyl and cyclohexyl.

Examples of 5 or 6 membered aromatic heterocyclic groups for $R^{14}$ and $R^{16}$ include furan, pyrrole, thiophene, oxazole, isoxazole, imidazole, pyrazole, thiazole, isothiazole, oxadiazole, thiadiazole, triazole, tetrazole, pyridine, pyridazine, pyrimidine, pyrazine, 1,3,5-triazine, indole.

Preferred 5 or 6-membered aromatic heterocyclic groups for $R^{14}$ and $R^{16}$ include pyridine, imidazole, thiophene, triazole, and pyridazine. Most preferably pyridine, imidazole or triazole.

Suitable values for any of the 'R' groups ($R^1$ to $R^{19}$), or for various substituent groups on an alkyl chain or ring system in $R^4$ include:

| | |
|---|---|
| for halogeno | fluoro, chloro, bromo and iodo; |
| for $C_{1-6}$alkyl: | methyl, ethyl, propyl, isopropyl and tert-butyl; |
| for $C_{2-5}$alkenyl: | vinyl, allyl and but-2-enyl; |
| for $C_{2-5}$alkynyl: | ethynyl, 2-propynyl and but-2-ynyl; |
| for $C_{1-6}$alkoxy: | methoxy, ethoxy, propoxy, isopropoxy and butoxy; |
| for $C_{2-6}$alkenyloxy: | vinyloxy and allyloxy; |
| for $C_{2-6}$alkynyloxy: | ethynyloxy and 2-propynyloxy; |
| for $C_{1-4}$alkylthio: | methylthio, ethylthio and propylthio; |
| for $C_{1-4}$alkylsulphinyl: | methylsulphinyl and ethylsulphinyl; |
| for $C_{1-4}$alkylsulphonyl: | methylsulphonyl and ethylsulphonyl; |
| for $C_{1-4}$alkylamino: | methylamino, ethylamino, propylamino, isopropylamino and butylamino; |
| for di-[$C_{1-4}$alkyl]amino: | dimethylamino, diethylamino, N-ethyl-N-methylamino and diisopropylamino; |
| for $C_{1-4}$alkoxycarbonyl: | methoxycarbonyl, ethoxycarbonyl, propoxycarbonyl and tert-butoxycarbonyl; |
| for N-$C_{1-4}$alkylcarbamoyl: | N-methylcarbamoyl, N-ethylcarbamoyl and N-propylcarbamoyl; |
| for N,N-di-[$C_{1-4}$alkyl]carbamoyl: | N,N-dimethylcarbamoyl, N-ethyl-N-methylcarbamoyl and N,N-diethylcarbamoyl; |
| for $C_{2-4}$alkanoyl: | acetyl and propionyl; |
| for $C_{1-4}$alkanoyloxy: | acetoxy and propionyloxy; |
| for $C_{2-4}$alkanoylamino: | acetamido and propionamido; |
| for N-$C_{1-3}$alkyl-$C_{2-4}$alkanoylamino: | N-methylacetamido and N-methylpropionamido; |
| for N-$C_{1-3}$alkylsulphamoyl: | N-methylsulphamoyl and N-ethylsulphamoyl; |
| for N,N-di-[$C_{1-3}$alkyl]sulphamoyl: | N,N-dimethylsulphamoyl; |
| for $C_{1-3}$alkanesulphonylamino: | methanesulphonylamino and ethanesulphonylamino; |
| for N-$C_{1-3}$alkyl-$C_{1-3}$alkanesulphonylamino: | N-methylmethanesulphonylamino and N-methylethanesulphonylamino. |

Preferrred substituents for saturated or partially saturated heterocyclic groups in $R^{14}$ and $R^{16}$ include oxo, hydroxy, halogeno, $C_{1-4}$alkyl, (wherein the $C_{1-4}$alkyl group is optionally substituted by 1 or 2 substituents selected from hydroxy, cyano, halogeno, amino, nitro, morpholino, $C_{3-5}$cycloalkyl, piperidin-1-yl and piperazin-1-yl), $C_{2-4}$alkenyl, $C_{2-4}$alkynyl, $C_{1-4}$alkoxy, carbamoyl, $C_{1-3}$alkylcarbarmoyl, N,N-di($C_{1-3}$ alkyl)carbamoyl, $C_{2-4}$alkanoyl and $C_{1-4}$alkoxycarbonyl.

In another aspect of the present invention preferred substituents for saturated or partially saturated heterocyclic groups in $R^{14}$ and $R^{16}$ include oxo, hydroxy, halogeno, $C_{1-4}$alkyl, (wherein the $C_{1-4}$alkyl group is optionally substituted by 1 or 2 substituents selected from hydroxy, cyano, halogeno, amino, morpholino, $C_{3-5}$cycloalkyl, piperidin-1-yl and piperazin-1-yl), $C_{2-4}$alkenyl, $C_{2-4}$alkynyl, $C_{1-4}$alkoxy, carbamoyl, $C_{1-3}$alkylcarbamoyl, N,N-di($C_{1-3}$alkyl)carbamoyl, $C_{2-4}$alkanoyl and $C_{1-4}$alkoxycarbonyl.

More preferred substituents for saturated or partially saturated heterocyclic groups in $R^{14}$ and $R^{16}$ include oxo, hydroxy, halogeno, $C_{1-4}$alkyl (optionally substituted by hydroxy, cyano, morpholino, cyclopentyl, piperidin-1-yl or piperazin-1-yl), alkyl, $C_{1-4}$alkoxy, $C_{2-4}$alkanoyl or $C_{1-4}$alkoxycarbonyl.

More preferrred substituents for saturated or partially saturated heterocyclic groups in $R^{14}$ and $R^{16}$ include oxo, hydroxy, halogeno, $C_{1-4}$alkyl (optionally substituted by hydroxy, cyano, morpholino, cyclopentyl, piperidin-1-yl or piperazin-1-yl), alkyl, $C_{1-4}$alkoxy, $C_{2-4}$alkanoyl or $C_{1-4}$alkoxycarbonyl.

More preferred substituents for saturated or partially saturated heterocyclic groups in in $R^{14}$ and $R^{16}$ include oxo, hydroxy, fluoro, chloro, bromo, methyl, ethyl, hydroxymethyl, 2-hydroxyethyl, 3-hydroxypropyl, 2-morpholinoethyl, cyclopropyl, allyl, methoxy, acetyl and methoxycarbonyl.

Preferred substituents for ring carbon atoms in saturated or partially saturated heterocyclic groups in $R^{14}$ and $R^{16}$ include hydroxy, bromo and methyl. Most preferably ring carbon atoms in saturated or partially saturated heterocyclic groups in $R^{14}$ and $R^{16}$ are unsubstituted.

Preferred substituents for ring NH groups in saturated or partially saturated heterocyclic groups in $R^{14}$ and $R^{16}$ include $C_{1-4}$alkyl (optionally substituted as hereinabove defined), $C_{2-5}$ alkyl, $C_{2-4}$alkanoyl or $C_{1-4}$alkoxycarbonyl. More preferably, $C_{1-4}$alkyl (optionally substituted by hydroxy, fluoro, chloro, bromo, cyclopentyl, morpholino, piperazin-1-yl or piperidin-1-yl), acetyl, allyl or methoxycarbonyl.

Preferably the aromatic group in $R^{14}$ and $R^{16}$ is substituted by up to 3 substituents. More preferably up to 2 substituents.

Preferred substituents for aromatic groups in $R^{14}$ and $R^{16}$ include halogeno, $C_{1-4}$ alkyl, amino, $C_{1-4}$ alkoxy, hydroxy$C_{1-4}$alkyl or $C_{1-4}$hydroxyalkoxy. More preferred substituents include fluoro, chloro, bromo, methyl, ethyl, methoxy, hydroxymethyl and 2-hydroxyethyl.

Preferably ring A is phenyl or a 5–6-membered heteroaromatic moiety which contains 1–3 heteroatoms selected independently from O, N and S.

More preferably ring A is phenyl or a 6-membered heteroaromatic moiety which contains 1–3 heteroatoms selected independently from O, N and S.
Yet more preferably ring A is phenyl or pyridyl.
Most preferably ring A is phenyl.
In another aspect ring A is pyridyl.

Preferably m is an integer from 1 to 5 inclusive. More preferably m is 2 or 3. Most preferably m is 2.

Preferably $R^1$ is hydrogen, hydroxy, cyano, nitro, trifluoromethyl, $C_{1-3}$alkyl, $C_{1-3}$alkoxy or amino.

More preferably, $R^1$ is hydrogen, hydroxy, cyano, nitro, trifluoromethyl, methyl, ethyl, methoxy or ethoxy. Even more preferably $R^1$ is hydrogen, methyl or methoxy. Most preferably $R^1$ is hydrogen or methoxy, but especially methoxy.

Preferably, $R^2$ is hydrogen, fluoro, amino or nitro. Most preferably $R^2$ is hydrogen. Preferably $R^3$ is hydroxy, halogeno, $C_{1-2}$alkyl, $C_{1-2}$alkoxy, trifluoromethyl cyano, amino or nitro.

More preferably, $R^3$ is fluoro, chloro, bromo, methyl or methoxy.

Particular values for ring A bearing $(R^3)_m$ are 2-fluoro-4-chloro-5-hydroxyphenyl, 2-fluoro-4-bromo-5-hydroxyphenyl, 2-fluoro-4-chlorophenyl or 2-fluoro-4-bromophenyl.

Preferably, when ring A is phenyl, m is 2 and the phenyl ring is substituted in the 2- and 4-positions.

Preferably, when ring A is phenyl, m is 2 and the phenyl ring is substituted in the 2- and 4-positions by substituents independently selected from fluoro, chloro and bromo.

More preferably, ring A bearing $(R^3)_m$ is 2-fluoro-4-chlorophenyl or 2-fluoro-4-bromophenyl. In another aspect ring A bearing $(R^3)_m$ is 2-chloro-3-methoxyphenyl, 2-bromo-3-chlorophenyl, 2,3-dibromophenyl, 2,3-dichlorophenyl 2,4-dichlorophenyl, 2-bromo-4-chlorophenyl, 2-chloro-3-methylphenyl, 2-bromo-4-methylphenyl, 2-chloro-3-methoxyphenyl or 3-chloro-4-fluorophenyl.

Preferably $X^1$ is —O—, —S—, —NR$^7$CO—, —NR$^7$SO$_2$— or —NR$^7$— (wherein $R^7$ is hydrogen, $C_{1-2}$alkyl or $C_{1-2}$alkoxyethyl).

Preferably $X^1$ is —O—, —S—, —NR$^7$CO— or —NR$^7$SO$_2$— (wherein $R^7$ is hydrogen, methyl or ethyl).

More preferably $X^1$ is —O—, —S—, —NR$^7$CO— (wherein $R^7$ is hydrogen or methyl).

Yet more preferably $X^1$ is —O—, or —NHCO—, or —S—.
Yet more preferably $X^1$ is —O—, or —S—.
Most preferably $X^1$ is —O—.

Preferably $X^2$ is —O— or —NR$^9$— (wherein $R^9$ is hydrogen, $C_{1-3}$alkyl or $C_{1-2}$alkoxyethyl).

Preferably $X^3$ is —O—, —S—, —SO—, —SO$_2$—, —NR$^7$CO—, —NR$^7$SO$_2$— or —NR$^7$— (wherein $R^7$ is hydrogen, $C_{1-2}$alkyl or $C_{1-2}$alkoxyethyl).

More preferably $X^3$ is —O—, —S—, —SO—, —SO$_2$— or —NR$^7$— (wherein $R^7$ is hydrogen, $C_{1-2}$alkyl or $C_{1-2}$alkoxyethyl).

Yet more preferably $X^3$ is —O— or —NR$^7$— (wherein $R^7$ is hydrogen, methyl or ethyl).

Preferably $X^4$ and $X^5$ which may be the same or different are each —O—, —S—, —SO—, —SO$_2$— or —NR$^7$— (wherein $R^7$ is hydrogen, $C_{1-3}$alkyl or $C_{1-2}$alkoxyethyl).

More preferably $X^4$ and $X^5$, which may be the same or different, are each —O—, —S— or —NR$^7$— (wherein $R^7$ is hydrogen, methyl, ethyl or $C_{1-2}$alkoxyethyl).

More preferably $X^4$ and $X^5$ which may be the same or different are each —O— or —NH—.

Preferably $X^6$ is —O—.

Preferably $R^4$ is selected from one of the following groups:

1a) —Y$^1$—X$^2$ COR$^8$ (wherein Y$^1$, X$^2$ and R$^8$ are as hereinabove defined);

2a) —Y$^1$—X$^3$ R$^{13}$ (wherein Y$^1$, X$^2$ and R$^{13}$ are as hereinabove defined);

3a) —Y$^1$—R$^{20}$ (wherein Y$^1$ is as hereinabove defined and R$^{20}$ is a 3 to 7 membered saturated or partially saturated heterocyclic group containing 1 or 2 ring atoms independently selected from O, S and N wherein the heterocyclic group may bear 1 or 2 substituents selected from oxo, hydroxy, halogeno, $C_{1-4}$alkyl (optionally substituted by hydroxy, halogeno, cyano, $C_{5-7}$cycloalkyl or a 5 or 6 membered saturated heterocyclic group containing one or two ring heteroatoms independently selected from O, S and N), $C_{2-5}$alkenyl, $C_{2-5}$alkynyl, $C_{1-4}$alkoxy, carbamoyl, $C_{1-4}$alkylcarbamoyl, N,N-di($C_{1-4}$alkyl)carbamoyl, $C_{1-4}$ alkanoyl and $C_{1-4}$alkoxycarbonyl;

4a) —Y$^1$—X$^4$C$_{1-5}$alkylX$^5$R$^{15}$ (wherein Y$^1$, X$^4$, X$^5$ and R$^{15}$ are as hereinabove defined), 5a) $C_{1-3}$alkoxy-Y$^1$—, (wherein Y$^1$ is as hereinabove defined) provided that X$^1$ is —O—, —S—, —SO— or —SO$_2$—;

6a) —Y$^1$—X$^6$C$_{1-5}$alkylR$^{21}$ (wherein Y$^1$ and X$^6$ are as hereinabove defined and R$^{21}$ is cyclopentyl, cyclohexyl or a 5 or 6 membered saturated heterocyclic group containing 1 or 2 ring heteroatoms selected independently from O, S and N, wherein the cyclopentyl, cyclohexyl or heterocyclic group may bear one or two substituents selected from oxo, hydroxy, halogeno, $C_{1-4}$alkyl, $C_{1-4}$hydroxyalkyl, $C_{1-4}$alkoxy, carbamoyl, $C_{1-4}$alkylcarbamoyl, N,N-di($C_{1-4}$alkyl)carbamoyl, $C_{1-4}$alkanoyl and $C_{1-4}$alkoxycarbonyl;

7a) —Y$^1$X$^6$R$^{21}$ (wherein Y$^1$, X$^6$ and R$^{21}$ are as hereinabove defined); and 8a) —Y$^1$—NR$^{17}$R$^{18}$ (wherein Y$^1$, R$^{17}$ and R$^{18}$ are as hereinabove defined).

More preferably R$^4$ is selected from one of the following groups:

1b) —Y$^1$—R$^{20}$;
2b) $C_{1-3}$alkoxy-Y$^1$—,
3b) —Y$^1$—X$^6$—R$^{21}$;
4b) —Y$^1$—NR$^{17}$R$^{18}$;

wherein Y$^1$, X$^6$, R$^a$, R$^{17}$, R$^{18}$, R$^{20}$ and R$^{21}$ are as hereinabove defined and Y$^4$ is a C$_{2-5}$ alkylene chain wherein each methylene group (other than that of the α-carbon) is optionally substituted by 1 substituent independently selected from hydroxy, halogeno and amino, provided that there are no more than 3 substituents on the $C_{2-5}$alkylene chain;

Yet more preferably $R^4$ is selected from one of the following groups:

1c) —$Y^1$—$R^{22}$;
2c) $C_{1-3}$alkoxy-$Y^1$—;
3c) $Y^1$—$X^6$—$R^{22}$;
4c) —$Y^1$—$NR^{17}R^{18}$;

wherein $Y^1$, $Y^4$, $X^6$, $R^a$, $R^{17}$ and $R^{18}$ are as hereinabove defined and $R^{22}$ is cyclopentyl, cyclohexyl, pyrrolidinyl, piperidinyl, azetidinyl, piperazinyl, homopiperidinyl, pyrrolyl, morpholino, thiomorpholino, morpholinyl, thiomorpholinyl, thiazolidinyl and 1,2,6-tetrahydropyridyl each of the aforementioned ring systems being optionally substituted by 1 or 2 substitutents selected from oxo, hydroxy, halogeno, $C_{1-4}$alkyl, $C_{1-4}$alkoxy, hydroxy$C_{1-4}$alkyl, $C_{2-4}$alkanoyl and $C_{1-4}$alkoxycarbonyl.

Preferably the alkylene, alkenylene or alkynylene group in $Y^1$ or $Y^2$ in $R^4$ is substituted by a hydroxy, halogeno, amino or $C_{1-4}$alkanoyloxy group on the β-carbon.

Preferably the alkylene, alkenylene or alkynylene group in $Y^1$ or $Y^2$ in $R^4$ is substituted by a hydroxy, halogeno or amino group on the β-carbon.

Preferably the alkylene, alkenylene or alkynylene chain in $Y^1$ or $Y^2$ in $R^4$ is substitued by hydroxy or acetoxy.

Preferably $Y^2$ in $R^4$ is $C_{2-5}$alkylene wherein each methylene group (other than that of the α-carbon) is optionally substituted by 1 substituent independently selected from hydroxy, halogeno, amino and $C_{1-4}$alkanoyloxy provided that there is at least 1 substituent and no more than 3 substituents on the alkylene, alkenylene or alkynylene chain.

Preferably $Y^2$ in $R^4$ is $C_{2-5}$alkylene wherein each methylene group (other than that of the α-carbon) is optionally substituted by 1 substituent independently selected from hydroxy, halogeno and amino, provided that there is at least 1 substituent and no more than 3 substituents on the alkylene, alkenylene or alkynylene chain.

Preferably $Y^1$ or $Y^2$ in $R^4$ is substituted by only 1 substituent selected from hydroxy, halogeno, amino and acetoxy. More preferably $Y^1$ or $Y^2$ in $R^4$ is an $C_{2-5}$alkylene chain which is substituted by 1 substituent, on the β-carbon, selected from hydroxy, halogeno, amino and acetoxy. Yet more preferably $Y^1$ or $Y^2$ in $R^4$ is 2-hydroxypropylene, 2-acetoxypropylene or 2-hydroxybutylene. Especially preferably $Y^1$ or $Y^2$ in $R^4$ is 2-hydroxypropylene or 2-acetoxypropylene.

Preferably $Y^1$ or $Y^2$ in $R^4$ is substituted by only 1 substituent selected from hydroxy, halogeno and amino. More preferably $Y^1$ or $Y^2$ in $R^4$ is an $C_{2-5}$alkylene chain which is substituted by 1 substituent, on the α-carbon, selected from hydroxy, halogeno and amino. Yet more preferably $Y^1$ or $Y^2$ in $R^4$ is 2-hydroxypropylene or 2-hydroxybutylene. Most preferably $Y^1$ or $Y^2$ in $R^4$ is 2-hydroxypropylene.

Preferably $Y^3$ is C, alkylene wherein each methylene group (other than that of the α-carbon) is optionally substituted by 1 substituent independently selected from hydroxy, halogeno and amino, provided that there are no more than 2 substituents on the alkylene, chain. More preferably $Y^3$ in $R^4$ is unsubstituted or substituted by 1 substituent selected from hydroxy, halogeno or amino. Yet more preferably $Y^3$ in $R^4$ is methylene, ethylene or propylene. Most preferably $Y^3$ in $R^4$ is methylene.

Preferably $R^4$ is of the formula —$Y^2$—$R^{16}$—$Y^2$—$NR^{17}R^{18}$ or $Y^3R^a$, wherein $Y^2$, $Y^3$, $R^a$, $R^{16}$, $R^{17}$ and $R^{18}$ are as hereinabove defined.

More preferably $R^4$ is of the formula —$Y^1$—$R^{16}$, —$Y^2$—$NR^{17}R^{18}$ or —$Y^3$—$R^a$, wherein $Y^1$ and $Y^3$ are as hereinabove defined, $R^{16}$ is a 4 to 7-membered saturated or partially saturated heterocyclic group containing one or two ring heteroatoms independently selected from O, S and N and wherein the heterocyclic ring is optionally substituted as hereinabove defined, and $R^a$, $R^{17}$ and $R^{18}$ are as hereinabove defined.

Preferably $R^{16}$ is a 4 to 7 membered saturated or partially saturated heterocyclic group containing one ring nitrogen atom and optionally containing one additional ring heteroatom selected from O, S and N and wherein the heterocyclic ring is linked to —$Y^2$— through the ring nitrogen atom and wherein the heterocyclic ring is optionally substituted as hereinabove defined.

Preferred heterocylic groups for $R^{16}$ in include pyrrolidine, piperidine, azetidine, piperazine, homopiperidine, pyrroline, morpholine, thiomorpholine, thiazolidine and 1,2,6-tetrahydropyridine.

Preferred optional substituents for a heterocyclic group in $R^{16}$ include oxo, hydroxy, $C_{1-4}$alkyl, $C_{1-4}$hydroxyalkyl, $C_{1-4}$alkoxy, $C_{1-4}$alkanoyl, $C_{2-5}$cycloalkyl, or a 5- or 6-membered saturated or partially saturated heterocyclic ring containing one or two ring heteroatoms selected from O, S and N.

More preferred optional substituents for a heterocyclic group in $R^{16}$ include, oxo, hydroxy, methyl, ethyl, cyanomethyl, 2-cyanoethyl, 3-cyanopropyl, hydroxymethyl, 2-hydroxyethyl, 3-hydroxypropyl, methoxy, ethoxy, acetyl, cyclopropyl, vinyl, allyl and 2-morpholinoethyl.

Preferred optional substituents for ring carbon atoms in a heterocyclic group in $R^{16}$ include methyl and hydroxy. Preferred optional substituents for ring nitrogen atoms in a heterocyclic group in $R^{16}$ include $C_{1-4}$alkyl, hydroxy$C_{1-4}$alkyl, $C_{1-5}$alkenyl, $C_{1-5}$alkanoyl, $C_{2-5}$alkynyl, $C_{2-5}$cycloalkyl and $C_{1-3}$alkyl substituted by a heterocyclic group. More preferred optional substituents for ring nitrogen atoms in a heterocyclic group in $R^{16}$ include methyl, 2-hydroxyethyl, allyl, 2-hydroxyethyl, 3-hydroxypropyl, cylcopropyl and 2-morpholinoethyl. Preferably the heterocyclic group in $R^{16}$ is unsubstituted.

Preferably $R^a$ is $C_{3-7}$cycloalkyl wherein the ring is linked to —$Y^3$— through a ring carbon atom which is substituted by hydroxy, amino or halogeno and wherein the ring is optionally further substituted as hereinabove defined.

More preferably $R^a$ is $C_{3-7}$cycloalkyl wherein the ring is linked to —$Y^3$— through a ring carbon atom which is substituted by hydroxy and wherein the ring is optionally substituted as hereinabove defined.

Preferably $R^a$ is hydroxycyclopropyl, hydroxycyclobutyl, hydroxycyclopentyl, hydroxycyclohexyl, wherein the hydroxy group is a substituent on the ring carbon atom linked to $Y^3$ and the rings are optionally further substituted by 1 or 2 substituents selected from oxo, hydroxy, $C_{1-4}$alkyl, $C_{1-4}$hydroxyalkyl, $C_{1-4}$alkoxy, $C_{1-4}$alkanoyl, $C_{2-5}$cycloalkyl, or a 5- or 6-membered saturated or partially saturated heterocyclic ring containing one or two ring heteroatoms selected from O, S and N.

Most preferably $R^a$ is 1-hydroxycyclopentyl or 1-hydroxycyclohexyl.

Preferred substituents for $R^a$ are as hereinabove defined for $R^{16}$.

Preferably $R^{17}$ and $R^{18}$ in $NR^7R^{18}$ are independently selected from hydrogen, $C_{1-4}$alkyl, hydroxy$C_{1-4}$alkyl, cyano$C_{1-4}$alkyl, $C_{2-5}$alkenyl, $C_{2-5}$alkynyl, $C_{1-4}$alkoxy$C_{1-3}$alkyl, and hydroxy$C_{1-3}$alkoxy$C_{1-3}$alkyl.

More preferably $R^{17}$ and $R^{18}$ in $NR^{17}R^{18}$ are independently selected from hydrogen, methyl, ethyl, propyl, isopropyl, 2-methylpropyl, cyanomethyl, 2-cyanoethyl, 2-hydroxyethyl, vinyl, allyl, 2-(ethoxy)ethyl and 2-(2-hydroxyethoxy)ethyl. Preferably one of $R^{17}$ and $R^{18}$ is hydrogen or methyl.

Most preferably $R^{17}$ and $R^{18}$ are independently selected from hydrogen, methyl, ethyl, propyl, isopropyl, 2-methylpropyl, and allyl.

A particular class of compounds is of the formula (I) wherein:
ring A is phenyl or pyridyl, especially phenyl;
m is 1, 2 or 3;
Z, $R^1$, $R^2$ and $R^3$ are as hereinbefore defined; $X^1$ is —O—, —S—, —$NR^7CO$—, —$NR^7SO_2$— or —$NR^7$— (wherein $R^7$ is hydrogen, methyl, ethyl, methoxyethyl or ethoxyethyl); and $R^4$ is selected from groups 1a) to 8a) as hereinabove defined;
provided that when:
m is an integer from 1 to 3;
$R^1$ is methoxy; $R^2$ is hydrogen; Z is —NH—;
$R^3$ is halogeno or $C_{1-3}$alkyl; and
$X^1$ is —O—; then
$R^4$ is not selected from one of the following three groups:
a) —$C_{2-5}$alkyl$R^{19}$ (wherein $R^{19}$ is piperidin-4-yl which may bear one or two substituents selected from hydroxy, halogeno, $C_{1-4}$alkyl, $C_{1-4}$hydroxyalkyl and $C_{1-4}$alkoxy);
b) —$C_{2-5}$alkenyl$R^{19}$ (wherein $R^{19}$ is as defined hereinbefore);
c) —$C_{2-5}$alkynyl$R^{19}$ (wherein $R^{19}$ is as defined hereinbefore);

wherein any alkyl, alkenyl or alkynyl group is optionally substituted by one or more substituents selected from hydroxy, halogeno and amino;

or a pharmaceutically-acceptable salt or prodrug thereof.

A further particular class of compound is of the formula (I) wherein:
ring A is phenyl;
m is 1, 2 or 3; Z is —NH—;
$R^1$, $R^2$ and $R^3$ are as hereinabove defined; $X^1$ is —O—, —S—, —$NR^7CO$—, —$NR^7SO_2$— or —$NR^7$— (wherein $R^7$ is hydrogen, methyl, ethyl or methoxyethyl); and $R^4$ is selected from groups 1b) to 4b) as hereinabove defined;
provided that when:
m is an integer from 1 to 3;
$R^1$ is methoxy; $R^2$ is hydrogen; Z is —NH—;
$R^3$ is halogeno or $C_{1-3}$alkyl; and
$X^1$ is —O—; then
$R^4$ is not selected from one of the following three groups:
a) —$C_{2-5}$alkyl$R^{19}$ (wherein $R^{19}$ is piperidin-4-yl which may bear one or two substituents selected from hydroxy, halogeno, $C_{1-4}$alkyl, $C_{1-4}$hydroxyalkyl and $C_{1-4}$alkoxy);
b) —$C_{2-5}$alkenyl$R^{19}$ (wherein $R^{19}$ is as defined hereinbefore);
c) —$C_{2-5}$alkynyl$R^{19}$ (wherein $R^{19}$ is as defined hereinbefore);

wherein any alkyl, alkenyl or alkynyl group is optionally substituted by one or more substituents selected from hydroxy, halogeno and amino;

or a pharmaceutically-acceptable salt or prodrug thereof.

A further particular class of compounds of the formula (I) wherein:
ring A is phenyl;
m is 1, 2 or 3;
Z is —NH—;
$R^1$, $R^2$ and $R^3$ are as hereinabove defined; $X^1$ is —O—, —S—, —$NR^7CO$—, —$NR^7SO_2$— or —$NR^7$— (wherein $R^7$ is hydrogen, methyl, ethyl or methoxyethyl); and $R^4$ is selected from groups 1c) to 4c) as hereinabove defined;
provided that when:
m is an integer from 1 to 3;
$R^1$ is methoxy; $R^2$ is hydrogen; Z is —NH—;
$R^3$ is halogeno or $C_{1-3}$alkyl; and
$X^1$ is —O—; then
$R^4$ is not selected from one of the following three groups:
a) —$C_{2-5}$alkyl$R^{19}$ (wherein $R^{19}$ is piperidin-4-yl which may bear one or two substituents selected from hydroxy, halogeno, $C_{1-4}$alkyl, $C_{1-4}$hydroxyalkyl and $C_{1-4}$alkoxy);
b) —$C_{2-5}$alkenyl$R^{19}$ (wherein $R^{19}$ is as defined hereinbefore);
c) —$C_{2-5}$alkynyl$R^{19}$ (wherein $R^{19}$ is as defined hereinbefore);

wherein any alkyl, alkenyl or alkynyl group is optionally substituted by one or more substituents selected from hydroxy, halogeno and amino, or a pharmaceutically-acceptable salt or prodrug thereof.

Yet a further particular class of compounds is of the formula (I) wherein:
ring A is phenyl;
m is 1, 2 or 3;
Z is —NH—;
$R^1$, $R^2$ and $R^3$ are as hereinabove defined;
$X^1$ is —O— or —S—; and
$R^4$ is of the formula —$Y^1R^{20}$ or $Y^1NR^{17}R^{18}$ as hereinabove defined;
provided that when:
m is an integer from 1 to 3;
$R^1$ is methoxy; $R^2$ is hydrogen; Z is —NH—;
$R^3$ is halogeno or $C_{1-3}$alkyl; and
$X^1$ is —O—; then
$R^4$ is not selected from one of the following three groups:
a) —$C_{2-5}$alkyl$R^{19}$ (wherein $R^{19}$ is piperidin-4-yl which may bear one or two substituents selected from hydroxy, halogeno, $C_{1-4}$alkyl, $C_{1-4}$hydroxyalkyl and $C_{1-4}$alkoxy);
b) —$C_{2-5}$alkenyl$R^{19}$ (wherein $R^{19}$ is as defined hereinbefore);
c) —$C_{2-5}$alkynyl$R^{19}$ (wherein $R^{19}$ is as defined hereinbefore);

wherein any alkyl, alkenyl or alkynyl group is optionally substituted by one or more substituents selected from hydroxy, halogeno and amino;

or a pharmaceutically-acceptable salt or prodrug thereof.

Yet a further particular class of compounds if of the formula (I) wherein:
ring A is phenyl;
Z is —NH—;
m is 1, 2 or 3;
$R^1$ is hydrogen or methoxy;
$R^2$ is hydrogen;
$R^3$ is fluoro, chloro, bromo, methyl or methoxy;
$X^1$ is —O— or —S—; and
$R^4$ is of the formula —$Y^1$—$R^{20}$ or —$Y^1$—$NR^{17}R^{18}$ (wherein $Y^1$, $R^{17}$, $R^{18}$ and $R^{20}$ are as hereinabove defined;

provided that when:
m is an integer from 1 to 3;
$R^1$ is methoxy; $R^2$ is hydrogen Z is —NH—;
$R^3$ is halogeno or $C_{1-3}$alkyl; and
$X^1$ is —O—; then
$R^4$ is not selected from one of the following three groups:
a) —$C_{2-5}$alkyl$R^{19}$ (wherein $R^{19}$ is piperidin-4-yl which may bear one or two substituents selected from hydroxy, halogeno, $C_{1-4}$alkyl, $C_{1-4}$hydroxyalkyl and $C_{1-4}$alkoxy);
b) —$C_{2-5}$alkenyl$R^{19}$ (wherein $R^{19}$ is as defined hereinbefore);
c) —$C_{2-5}$alkynyl$R^{19}$ (wherein $R^{19}$ is as defined hereinbefore);

wherein any alkyl, alkenyl or alkynyl group is optionally substituted by one or more substituents selected from hydroxy, halogeno and amino;

or a pharmaceutically-acceptable salt or prodrug thereof.
Particular compounds of the present invention include:
4-(4-bromo-2-fluorophenylamino)-7-[2-hydroxy-3-(4-methylpiperazin-1-yl)propoxy]-6-methoxy)quinazoline
4-(4-chloro-2-fluorophenylamino)-7-[2-hydroxy-3-(pyrrolidin-1-yl)propoxy]-6-methoxy)quinazoline
4-(4-chloro-2-fluorophenylamino)-7-[2-hydroxy-3-(4-methylpiperazin-1-yl)propoxy]-6-methoxy)quinazoline
4-(4-chloro-2-fluorophenylamino)-7-(2-hydroxy-3-(morpholino)propoxy)-6-methoxy)quinazoline
4-(4-bromo-2-fluorophenylamino)-7-[2-hydroxy-3-(thiazolidin-3-yl)propoxy]-6-methoxy)quinazoline
4-(4-bromo-2-fluorophenylamino)-7-[2-hydroxy-3-(3-pyrrolin-1-yl)propoxy]-6-methoxyquinazoline
4-(4-bromo-2-fluorophenylamino)-7-[2-hydroxy-3-(4-(2-morpholinoethyl)piperazin-1-yl)propoxy]-6-methoxyquinazoline
4-(4-bromo-2-fluorophenylamino)-7-[2-hydroxy-3-(4-(3-hydroxypropyl)piperazin-1-yl)propoxy]-6-methoxyquinazoline
4-(4-bromo-2-fluorophenylamino)-7-[2-hydroxy-3-(4-(2-hydroxyethyl)piperazin-1-yl)propoxy]-6-methoxyquinazoline
4-(4-bromo-2-fluorophenylamino)-7-[2-hydroxy-3-(1,2,3,6-tetrahydropyridin-1-yl)propoxy]-6-methoxyquinazoline
4-(4-bromo-2-fluorophenylamino)-7-[2-hydroxy-3-(N-tert-butyl-N-methylamino)propoxy]-6-methoxyquinazoline
4-(4-bromo-2-fluorophenylamino)-7-[2-hydroxy-3-(N-isopropyl-N-methylamino)propoxy]-6-methoxyquinazoline hydrochloride
4-(4-bromo-2-fluorophenylamino)-7-[2-hydroxy-3-(N-isobutyl-N-methylamino)propoxy]-6-methoxyquinazoline
4-(4-bromo-2-fluorophenylamino)-7-[2-hydroxy-3-(N-(2-hydroxyethyl)-N-methylamino)propoxy]-6-methoxyquinazoline
4-(4-bromo-2-fluorophenylamino)-7-[2-hydroxy-3-(morpholino)propoxy]-6-methoxyquinazoline
4-(4-bromo-2-fluorophenylamino)-7-(2-hydroxy-3-(N,N-dimethylamino)propoxy]-6-methoxyquinazoline
4-(4-bromo-2-fluorophenylamino)-7-[2-hydroxy-3-(piperidin-1-yl)propoxy]-6-methoxyquinazoline
4-(4-bromo-2-fluorophenylamino)-7-[2-hydroxy-3-(pyrrolidin-1-yl)propoxy]-6-methoxyquinazoline
4-(4-chloro-2-fluorophenylamino)-7-[2-hydroxy-3-(N,N-dimethylamino)propoxy]-6-methoxyquinazoline
4-(4-chloro-2-fluorophenylamino)-7-[2-hydroxy-3-(piperidin-1-yl)propoxy]-6-methoxyquinazoline
4-(4-chloro-2-fluorophenylamino)-7-[2-hydroxy-3-(homopiperidin-1-yl)propoxy]-6-methoxyquinazoline
4-(4-chloro-2-fluorophenylamino)-7-[2-hydroxy-3-(N-(2-hydroxyethyl)-N-methylamino)propoxy]-6-methoxyquinazoline
4-(4-chloro-2-fluorophenylamino)-7-[2-hydroxy-3-(thiazolidin-3-yl) propoxy]-6-methoxyquinazoline
4-(4-chloro-2-fluorophenylamino)-7-[2-hydroxy-3-(3-pyrrolin-1-yl)propoxy]-6-methoxyquinazoline
4-(4-chloro-2-fluorophenylamino)-7-[2-hydroxy-3-(thiomorpholin-4-yl)propoxy]-6-methoxyquinazoline
4-(4-chloro-2-fluorophenylamino)-7-[2-hydroxy-3-(3-hydroxypyrrolidin-1-yl)propoxy]-6-methoxyquinazoline
4-(4-chloro-2-fluorophenylamino)-7-{2-hydroxy-3-[4-(2-morpholinoethyl)piperazin-1-yl]propoxy}-6-methoxyquinazoline
4-(4-chloro-2-fluorophenylamino)-7-{2-hydroxy-3-[4-(3-hydroxypropyl)piperazin-1-yl]propoxy}-6-methoxyquinazoline
4-(4-chloro-2-fluorophenylamino)-7-{2-hydroxy-3-[4-(2-hydroxyethyl)]piperazin-1-yl)propoxy}-6-methoxyquinazoline
4-(4-chloro-2-fluorophenylamino)-7-[2-hydroxy-3-(azetidin-1-yl)propoxy]-6-methoxyquinazoline
4-(4-chloro-2-fluorophenylamino)-7-[2-hydroxy-3-(2,5-dimethyl-3-pyrrolin-1-yl)propoxy]-6-methoxyquinazoline
4-(4-chloro-2-fluorophenylamino)-7-[2-hydroxy-3-(4-methylpiperidin-1-yl)propoxy]-6-methoxyquinazoline
4-(4-chloro-2-fluorophenylamino)-7-[2-hydroxy-3-N-(prop-2-yn-1-yl)-N-methylamino)propoxy]-6-methoxyquinazoline
4-(4-chloro-2-fluorophenylamino)-7-[2-hydroxy-3-(2-methylpyrrolidin-1-yl)propoxy]-6-methoxyquinazoline
4-(4-chloro-2-fluorophenylamino)-7-[2-hydroxy-3-(N-isopropyl-N-ethylamino)propoxy]-6-methoxyquinazoline
4-(4-chloro-2-fluorophenylamino)-7-[2-hydroxy-3-(N-(2-cyanoethyl)-N-methylamino) propoxy]-6-methoxyquinazoline
4-(4-chloro-2-fluorophenylamino)-7-[2-hydroxy-3-(N-isopropyl-N-methylamino)propoxy]-6-methoxyquinazoline
4-(4-chloro-2-fluorophenylamino)-7-[2-hydroxy-3-(N-isobutyl-N-methylamino)propoxy]-6-methoxyquinazoline
4-(4-chloro-2-fluorophenylamino)-7-[2-hydroxy-3-(N-(n-propyl)-N-methylamino)propoxy]-6-methoxyquinazoline; and pharmaceutically-acceptable salts thereof, and additional particular compounds of the present invention are
4-(4-bromo-2-fluorophenylamino)-7-[2-hydroxy-3-(4-pyridylsulphanyl)propoxy]-6-methoxyquinazoline
4-(4-bromo-2-fluorophenylamino)-7-[2-hydroxy-3-(1-methylimidazol-2-ylsulphanyl)propoxy]-6-methoxyquinazoline
4-chloro-2-fluoro-5-hydroxyphenylamino-7-[2-hydroxy-3-(pyrrolidin-1-yl)propoxy]-6-methoxyquinazoline
4-chloro-2-fluoro-5-hydroxyphenylamino-7-(2-acetoxy-3-piperidinopropoxy)-6-methoxyquinazoline
4-bromo-2-fluoro-5-hydroxyphenylamino-7-[2-acetoxy-3-(pyrrolidin-1-yl)propoxy]-6-methoxyquinazoline
4-bromo-2-fluoro-5-hydroxyphenylamino-7-[2-hydroxy-3-(pyrrolidin-1-yl)propoxy]-6-methoxyquinazoline; and pharmaceutically-acceptable salts thereof Preferred compounds of the present invention are
4-(4-bromo-2-fluorophenylamino)-7-[2-hydroxy-3-(4-methylpiperazin-1-yl)propoxy]-6-methoxy)quinazoline
4-(4-chloro-2-fluorophenylamino)-7-[2-hydroxy-3-(pyrrolidin-1-yl)propoxy]-6-methoxy)quinazoline
4-(4-chloro-2-fluorophenylamino)-7-[2-hydroxy-3-(4-methylpiperazin-1-yl)propoxy]-6-methoxy)quinazoline
4-(4-chloro-2-fluorophenylamino)-7-[2-hydroxy-3-(morpholino)propoxy]-6-methoxy) quinazoline
4-(4-bromo-2-fluorophenylamino)-7-[2-hydroxy-3-(thiazolidin-3-yl)propoxy]-6-methoxy)quinazoline
4-(4-bromo-2-fluorophenylamino)-7-[2-hydroxy-3-(3-pyrrolin-1-yl)propoxy]-6-methoxyquinazoline
4-(4-bromo-2-fluorophenylamino)-7-[2-hydroxy-3-(4-(2-morpholinoethyl)piperazin-1-yl)propoxy]-6-methoxyquinazoline
4-(4-bromo-2-fluorophenylamino)-7-[2-hydroxy-3-(4-(3-hydroxypropyl)piperazin-1-yl)propoxy]-6-methoxyquinazoline
4-(4-bromo-2-fluorophenylamino)-7-[2-hydroxy-3-(4-(2-hydroxyethyl)piperazin-1-yl)propoxy]-6-methoxyquinazoline
4-(4-bromo-2-fluorophenylamino)-7-[2-hydroxy-3-(1,2,3,6-tetrahydropyridin-1-yl)propoxy]-6-methoxyquinazoline
4-(4-bromo-2-fluorophenylamino)-7-[2-hydroxy-3-(N-tert-butyl-N-methylamino)propoxy]-6-methoxyquinazoline
4-(4-bromo-2-fluorophenylamino)-7-[2-hydroxy-3-(N-isopropyl-N-methylamino)propoxy]-6-methoxyquinazoline hydrochloride
4-(4-bromo-2-fluorophenylamino)-7-[2-hydroxy-3-(N-isobutyl-N-methylamino)propoxy]-6-methoxyquinazoline
4-(4-bromo-2-fluorophenyl amino)-7-[2-hydroxy-3-(N-(2-hydroxyethyl)-N-methylamino)propoxy]-6-methoxyquinazoline
4-(4-bromo-2-fluorophenylamino)-7-[2-hydroxy-3-(morpholino)propoxy]-6-methoxyquinazoline
4-(4-bromo-2-fluorophenylamino)-7-(2-hydroxy-3-(N,N-dimethylamino)propoxy]-6-methoxyquinazoline
4-(4-bromo-2-fluorophenylamino)-7-[2-hydroxy-3-(piperidin-1-yl)propoxy]-6-methoxyquinazoline
4-(4-bromo-2-fluorophenylamino)-7-[2-hydroxy-3-(pyrrolidin-1-yl)propoxy]-6-methoxyquinazoline
4-(4-chloro-2-fluorophenylamino)-7-[2-hydroxy-3-(N,N-dimethylamino)propoxy]-6-methoxyquinazoline
4-(4-chloro-2-fluorophenylamino)-7-[2-hydroxy-3-(piperidin-1-yl)propoxy]-6-methoxyquinazoline
4-(4-chloro-2-fluorophenylamino)-7-[2-hydroxy-3-(homopiperidin-1-yl)propoxy]-6-methoxyquinazoline
4-(4-chloro-2-fluorophenylamino)-7-[2-hydroxy-3-(N-(2-hydroxyethyl)-N-methylamino)propoxy]-6-methoxyquinazoline
4-(4-chloro-2-fluorophenylamino)-7-[2-hydroxy-3-(3-pyrrolin-1-yl)propoxy]-6-methoxyquinazoline
4-(4-chloro-2-fluorophenylamino)-7-[2-hydroxy-3-(thiomorpholin-4-yl)propoxy]-6-methoxyquinazoline
4-(4-chloro-2-fluorophenylamino)-7-[2-hydroxy-3-(3-hydroxypyrrolidin-1-yl)propoxy]-6-methoxyquinazoline
4-(4-chloro-2-fluorophenylamino)-7-{2-hydroxy-3-[4-(2-morpholinoethyl)piperazin-1-yl]propoxy}-6-methoxyquinazoline
4-(4-chloro-2-fluorophenylamino)-7-{2-hydroxy-3-[4-(2-hydroxyethyl)]piperazin-1-yl)propoxy}-6-methoxyquinazoline
4-(4-chloro-2-fluorophenylamino)-7-[2-hydroxy-3-(2,5-dimethyl-3-pyrrolin-1-yl)propoxy]-6-methoxyquinazoline
4-(4-chloro-2-fluorophenylamino)-7-[2-hydroxy-3-(4-methylpiperidin-1-yl)propoxy]-6-methoxyquinazoline
4-(4-chloro-2-fluorophenylamino)-7-[2-hydroxy-3-(2-methylpyrrolidin-1-yl)propoxy]-6-methoxyquinazoline
4-(4-chloro-2-fluorophenylamino)-7-[2-hydroxy-3-(N-(2-cyanoethyl)-N-methylamino)propoxy]-6-methoxyquinazoline
4-(4-chloro-2-fluorophenylamino)-7-[2-hydroxy-3-(N-isopropyl-N-methylamino)propoxy]-6-methoxyquinazoline
4-(4-chloro-2-fluorophenylamino)-7-[2-hydroxy-3-(N-isobutyl-N-methylamino)propoxy]-6-methoxyquinazoline
4-chloro-2-fluoro-5-hydroxyphenylamino-7-[2-hydroxy-3-(pyrrolidin-1-yl)propoxy]-6-methoxyquinazoline
4-chloro-2-fluoro-5-hydroxyphenylamino-7-(2-acetoxy-3-piperidinopropoxy)-6-methoxyquinazoline
4-bromo-2-fluoro-5-hydroxyphenylamino-7-[2-acetoxy-3-(pyrrolidin-1-yl)propoxy]-6-methoxyquinazoline
4-bromo-2-fluoro-5-hydroxyphenylamino-7-[2-hydroxy-3-(pyrrolidin-1-yl)propoxy]-6-methoxyquinazoline; and pharmaceutically-acceptable salts thereof.

The present invention relates to the compounds of formula I as hereinbefore defined as well as to the salts thereof. Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

Various forms of prodrugs are well known in the art. For examples of such prodrug derivatives, see:
a) Design of Prodrugs, edited by H. Bundgaard, (Elsevier, 1985) and Methods in Enzymology, Vol. 42, p. 309–396, edited by K. Widder, et al. (Academic Press, 1985);
b) A Textbook of Drug Design and Development, edited by Krogsgaard-Larsen and H. Bundgaard, Chapter 5 "Design and Application of Prodrugs", by H. Bundgaard p. 113–191 (1991);
c) H. Bundgaard, Advanced Drug Delivery Reviews, 8, 1–38 (1992);
d) H. Bundgaard, et al., Journal of Pharmaceutical Sciences, 77, 285 (1988); and
e) N. Kakeya, et al., Chem Pharm Bull, 32, 692 (1984).

An example of a prodrug is an in vivo hydrolysable ester formed at a hydroxy group. The term includes inorganic esters such as phosphate esters and α-acyloxyalkyl ethers and related compounds which as a result of the in vivo hydrolysis of the ester breakdown to give the parent hydroxy group. Examples of α-acyloxyalkyl ethers include acetoxymethoxy and 2,2-dimethylpropionyloxymethoxy. A selection of in vivo hydrolysable ester forming groups for hydroxy include alkanoyl, benzoyl, phenylacetyl and substituted benzoyl and phenylacetyl, alkoxycarbonyl (to give alkyl carbonate esters), dialkylcarbamoyl and N-(dialkylaminoethyl)-N-alkylcarbamoyl (to give carbamates), dialkylaminoacetyl and carboxyacetyl.

A compound of the formula I, or salt thereof, and other compounds of the invention (as hereinafter defined) may be prepared by any process known to be applicable to the preparation of chemically-related compounds. Such processes include, for example, those illustrated in European Patent Applications, Publication Nos. 0520722, 0566226, 0602851, 0635498, 0873319, 0880508 and 0929530. Such processes, are provided as a further feature of the invention and are as described hereinafter. Necessary starting materials may be obtained by standard procedures of organic chemistry. The preparation of such starting materials is described within the accompanying non-limiting Examples. Alternatively necessary starting materials are obtainable by analogous procedures to those illustrated which are within the ordinary skill of an organic chemist.

Thus the following processes (a) to (f) and (i) to (vi) constitute further features of the present invention.

Synthesis of Compounds of Formula I (a) Compounds of the formula I and salts thereof may be prepared by the reaction of a compound of the formula III:

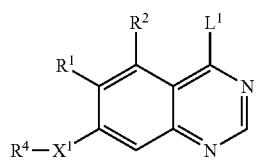

(III)

(wherein $R^1$, $R^2$, $X^1$ and $R^4$ are as defined hereinbefore and $L^1$ is a displaceable moiety), with a compound of the formula IV:

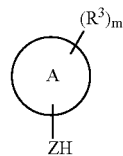

(IV)

(wherein ring A, Z, $R^3$ and m are as defined hereinbefore) whereby to obtain compounds of the formula I and salts thereof. A convenient displaceable moiety $L^1$ is, for example, a halogeno, alkoxy (preferably $C_{1-4}$alkoxy), aryloxy, alkylsulphanyl, arylsulphanyl, alkoxyalkylsulphanyl or sulphonyloxy group, for example a chloro, bromo, methoxy, phenoxy, methylsulphanyl, 2-methoxyethylsulphanyl, methanesulphonyloxy or toluene-4-sulphonyloxy group.

The reaction is advantageously effected in the presence of either an acid or a base. Such an acid is, for example, an anhydrous inorganic acid such as hydrogen chloride. Such a base is, for example, an organic amine base such as, for example, pyridine, 2,6-lutidine, collidine, 4-dimethylaminopyridine, triethylamine, tetramethylguanidine, morpholine, N-methylmorpholine or diazabicyclo[5,4.0]undec-7-ene, or for example, an alkali metal or alkaline earth metal carbonate or hydroxide, for example sodium carbonate, potassium carbonate, calcium carbonate, sodium hydroxide or potassium hydroxide. Alternatively such a base is, for example, an alkali metal hydride, for example sodium hydride, or an alkali metal or alkaline earth metal amide, for example sodium amide, sodium bis(trimethylsilyl)amide, potassium amide or potassium bis(trimethylsilyl)amide. The reaction is preferably effected in the presence of an inert solvent or diluent, for example an alkanol or ester such as methanol, ethanol, isopropanol or ethyl acetate, a halogenated solvent such as methylene chloride, trichloromethane or carbon tetrachloride, an ether such as tetrahydrofuran or 1,4-dioxan, an aromatic hydrocarbon solvent such as toluene, or a dipolar aprotic solvent such as N,N-dimethylformamide, N,N-dimethylacetamide, N-methylpyrrolidin-2-one or dimethylsulphoxide. Preferably, when ring a is heterocyclic a base is used. The reaction is conveniently effected at a temperature in the range, for example, 10 to 150° C., preferably in the range 20 to 80° C.

The compound of the invention may be obtained from this process in the form of the free base or alternatively it may be obtained in the form of a salt with the acid of the formula H-$L^1$ wherein $L^1$ has the meaning defined hereinbefore. When it is desired to obtain the free base from the salt, the salt may be treated with a base as defined hereinbefore using a conventional procedure.

(b) Where the group of formula IIa:

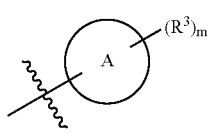

(IIa)

(wherein ring A, $R^3$ and m are as hereinbefore defined) is a ring carrying one or more hydroxy groups, a compound of the formula I and salts thereof can be prepared by the deprotection of a compound of formula V

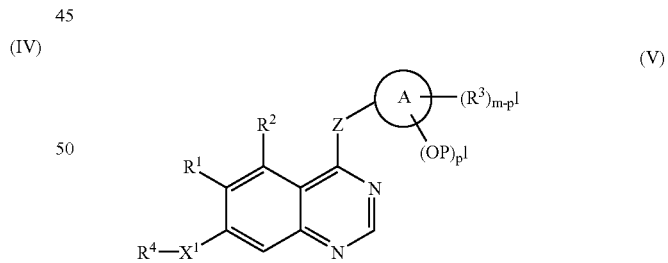

(V)

(wherein ring A, $X^1$, m, $R^1$, $R^2$, $R^3$, $R^4$ and Z are as hereinbefore defined, P is a hydroxy protecting group and $p^1$ is an integer from 1 to 5 equal to the number of protected hydroxy groups and such that m-$p^1$ is equal to the number of $R^3$ substituents which are not protected hydroxy). The choice of hydroxy protecting group P is within the standard knowledge of an organic chemist, for example those included in standard texts such as "Protective Groups in Organic Synthesis" T. W. Greene and R. G. M. Wuts, 2nd Ed. Wiley 1991, including ethers (for example, methyl, methoxymethyl, allyl and benzyl), silyl ethers (for example, t-butyldiphenylsilyl and t-butyldimethylsilyl), esters (for example, acetate and benzoate) and carbonates (for example, methyl and benzyl). The removal of such a hydroxy protecting group may be effected by any of the procedures known for such a transformation, including those reaction conditions indicated in standard texts such as that indicated hereinbefore, or by a related procedure. The reaction conditions preferably being such that the hydroxy derivative is produced without unwanted reactions at other sites within the starting or product compounds. For example, where the protecting group P is acetate, the transformation may conveniently be effected by treatment of the quinazoline derivative with a base as defined hereinbefore and including ammonia, and its mono and di-alkylated derivatives, preferably in the presence of a protic solvent or co-solvent such as water or an alcohol, for example methanol or ethanol. Such a reaction can be effected in the presence of an additional inert solvent or diluent as defined hereinbefore and at a temperature in the range 0 to 50° C., conveniently at about 20° C.

(c) Production of those compounds of formula I and salts thereof wherein the substituent $X^1$ is —O—, —S— or —NR$^7$— can be achieved by the reaction, conveniently in the presence of a base as defined hereinbefore, of a compound of the formula VI:

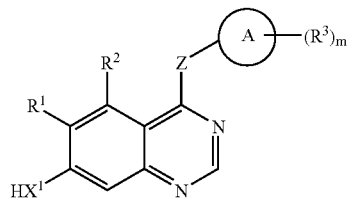

(VI)

(wherein ring A, m, $X^1$, $R^1$, $R^2$, $R^3$, and Z are as hereinbefore defined) with a compound of formula VII:

$$R^4\text{-}L^1 \qquad (VII)$$

(wherein $R^4$ and $L^1$ are as hereinbefore defined); $L^1$ is a displaceable moiety for example a halogeno or sulphonyloxy group such as a bromo or methanesulphonyloxy group. The reaction is preferably effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 50° C.

(d) Compounds of the formula I and salts thereof may be prepared by the reaction of a compound of the formula VIII:

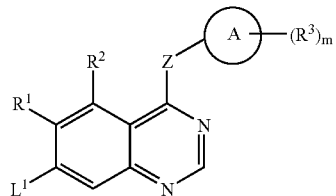

(VIII)

with a compound of the formula IX:

$$R^4\text{—}X^1\text{—}H \qquad (IX)$$

(wherein ring A, $L^1$, $R^1$, $R^2$, $R^3$, $R^4$, Z, m and $X^1$ are all as hereinbefore defined). The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

e) Compounds of the formula (I) and salts thereof wherein $R^4$ is a 2-hydroxypropyl chain substituted by —NR$^{17}$R$^{18}$ (wherein $R^{17}$ and $R^{18}$ are as hereinabove defined) or a saturated or partially saturated heterocyclic ring containing and linked through a ring nitrogen atom and containing up to 2 additional ring heteroatoms selected from O, S and N, by reacting a compound of the formula X:

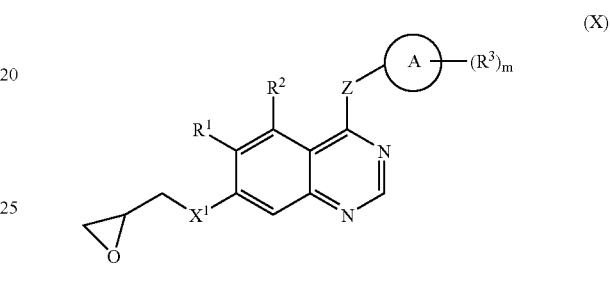

(X)

(wherein ring A, $R^1$, $R^2$, $R^3$, Z, m and $X^1$ are all as hereinbefore defined) with the appropriate amine. The reaction is conveniently carried out in an inert organic solvent such as ethanol or chloroform in a temperature range of 0° C. to 100° C. Analagous reactions may be used to produce compounds of the formula (1) wherein $R^4$ comprises longer hydroxy-substituted alkylene, alkenylene or alkynylene chains.

f) Compounds of the formula (I) and salts thereof wherein the group in $R^4$ linked to —Y$^1$— or —Y$^2$— is linked via a N, O or S atom may be prepared by reacting a compound of the formula (XI):

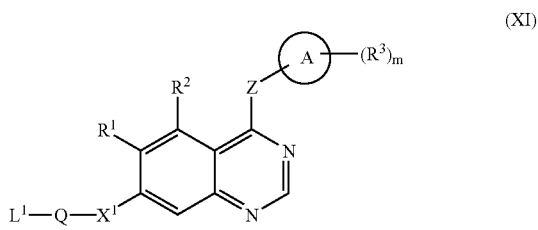

(XI)

(wherein ring A, $L^1$, $X^1$, $R^1$, $R^2$, $R^3$, Z and m are as hereinabove defined and Q is —Y$^1$— or —Y$^2$—) with the appropriate compound containing a HN, HO or HS group. The reaction is conveniently carried out in the presence of a base (as hereinabove defined in process (a)) in the presence of an inert organic solvent (as defined in process (a)), in a temperature range of 0° C. to 150° C.

Synthesis of Intermediates (i) The compounds of formula III and salts thereof, constitute a further feature of the present invention. Such compounds in which $L^1$ is halogeno may for example be prepared by halogenating a compound of the formula XII:

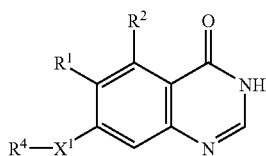

(XII)

(wherein $R^1$, $R^2$, $R^4$ and $X^1$ are as hereinbefore defined).

Convenient halogenating agents include inorganic acid halides, for example thionyl chloride, phosphorus(III)chloride, phosphorus(V)oxychloride and phosphorus(V)chloride. The halogenation reaction is conveniently effected in the presence of an inert solvent or diluent such as for example a halogenated solvent such as methylene chloride, trichloromethane or carbon tetrachloride, or an aromatic hydrocarbon solvent such as benzene or toluene. The reaction is conveniently effected at a temperature in the range, for example 10 to 150° C., preferably in the range 40 to 100° C.

The compounds of formula XII and salts thereof which constitute a further feature of the present invention may for example be prepared by reacting a compound of the formula XIII:

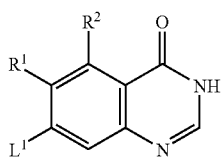

(XIII)

(wherein $R^1$, $R^2$ and $L^1$ are as hereinbefore defined) with a compound of the formula IX as hereinbefore defined. The reaction may conveniently be effected in the presence of a base (as defined hereinbefore in process (a)) and advantageously in the presence of an inert solvent or diluent (as defined hereinbefore in process (a)), advantageously at a temperature in the range, for example 10 to 150° C., conveniently at about 100° C.

The compounds of formula XII and salts thereof may also be prepared by cyclising a compound of the formula XIV:

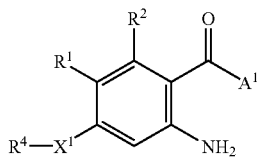

(XIV)

(wherein $R^1$, $R^2$, $R^4$ and $X^1$, are as hereinbefore defined, and $A^1$ is an hydroxy, alkoxy (preferably $C_{1-4}$alkoxy) or amino group) whereby to form a compound of formula XII or salt thereof. The cyclisation may be effected by reacting a compound of the formula XIV, where $A^1$ is an hydroxy or alkoxy group, with formamide or an equivalent thereof effective to cause cyclisation whereby a compound of formula XII or salt thereof is obtained, such as [3-(dimethylamino)-2-azaprop-2-enylidene]dimethylammonium chloride. The cyclisation is conveniently effected in the presence of formamide as solvent or in the presence of an inert solvent or diluent such as an ether for example 1,4-dioxan. The cyclisation is conveniently effected at an elevated temperature, preferably in the range 80 to 200° C. The compounds of formula XII may also be prepared by cyclising a compound of the formula XIV, where $A^1$ is an amino group, with formic acid or an equivalent thereof effective to cause cyclisation whereby a compound of formula XII or salt thereof is obtained. Equivalents of formic acid effective to cause cyclisation include for example a tri-$C_{1-4}$ alkoxymethane, for example triethoxymethane and trimethoxymethane. The cyclisation is conveniently effected in the presence of a catalytic amount of an anhydrous acid, such as a sulphonic acid for example p-toluenesulphonic acid, and in the presence of an inert solvent or diluent such as for example a halogenated solvent such as methylene chloride, trichloromethane or carbon tetrachloride, an ether such as diethylether or tetrahydrofuran, or an aromatic hydrocarbon solvent such as toluene. The cyclisation is conveniently effected at a temperature in the range, for example 10 to 100° C., preferably in the range 20 to 50° C.

Compounds of formula XIV and salts thereof, which constitute a further feature of the present invention, may for example be prepared by the reduction of the nitro group in a compound of the formula XV:

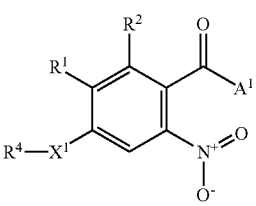

(XV)

(wherein $R^1$, $R^2$, $R^4$, $X^1$ and $A^1$ are as hereinbefore defined) to yield a compound of formula XIV as hereinbefore defined. The reduction of the nitro group may conveniently be effected by any of the procedures known for such a transformation. The reduction may be carried out, for example, by the hydrogenation of a solution of the nitro compound in the presence of an inert solvent or diluent as defined hereinbefore in the presence of a metal effective to catalyse hydrogenation reactions such as palladium or platinum. A further reducing agent is, for example, an activated metal such as activated iron (produced for example by washing iron powder with a dilute solution of an acid such as hydrochloric acid). Thus, for example, the reduction may be effected by heating the nitro compound and the activated metal in the presence of a solvent or diluent such as a mixture of water and alcohol, for example methanol or ethanol, to a temperature in the range, for example 50 to 150° C., conveniently at about 70° C.

Compounds of the formula XV and salts thereof which constitute a further feature of the present invention, may for example be prepared by the reaction of a compound of the formula XVI:

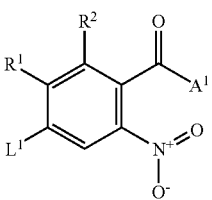

(XVI)

(wherein $R^1$, $R^2$, $L^1$ and $A^1$ are as hereinbefore defined) with a compound of the formula IX as hereinbefore defined to give a compound of the formual XV. The reaction of the compounds of formulae XVI and IX is conveniently effected under conditions as described for process (d) hereinbefore.

Compounds of formula XV and salts thereof, may for example also be prepared by the reaction of a compound of the formula XVII:

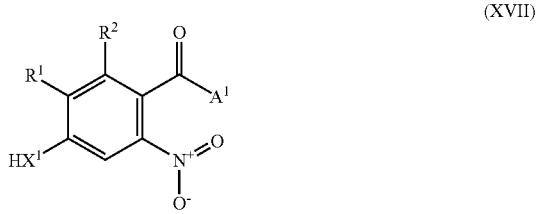

(XVII)

(wherein $R^1$, $R^2$, $X^1$ and $A^1$ are as hereinbefore defined with the proviso that $X^1$ is not —$CH_2$—) with a compound of the formula VII as hereinbefore defined to yield a compound of formula XV as hereinbefore defined. The reaction of the compounds of formulae XVII and VII is conveniently effected under conditions as described for process (c) hereinbefore.

The compounds of formula III and salts thereof may also be prepared for example by reacting a compound of the formula XVIII:

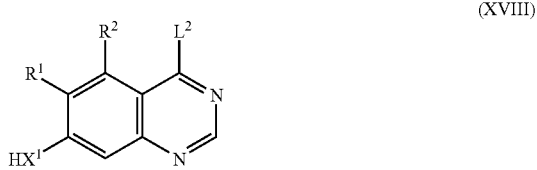

(XVIII)

(wherein $R^1$, $R^2$ and $X^1$ are as hereinbefore defined with the proviso that $X^1$ is not —$CH_2$— and $L^2$ is a displaceable protecting moiety) with a compound of the formula VII as hereinbefore defined, whereby to obtain a compound of formula III in which $L^1$ is represented by $L^2$.

A compound of formula XVIII is conveniently used in which $L^2$ is a phenoxy group which may if desired carry up to 5 substituents, preferably up to 2 substituents, selected from halogeno, nitro and cyano. The reaction may be conveniently effected under conditions as described for process (c) hereinbefore.

The compounds of formula XVIII and salts thereof as hereinbefore defined may for example be prepared by deprotecting a compound of the formula XIX:

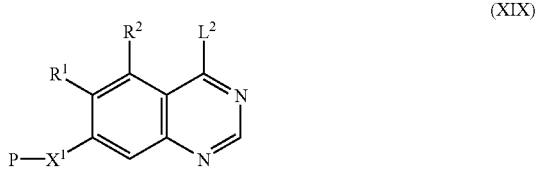

(XIX)

(wherein $R^1$, $R^2$, P, $X^1$ and $L^2$ are as hereinbefore defined with the proviso that $X^1$ is not —$CH_2$—). Deprotection may be effected by techniques well known in the literature, for example where P is a benzyl group deprotection may be effected by hydrogenolysis or by treatment with trifluoroacetic acid.

One compound of formula III may if desired be converted into another compound of formula III in which the moiety $L^1$ is different. Thus for example a compound of formula III in which $L^1$ is other than halogeno, for example optionally substituted phenoxy, may be converted to a compound of formula III in which $L^1$ is halogeno by hydrolysis of a compound of formula III (in which $L^1$ is other than halogeno) to yield a compound of formula XII as hereinbefore defined, followed by introduction of halide to the compound of formula XII, thus obtained as hereinbefore defined, to yield a compound of formula III in which $L^1$ is halogen.

(ii) The compounds of formula V and salts thereof, constitute a further feature of the present invention, and may for example be prepared by the reaction of a compound of formula III as hereinbefore defined with a compound of the formula XX:

(XX)

(wherein ring A, $R^3$, m, $p^1$, P and Z are as hereinbefore defined). The reaction may for example be effected as described for process (a) hereinbefore.

The compounds of formula V and salts thereof may also be prepared by reacting a compound of formula XXI:

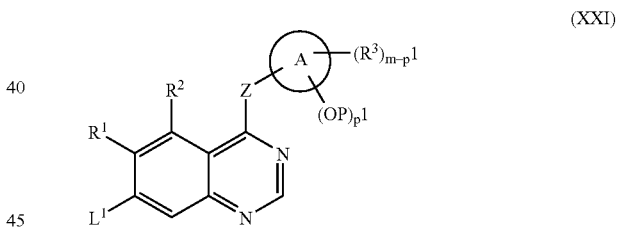

(XXI)

(wherein ring A, $R^1$, $R^2$, $L^1$, Z, $R^3$, m, $p^1$ and P are as hereinbefore defined) with a compound of formula IX as hereinbefore defined. The reaction may for example be effected as described for process (d) above.

The compounds of formula V and salts thereof may also be prepared by reacting a compound of formula XXII:

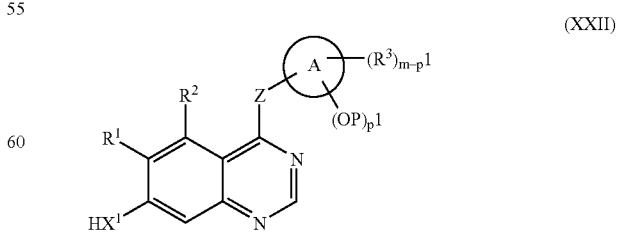

(XXII)

(wherein ring A, $R^1$, $R^2$, $R^3$, $X^1$, Z, P, $p^1$ and m are as hereinbefore defined with the proviso that $X^1$ is not —CH$_2$—) with a compound of the formula VII as hereinbefore defined. The reaction may for example be effected as described for process (c) hereinbefore.

The compounds of formula XXI and salts thereof may for example be prepared by reaction of a compound of formula XXIII:

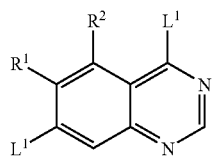

(XXIII)

(wherein R$^1$, R$^2$, and L$^1$ are as hereinbefore defined, and L$^1$ in the 4- and 7-positions may be the same or different) with a compound of the formula XX as hereinbefore defined. The reaction may be effected for example by a process as described in (a) above.

Compounds of the formula XXII and salts thereof may be made by reacting compounds of the formulae XIX and XX as hereinbefore defined, under conditions described in (a) hereinbefore, to give a compound of formula XXIV:

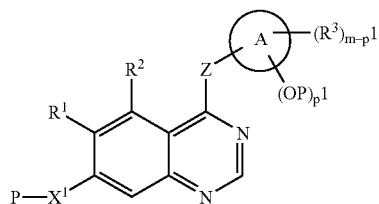

(XXIV)

(wherein ring A, R$^1$, R$^2$, R$^3$, P, Z, X$^1$, p$^1$ and m are as hereinbefore defined with the proviso that X$^1$ is not —CH$_2$—) and then deprotecting the compound of formula XXIV for example as described in (i) above.

(iii) Compounds of the formula VI as hereinbefore defined and salts thereof may be made by deprotecting the compound of formula XXV:

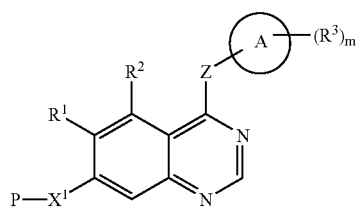

(XXV)

(wherein ring A, R$^1$, R$^2$, R$^3$, P, Z, X$^1$ and m are as hereinbefore defined) by a process for example as described in (i) above.

Compounds of the formula XXV and salts thereof may be made by reacting compounds of the formulae XIX and IV as hereinbefore defined, under the conditions described in (a) hereinbefore, to give a compound of the formula XXV or salt thereof.

(iv) Compounds of the formula VIII and salts thereof as hereinbefore defined may be made by reacting compounds of the formulae XXIII and IV as hereinbefore defined, the reaction for example being effected by a process as described in (a) above.

(v) Compounds of the formula (X) can be prepared by reacting the appropriate epoxy compound substituted with a leaving group such as halo (for example in the case of Y$^1$ or Y$^2$ being 2,3-epoxyprop-1-yl, 1-bromo-2,3-epoxyprepane may be used) with a compound of the formula (XXV) (for example the 7-hydroxyquinazoline derivative). The reaction is conveniently carried out in the presence of a mild base such as metal carbonate (e.g potassium carbonate).

(vi) Compounds of the formula XI as defined hereinbefore and salts thereof may for example be made by the reaction of a compound of formula VI as defined hereinbefore with a compound of the formula XXVI:

L$^1$-Q-L$^1$ (XXVI)

(wherein L$^1$ and Q are as hereinbefore defined) to give a compound of the formula XI. The reaction may be effected for example by a process as described in (c) above.

Compounds of the formula XI and salts thereof may also be made for example by deprotecting a compound of the formula XXVII:

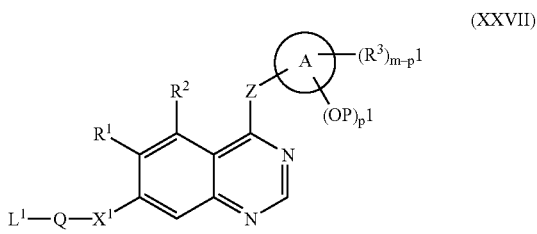

(XXVII)

(wherein ring A, L$^1$, Q, X$^1$, R$^1$, R$^2$, R$^3$, Z, P, m and p$^1$ are as defined hereinbefore) by a process for example as described in (b) above.

Compounds of the formula XXVII and salts thereof may be made for example by reacting compounds of the formulae XXII and XXVI as defined hereinbefore, under the conditions described in (c) above.

When a pharmaceutically acceptable salt of a compound of the formula I is required, it may be obtained, for example, by reaction of said compound with, for example, an acid using a conventional procedure, the acid having a pharmaceutically acceptable anion.

Some of the intermediates defined herein are novel, for example, those of the formulae V and X and these are provided as a further feature of the invention. Optional substituents may be converted into other optional substituents. For example an alkylthio group may be oxidised to an alkylsulphinyl or alkylsulphonyl group, a nitro group reduced to an amino group, a hydroxy group alkylated to a methoxy group, or a bromo group converted to an alkylthio group.

Various substituents may be introduced into compounds of the formulae (I) and intermediates in the preparation of the formulae (I) and intermediates in the preparation of compounds of the formulae (I), when appropriate, using standard methods known in the art. For example, a nitro group may be introduced into an activated benzene ring by nitration with concentrated nitric acid concentrated sulphuric acid and bromination with bromine or tetra (n-butyl) ammonium tribromide.

It will be appreciated that, in certain steps in the reaction sequence to compounds of the formula (I), it will be necessary to protect certain functional groups in intermediates in order to prevent side reactions. Deprotection may be carried out at a convenient stage in the reaction sequence once protection is no longer required.

Protecting groups may in general be chosen from any of the groups described in the literature or known to the skilled chemist as appropriate for the protection of the group in question and may be introduced by conventional methods. Protecting groups may be removed by any convenient method as described in the literature or known to the skilled chemist as appropriate for the removal of the protecting group in question, such methods being chosen so as to effect removal of the protecting group with minimum disturbance of groups elsewhere in the molecule.

Specific examples of protecting groups are given below for the sake of convenience, in which "lower", as in, for example, lower alkyl, signifies that the group to which it is applied preferably has 1–4 carbon atoms. It will be understood that these examples are not exhaustive.

Where specific examples of methods for the removal of protecting groups are given below these are similarly not exhaustive. The use of protecting groups and methods of deprotection not specifically mentioned are, of course, within the scope of the invention.

A carboxy protecting group may be the residue of an ester-forming aliphatic or arylaliphatic alcohol or of an ester-forming silanol (the said alcohol or silanol preferably containing 1–20 carbon atoms). Examples of carboxy protecting groups include straight or branched chain (1–12C) alkyl groups (for example isopropyl, and tert-butyl); lower alkoxy-lower alkyl groups (for example methoxymethyl, ethoxymethyl and isobutoxymethyl); lower acyloxy-lower alkyl groups, (for example acetoxymethyl, propionyloxymethyl, butyryloxymethyl and pivaloyloxymethyl); lower alkoxycarbonyloxy-lower alkyl groups (for example 1-methoxycarbonyloxyethyl and 1-ethoxycarbonyloxyethyl); aryl-lower alkyl groups (for example benzyl, 4-methoxybenzyl, 2-nitrobenzyl, 4-nitrobenzyl, benzhydryl and phthalidyl); tri(lower alkyl)silyl groups (for example trimethylsilyl and tert-butyldimethylsilyl); tri(lower alkyl)silyl-lower alkyl groups (for example trimethylsilylethyl); and (2–6C)alkenyl groups (for example allyl). Methods particularly appropriate for the removal of carboxyl protecting groups include for example acid-, base-, metal- or enzymically-catalysed cleavage.

Examples of hydroxy protecting groups include lower alkyl groups (for example tert-butyl), lower alkenyl groups (for example allyl); lower alkanoyl groups (for example acetyl); lower alkoxycarbonyl groups (for example tert-butoxycarbonyl); lower alkenyloxycarbonyl groups (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); tri(lower alkyl)silyl (for example trimethylsilyl and tert-butyldimethylsilyl) and aryl-lower alkyl (for example benzyl) groups.

Examples of amino protecting groups include formyl, aryl-lower alkyl groups (for example benzyl and substituted benzyl, 4-methoxybenzyl, 2-nitrobenzyl and 2,4-dimethoxybenzyl, and triphenylmethyl); di-4-anisylmethyl and furylmethyl groups; lower alkoxycarbonyl (for example tert-butoxycarbonyl); lower alkenyloxycarbonyl (for example allyloxycarbonyl); aryl-lower alkoxycarbonyl groups (for example benzyloxycarbonyl, 4-methoxybenzyloxycarbonyl, 2-nitrobenzyloxycarbonyl and 4-nitrobenzyloxycarbonyl); trialkylsilyl (for example trimethylsilyl and tert-butyldimethylsilyl); alkylidene (for example methylidene) and benzylidene and substituted benzylidene groups.

Methods appropriate for removal of hydroxy and amino protecting groups include, for example, acid-, base-, metal- or enzymically-catalysed hydrolysis for groups such as 2-nitrobenzyloxycarbonyl, hydrogenation for groups such as benzyl and photolytically for groups such as 2-nitrobenzyloxycarbonyl.

The reader is referred to 'Advanced Organic Chemistry', 4th Edition, by J. March, published by John Wiley & Sons 1992, for general guidance on reaction conditions and reagents and to 'Protective Groups in Organic Synthesis', $2^{nd}$ Edition, by T. Greene and R. G. M. Wuts, for general guidance on protecting groups.

The identification of compounds which potently inhibit the tyrosine kinase activity associated with VEGF receptors such as Flt and/or KDR and which inhibit angiogenesis and/or increased vascular permeability is desirable and is the subject of the present invention. These properties may be assessed, for example, using one or more of the procedures set out below:

(a) In vitro Receptor Tyrosine Kinase Inhibition Test

This assay determines the ability of a test compound to inhibit tyrosine kinase activity. DNA encoding VEGF, FGF or EGF receptor cytoplasmic domains may be obtained by total gene synthesis (Edwards M, International Biotechnology Lab 5(3), 19–25, 1987) or by cloning. These may then be expressed in a suitable expression system to obtain polypeptide with tyrosine kinase activity. For example VEGF, FGF and EGF receptor cytoplasmic domains, which were obtained by expression of recombinant protein in insect cells, were found to display intrinsic tyrosine kinase activity. In the case of the VEGF receptor Flt (Genbank accession number X51602), a 7 kb DNA fragment encoding most of the cytoplasmic domain, commencing with methionine 783 and including the termination codon, described by Shibuya et al (Oncogene, 1990, 5: 519–524), was isolated from cDNA and cloned into a baculovirus transplacement vector (for example pAcYM1 (see The Baculovirus Expression System: A Laboratory Guide, L. A. King and R. D. Possee, Chapman and Hall, 1992) or pAc360 or pBlueBacHis (available from Invitrogen Corporation)). This recombinant construct was co-transfected into insect cells (for example *Spodoptera frugiperda* 21(Sf21)) with viral DNA (eg Pharmingen BaculoGold) to prepare recombinant baculovirus. (Details of the methods for the assembly of recombinant DNA molecules and the preparation and use of recombinant baculovirus can be found in standard texts for example Sambrook et al, 1989, Molecular cloning—A Laboratory Manual, 2nd edition, Cold Spring Harbour Laboratory Press and O'Reilly et al, 1992, Baculovirus Expression Vectors—A Laboratory Manual, W. H. Freeman and Co, New York). For other tyrosine kinases for use in assays, cytoplasmic fragments starting from methionine 806 (KDR, Genbank accession number L04947), methionine 668 (EGF receptor, Genbank accession number X00588) and methionine 399 (FGF $R^1$ receptor, Genbank accession number X51803) may be cloned and expressed in a similar manner.

For expression of cFlt tyrosine kinase activity, Sf21 cells were infected with plaque-pure cFlt recombinant virus at a multiplicity of infection of 3 and harvested 48 hours later. Harvested cells were washed with ice cold phosphate buffered saline solution (PBS) (10 mM sodium phosphate pH 7.4, 138 mM sodium chloride, 2.7 mM potassium chloride) then resuspended in ice cold HNTG/PMSF (20 mM Hepes pH 7.5, 150mM sodium chloride, 10% v/v glycerol, 1% v/v Triton X100, 1.5 mM magnesium chloride, 1 mM ethylene glycol-bis(βaminoethyl ether) N,N,N',N'-tetraacetic acid (EGTA), 1 mM PMSF (phenylmethylsulphonyl fluoride); the PMSF is added just before use from a freshly-prepared 100 mM solution in methanol) using 1 ml HNTG/PMSF per 10 million cells. The suspension was centrifuged for 10 minutes at 13,000 rpm at 4° C., the supernatant (enzyme stock) was removed and stored in aliquots at −70° C. Each new batch of stock enzyme was titrated in the assay by dilution with enzyme diluent (100 mM Hepes pH 7.4, 0.2 mM sodium orthovanadate, 0.1% v/v Triton X100, 02 mM dithiothreitol) For a typical batch, stock enzyme is diluted 1 in 2000 with enzyme diluent and 50 µl of dilute enzyme is used for each assay well.

A stock of substrate solution was prepared from a random copolymer containing tyrosine, for example Poly (Glu, Ala, Tyr) 6:3:1 (Sigma P3899), stored as 1 mg/ml stock in PBS at −20° C. and diluted 1 in 500 with PBS for plate coating.

On the day before the assay 100 µl of diluted substrate solution was dispensed into all wells of assay plates (Nunc maxisorp 96-well immunoplates) which were sealed and left overnight at 4° C.

On the day of the assay the substrate solution was discarded and the assay plate wells were washed once with PBST (PBS containing 0.05% v/v Tween 20) and once with 50 mM Hepes pH 7.4.

Test compounds were diluted with 10% dimethylsulphoxide (DMSO) and 25 µl of diluted compound was transferred to wells in the washed assay plates. "Total" control wells contained 10% DMSO instead of compound. Twenty five microlitres of 40 mM manganese(II)chloride containing 8 µM adenosine-5'-triphosphate (ATP) was added to all test wells except "blank" control wells which contained manganese(II)chloride without ATP. To start the reactions 50 µl of freshly diluted enzyme was added to each well and the plates were incubated at room temperature for 20 minutes. The liquid was then discarded and the wells were washed twice with PBST. One hundred microlitres of mouse IgG anti-phosphotyrosine antibody (Upstate Biotechnology Inc. product 05–321), diluted 1 in 6000 with PBST containing 0.5% w/v bovine serum albumin (BSA), was added to each well and the plates were incubated for 1 hour at room temperature before discarding the liquid and washing the wells twice with PBST. One hundred microlitres of horse radish peroxidase (HRP)-linked sheep anti-mouse Ig antibody (Amersham product NXA 931), diluted 1 in 500 with PBST containing 0.5% w/v BSA, was added and the plates were incubated for 1 hour at room temperature before discarding the liquid and washing the wells twice with PBST One hundred microlitres of 2,2'-azino-bis(3-ethylbenzthiazoline-6-sulphonic acid) (ABTS) solution, freshly prepared using one 50 mg ABTS tablet (Boehringer 1204 521) in 50 ml freshly prepared 50 mM phosphate-citrate buffer pH 5.0+0.03% sodium perborate (made with 1 phosphate citrate buffer with sodium perborate (PCSB) capsule (Sigma P4922) per 100 ml distilled water), was added to each well. Plates were then incubated for 20–60 minutes at room temperature until the optical density value of the "total" control wells, measured at 405 nm using a plate reading spectrophotometer, was approximately 1.0. "Blank" (no ATP) and "total" (no compound) control values were used to determine the dilution range of test compound which gave 50% inhibtion of enzyme activity.

(b) In vitro SAC Proliferation Assay

This assay determines the ability of a test compound to inhibit the growth factor-stimulated proliferation of human umbilical vein endothelial cells (HUVEC).

HUVEC cells were isolated in MCDB 131 (Gibco BRL)+ 7.5% v/v foetal calf serum (FCS) and were plated out (at passage 2 to 8), in MCDB 131+2% v/v FCS+3 µg/ml heparin+1 µg/ml hydrocortisone, at a concentration of 1000 cells/well in 96 well plates. After a minimum of 4 hours they were dosed with the appropriate growth factor (i.e. VEGF 3 ng/ml, EGF 3 ng/ml or b-FGF 0.3 ng/ml) and compound. The cultures were then incubated for 4 days at 37° C. with 7.5% $CO_2$. On day 4 the cultures were pulsed with 1 µCi/well of tritiated-thymidine (Amersham product TRA 61) and incubated for 4 hours. The cells were harvested using a 96-well plate harvester (Tomtek) and then assayed for incorporation of tritium with a Beta plate counter. Incorporation of radioactivity into cells, expressed as cpm, was used to measure inhibition of growth factor-stimulated cell proliferation by compounds.

(c) In vivo Solid Tumour Disease Model

This test measures the capacity of compounds to inhibit solid tumour growth.

CaLu-6 tumour xenografts were established in the flank of female athymic Swiss nu/nu mice, by subcutaneous injection of $1\times10^6$ CaLu-6 cells/mouse in 100 µl of a 50% (v/v) solution of Matrigel in serum free culture medium. Ten days after cellular implant, mice were allocated to groups of 8–10, so as to achieve comparable group mean volumes. Tumours were measured using vernier calipers and volumes were calculated as: $(l\times w)\times\sqrt{(l\times w)}\times(\pi/6)$, where l is the longest diameter and iv the diameter perpendicular to the longest. Test compounds were administered orally once daily for a minimum of 21 days, and control animals received compound diluent. Tumours were measured twice weekly. The level of growth inhibition was calculated by comparison of the mean tumour volume of the control group versus the treatment group using a Student T test and/or a Mann-Whitney Rank Sum Test. The inhibitory effect of compound treatment was considered significant when $p<0.05$.

Although the pharmacological properties of the compounds of Formula I vary with structural change, in general, activity possessed by compounds of the Formula I, may be demonstrated at the following concentrations or doses in one or more of the above tests (a) and (b):

Test (a):—$IC_{50}$ in the range, for example, <10 µM,

Test (b).—$IC_{50}$ in the range, for example, <10 µM;

For example in test (a), Example 1 had an $IC_{50}$ of 0.015–0.05 µM using the KDR receptor.

According to a further aspect of the invention there is provided a pharmaceutical composition which comprises a compound of the formula I as defined hereinbefore or a pharmaceutically acceptable salt thereof, in association with a pharmaceutically acceptable excipient or carrier.

The composition may be in a form suitable for oral administration, for example as a tablet or capsule, for parenteral injection (including intravenous, subcutaneous, intramuscular, intravascular or infusion) for example as a sterile solution, suspension or emulsion, for topical administration for example as an ointment or cream or for rectal administration for example as a suppository. In general the above compositions may be prepared in a conventional manner using conventional excipients.

The compositions of the present invention are advantageously presented in unit dosage form. The compound will normally be administered to a warm-blooded animal at a unit dose within the range 5–5000 mg per square metre body area of the animal, i.e. approximately 0.1–100 mg/kg. A unit dose in the range, for example, 1–100 mg/kg, preferably 1–50 mg/kg is envisaged and this normally provides a therapeutically-effective dose. A unit dose form such as a tablet or capsule will usually contain, for example 1–250 mg of active ingredient.

According to a further aspect of the present invention there is provided a compound of the formula I or a pharmaceutically acceptable salt thereof as defined hereinbefore for use in a method of treatment of the human or animal body by therapy.

We have found that compounds of the present invention inhibit VEGF receptor tyrosine kinase activity and are therefore of interest for their antiangiogenic effects and/or their ability to cause a reduction in vascular permeability.

A further feature of the present invention is a compound of formula I, or a pharmaceutically acceptable salt thereof, for use as a medicament, conveniently a compound of formula I, or a pharmaceutically acceptable salt thereof, for use as a medicament for producing an antiangiogenic and/or vascular permeability reducing effect in a warm-blooded animal such as a human being.

Thus according to a further aspect of the invention there is provided the use of a compound of the formula I, or a pharmaceutically acceptable salt thereof in the manufacture of a medicament for use in the production of an antiangiogenic and/or vascular permeability reducing effect in a warm-blooded animal such as a human being.

According to a further feature of the invention there is provided a method for producing an antiangiogenic and/or vascular permeability reducing effect in a warm-blooded animal, such as a human being, in need of such treatment which comprises administering to said animal an effective amount of a compound of formula I or a pharmaceutically acceptable salt thereof as defined hereinbefore.

As stated above the size of the dose required for the therapeutic or prophylactic treatment of a particular disease state will necessarily be varied depending on the host treated, the route of administration and the severity of the illness being treated. Preferably a daily dose in the range of 1–50 mg/kg is employed. However the daily dose will necessarily be varies depending upon the host treated, the particular route of administration, and the severity of the illness being treated. Accordingly the optimum dosage may be determined by the practitioner who is treating any particular patient.

The antiangiogenic and/or vascular permeability reducing treatment defined hereinbefore may be applied as a sole therapy or may involve, in addition to a compound of the invention, one or more other substances and/or treatments. Such conjoint treatment may be achieved by way of the simultaneous, sequential or separate administration of the individual components of the treatment. In the field of medical oncology it is normal practice to use a combination of different forms of treatment to treat each patient with cancer. In medical oncology the other component(s) of such conjoint treatment in addition to the antiangiogenic and/or vascular permeability reducing treatment defined hereinbefore may be: surgery, radiotherapy or chemotherapy. Such chemotherapy may cover three main categories of therapeutic agent:

(i) other antiangiogenic agents that work by different mechanisms from those defined hereinbefore (for example linomide, inhibitors of integrin αvβ3 function, angiostatin, razoxin, thalidomide), and including vascular targeting agents (for example combretastatin phosphate and the vascular damaging agents described in International Patent Application Publication No. WO 99/02166 the entire disclosure of which document is incorporated herein by reference, (for example N-acetylcolchinol-O-phosphate));

(ii) cytostatic agents such as antioestrogens (for example tamoxifen, toremifene, raloxifene, droloxifene, iodoxyfene), progestogens (for example megestrol acetate), aromatase inhibitors (for example anastrozole, letrazole, vorazole, exemestane), antiprogestogens, antiandrogens (for example flutamide, nilutamide, bicalutamide, cyproterone acetate), LHRH agonists and antagonists (for example goserelin acetate, luprolide), inhibitors of testosterone 5α-dihydroreductase (for example finasteride), anti-invasion agents (for example metalloproteinase inhibitors like marimastat and inhibitors of urokinase plasminogen activator receptor function) and inhibitors of growth factor function, (such growth factors include for example platelet derived growth factor and hepatocyte growth factor such inhibitors include growth factor antibodies, growth factor receptor antibodies, tyrosine kinase inhibitors and serine/threonine kinase inhibitors); and (iii) antiproliferative/antineoplastic drugs and combinations thereof, as used in medical oncology, such as antimetabolites (for example antifolates like methotrexate, fluoropyrimidines like 5-fluorouracil, purine and adenosine analogues, cytosine arabinoside); antitumour antibiotics (for example anthracyclines like doxorubicin, daunomycin, epirubicin and idarubicin, mitomycin-C, dactinomycin, mithramycin); platinum derivatives (for example cisplatin, carboplatin); alkylating agents (for example nitrogen mustard, melphalan, chlorambucil, busulphan, cyclophosphamide, ifosfamide, nitrosoureas, thiotepa); antimitotic agents (for example vinca alkaloids like vincristine and taxoids like taxol, taxotere); topoisomerase inhibitors (for example epipodophyllotoxins like etoposide and teniposide, amsacrine, topotecan, and also irinotecan); also enzymes (for example asparaginase); and thymidylate synthase inhibitors (for example raltitrexed); and additional types of chemotherapeutic agent include:

(iv) biological response modifiers (for example interferon); and (v) antibodies (for example edrecolomab).

For example such conjoint treatment may be achieved by way of the simultaneous, sequential or separate administration of a compound of formula I as defined hereinbefore, and a vascular targeting agent described in WO 99/02166 such as N-acetylcolchinol-O-phosphate (Exampe 1 of WO 99/02166).

As stated above the compounds defined in the present invention are of interest for their antiangiogenic and/or vascular permeability reducing effects. Such compounds of the invention are expected to be useful in a wide range of disease states including cancer, diabetes, psoriasis, rheumatoid arthritis, Kaposi's sarcoma, haemangioma, acute and chronic nephropathies, atheroma, arterial restenosis, autoimmune diseases, acute inflammation, excessive scar formation and adhesions, endometriosis, dysfunctional uterine bleeding and ocular diseases with retinal vessel proliferation. In particular such compounds of the invention are expected to slow advantageously the growth of primary and recurrent solid tumours of, for example, the colon, breast, prostate, lungs and skin. More particularly such compounds of the invention are expected to inhibit the growth of those primary and recurrent solid tumours which are associated with EGF, especially those tumours which are significantly dependent on VEGF for their growth and spread, including for example, certain tumours of the colon, breast, prostate, lung, vulva and skin.

In addition to their use in therapeutic medicine, the compounds of formula I and their pharmaceutically acceptable salts are also useful as pharmacological tools in the development and standardisation of in vitro and in vivo test systems for the evaluation of the effects of inhibitors of VEGF receptor tyrosine kinase activity in laboratory animals such as cats, dogs, rabbits, monkeys, rats and mice, as part of the search for new therapeutic agents.

It is to be understood that where the term "ether" is used anywhere in this specification it refers to diethyl ether.

The invention will now be illustrated in the following non-limiting Examples in which, unless otherwise stated:—

(i) operations were carried out at ambient temperature, i.e. in the range 17 to 25° C. and under an atmosphere of an inert gas such as argon unless otherwise stated;

(ii) evaporations were carried out by rotary evaporation in vacuo and work-up procedures were carried out after removal of residual solids by filtration;

(iii) column chromatography (by the flash procedure) and medium pressure liquid chromatography (MPLC) were performed on Merck Kieselgel silica (Art. 9385) or Merck Lichroprep RP-18 (Art. 9303) reversed-phase silica obtained from E. Merck, Darmstadt, Germany or high pressure liquid chromatography (HPLC) was performed on C18 reverse phase silica, for example on a Dynamax C-18 60 Å preparative reversed-phase column, (iv) yields, where present, are given for illustration only and are not necessarily the maximum attainable;

(v) in general, the end-products of the Formula I have satisfactory microanalyses and their structures were confirmed by nuclear magnetic resonance (NMR) and/or mass spectral techniques; fast-atom bombardment (FAB) mass spectral data were obtained using a Platform spectrometer and, where appropriate, either positive ion data or negative ion data were collected; NMR chemical shift values were measured on the delta scale [proton magnetic resonance spectra were determined using a Varian Gemini 2000 spectrometer operating at a field strength of 300 MHz or a Bruker AM300 spectrometer operating at a field strength of 300 MHz]; the following abbreviations have been used: s, singlet; d, doublet; t, triplet; q, quartet; m, multiplet; br, broad;

(vi) intermediates were not generally filly characterised and purity was assessed by thin layer chromatographic, HPLC, infra-red (IR) and/or NMR analysis;

(vii) melting points are uncorrected and were determined using a Mettler SP62 automatic melting point apparatus or an oil-bath apparatus; melting points for the end-products of the Formula I were determined after crystallisation from a conventional organic solvent such as ethanol, methanol, acetone, ether or hexane, alone or in admixture; and (viii) the following abbreviations have been used:—

| DMF | N,N-dimethylformamide |
|---|---|
| DMSO | dimethylsulphoxide |
| TFA | trifluoroacetic acid |

Gold's reagent {dimethylaminomethyleneaminomethylene)-dimethylammonium chloride, [3-(dimethylamino)-2-azaprop-2-en-1-ylidene]dimethylammonium chloride}

EXAMPLE 1

4-(4-Bromo-2-fluorophenylamino)-7-[2-hydroxy-3-(4-methylpiperazin-1-yl)propoxy]-6-methoxy)quinazoline

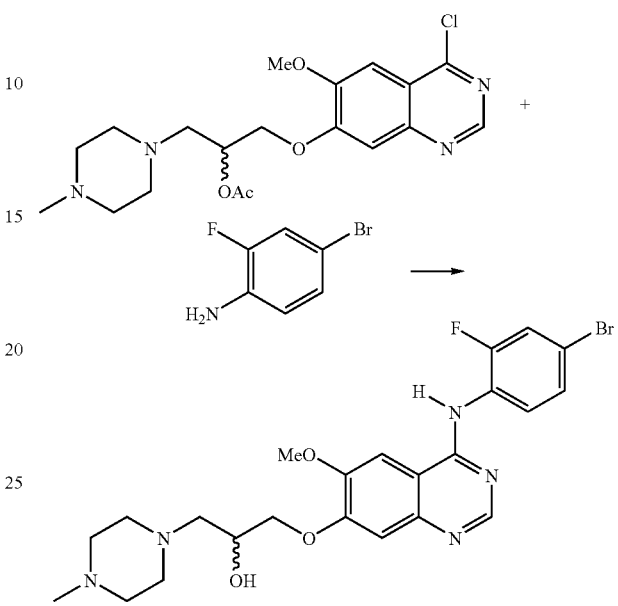

A solution of 7-[2-acetoxy-3-(4-methylpiperazin-1-yl)propoxy]-6-methoxy-4-chloroquinazoline (103 mg, 0.25 mmol) and 2-fluoro-4-brotioaniline (52.7 mg, 0.28 mmol) in isopropanol (3 ml) was heated at 80° C. for 2 hours. After cooling, ether (1 ml) was added and the precipitate was filtered and washed with a mixture of isopropanol/ether (2/1); followed by ether (2 ml). The solid was suspended in a solution of methanol saturated with ammonia (5 ml) and the mixture was stirred for 20 hours at ambient temperature. The volatiles were removed under vacuum. The solid was triturated with ether, filtered and dried overnight under vacuum at 50° C. The solid was dissolved in methanol/methylene chloride (5/95) and eluted though an isolute ® SPE Column (NH2, 10 g) using methanol/methylene chloride (5/95). The fractions containing the expected product were combined and evaporated to give the title product (36 mg, 27%).

MS-ESI: 520 [MH$^+$]

$^1$H NMR Spectrum (DMSO-d$_6$): 2.1 (s, 3H); 2.15–2.5 (m, 10H); 3.9 (s, 3H); 3.9–4.0 (m, 2H); 4.1 (M, 1H); 4.85 (brs, 1H); 7.15 (s, 1H); 7.4 (d, 1H); 7.45 (dd, 1H); 7.6 (d, 1H); 7.75 (s, 1H); 8.3 (s, 1H); 9.5 (s, 1H)

The starting material was prepared as follows.

A mixture of 2-amino-4-benzyloxy-5-methoxybenzamide (10 g, 0.04 mol), (J. Med. Chem. 1977, vol 20, 146–149), and Gold's reagent (7.4 g, 0.05 mol) in dioxane (100 ml) was stirred and heated at reflux for 24 hours. Sodium acetate (3.02 g, 0.037 mol) and acetic acid (1.65 ml, 0.029 mol) were added to the reaction mixture and it was heated for a further 3 hours. The volatiles were removed by evaporation, water was added to the residue, the solid was collected by filtration, washed with water and dried. Recrystallisation from acetic acid gave 7-benzyloxy-6-methoxy-3,4-dihydroquinazolin-4-one (8.7 g, 84%).

Sodium hydride (1.44 g of a 60% suspension in mineral oil, 36 mmol) was added in portions over 20 minutes to a solution of 7-benzyloxy-6-methoxy-3,4-dihydroquinazolin- 4-one (8.4⁶ g, 30 mmol), in DMF (70 ml) and the mixture was stirred for 1.5 hours. Chloromethyl pivalate (5.65 g, 37.5 mmol) was added dropwise and the mixture stirred for 2 hours at ambient temperature. The mixture was diluted with ethyl acetate (100 ml) and poured onto ice/water (400 ml) and 2M hydrochloric acid (4 ml). The organic layer was separated and the aqueous layer extracted with ethyl acetate, the combined extracts were washed with brine, dried (MgSO$_4$) and the solvent removed by evaporation. The residue was triturated with a mixture of ether and petroleum ether, the solid was collected by filtration and dried under vacuum to give 7-benzyloxy-6-methoxy-3-((pivaloyloxy) methyl)-3,4-dihydroquinazolin-4-one (10 g, 84%).

$^1$H NMR Spectrum: (DMSO-d$_6$) 1.11 (s, 9H); 3.89 (s, 3H); 5.3 (s, 2H); 5.9 (s, 2H); 7.27 (s, 1H); 7.35 (m, 1H); 7.47 (t, 2H); 7.49 (d, 2H); 7.51 (s, 1H); 8.34 (s, 1H)

A mixture of 7-benzyloxy-6-methoxy-3-(pivaloyloxymethyl)-3,4-dihydroquinazolin-4-one (7 g, 17.7 mmol) and 10% palladium-on-charcoal catalyst (700 mg) in ethyl acetate (250 ml), DMF (50 ml), methanol (50 ml) and acetic acid (0.7 ml) was stirred under hydrogen at atmospheric pressure for 40 minutes. The catalyst was removed by filtration and the solvent removed from the filtrate by evaporation. The residue was triturated with ether, collected by filtration and dried under vacuum to give 7-hydroxy-6-methoxy-3-(pivaloyloxymethyl)-3,4-dihydroquinazolin-4-one (4.36 g, 80%).

$^1$H NMR Spectrum: (DMSO-d$_6$) 1.1 (s, 9H); 3.89 (s, 3H); 5.89 (s, 2H); 7.0 (s, 1H); 7.48 (s, 1H); 8.5 (s, 1H)

A solution of 7-hydroxy-6-methoxy-3-((pivaloyloxymethyl)-3,4-dihydroquinazolin-4-one (15 g, 49 mmol), 1-bromo-2,3-epoxypropane (6.3 ml, 73.5 mmol), potassium carbonate (13.5 g, 98 mmol) in DMF (150 ml) was stirred at 60° C. for 1 hour followed by 2 hours at 80° C. After cooling, the mixture was poured onto ice/water (600 ml). The precipitate was filtered, washed with water, followed by ether. The solid was dried overnight under vacuum to give 7-(2,3-epoxypropoxy)-6-methoxy-3-(pivaloyloxymethyl)-3,4-dihydroquinazolin-4-one (173 g, 98%)

MS-ESI: 385 [MNa$^+$]

$^1$H NMR Spectrum (DMSO-d$_6$): 1.15 (s, 9H); 2.75 (m, 1H); 2.9 (t, 1H); 3.4 (m, 1H); 3.9 (s, 3H); 3.97 (dd, 1H); 4.52 (dd, 1H); 5.9 (s, 2H); 7.2 (s, 1H); 7.52 (s, 1H); 8.35 (s, 1H).

A solution of 7-(2,3-epoxypropoxy)-6-methoxy-3-(pivaloyloxymethyl)-3,4-dihydroquinazolin-4-one (5 g, 13.8 mmol) and N-methylpiperazine (1.7 ml) in chloroform (70 ml) was refluxed for 21 hours. After cooling the mixture was poured onto a column of silica and eluted with methanol/methylene chloride/ethylacetate (5/45/50) followed by (8/42/50) followed by methanol (saturated with ammonia)/methylene chloride/methanol (5/45/50) followed by (8/42/50). The fractions containing the expected product were combined and the volatiles were removed under vacuum. The solid was triturated with ether, filtered, washed with ether and dried under vacuum to give 7-[2-hydroxy-3-(4-methylpiperazin-1-yl)propoxy]-6-methoxy-3-(pivaloyloxymethyl)-3,4-dihydroquinazolin-4-one (4.8 g, 75%).

$^1$H NMR Spectrum (DMSO-d$_6$): 1.1 (s, 9H); 2.15 (s, 3H); 2.2–2.55 (m, 10H); 3.9 (s, 3H); 3.95–4.02 (m, 2H); 4.15 (d, 1H); 4.95 (br s, 1H); 5.9 (s, 2H); 7.2 (s, 1H); 7.45 (s, 1H); 8.32 (s, 1H)

A solution of 7-[2-hydroxy-3-(4-methylpiperazin-1-yl) propoxy]-6-methoxy-3-(pivaloyloxymethyl)-3,4-dihydroquinazolin-4-one (4.3 g, 9.3 mmol) in methanol saturated with ammonia (100 ml) was stirred for 2 days at ambient temperature. The volatiles were removed under vacuum and the residue was triturated with ether, filtered, washed with ether and dried under vacuum to give 7-(2-hydroxy-3-(4-methylpiperazin-1-yl)propoxy)-6-methoxyquinazolin-4-one (3.4 g, quant.).

$^1$H NMR Spectrum (DMSO-d$_6$): 2.15 (s, 3H); 2.2–2.6 (m, 10H); 39 (s, 3H); 4.05 (d, 2H); 4.15 (m, 1H); 4.9 (br s, 1H); 7.15 (s, 1H); 7.45 (s, 1H); 8.0 (s, 1H)

A solution of 7-[2-hydroxy-3-(4-methylpiperazin-1-yl) propoxy]-6-methoxyquinazolin-4-one (1.2 g, 3.3 mmol) and acetic anhydride (670 µl) in ether (2 ml) was stirred 10 minutes at ambient temperature. Ether (2 ml) was further added, followed by acetic anhydride (670 µl). After stirring 1 hour at ambient temperature, water (305 µl) was added and stirring was continued for 1.5 hours. The mixture was partitioned between methylene chloride and saturated sodium bicarbonate. The organic layer was separated and the aqueous layer was further extracted with methylene chloride. The organic layers were combined, dried (MgSO$_4$) and evaporated. The solid was triturated with ether, filtered, washed with ether and dried under vacuum to give 7-[2-acetoxy-3-(4-methylpiperazin-1-yl)propoxy]-6-methoxyquinazolin-4-one (0.93 g, 72%).

MS-ESI: 391 [MH]+

$^1$H NMR Spectrum (DMSO-d$_6$): 2.0 (s, 3H); 2.12 (s, 3H); 2.3 (br s, 4H); 2.4–2.7 (m, 6H); 3.9 (s, 3H); 4.3 (m, 2H); 5.3 (m, 1H); 7.2 (s, 1H); 7.45 (s, 1H); 8.0 (s, 1H); 12.07 (br s, 1H)

A solution of 7-[2-acetoxy-3-(4-methylpiperazin-1-yl) propoxy]-6-methoxyquinazolin-4-one (930 mg, 2.4 mmol) in thionyl chloride (10 ml) containing DMF (150 µl) was heated at 80° C. for 5 hours. The volatiles were removed under vacuum and the residue azeotroped with toluene. The solid was partitioned between methylene chloride and water and the pH of the aqueous layer was adjusted to 7 with solid sodium bicarbonate. The organic layer was separated, washed with brine, dried (MgSO$_4$) and evaporated. The residue was purified by column chromatography eluting with methylene chloride/methanol saturated with ammonia (95/5). The fractions containing the expected product were combined and the volatiles were removed under vacuum to give 7-[2-acetoxy-3-(4-methylpiperazin-1-yl)propoxy]-6-methoxy-4-chloroquinazoline (859 mg, 88%).

MS-ESI-409 [MH$^+$]

$^1$H NMR Spectrum (DMSO-d$_6$): 2.02 (s, 3H); 2.13 (s, 3H); 2.2–2.35 (m, 4H), 2.35–2.6 (m, 4H); 2.6 (m, 2H); 4.0 (s, 3H); 4.2 (m, 2H); 5.35 (m, 1H); 7.41 (s, 1H); 7.53 (s, 1H); 8.51 (s, 1H)

EXAMPLE 2

4-(4-Chloro-2-fluorophenylamino)-7-[2-hydroxy-3-(pyrrolidin-1-yl)propoxy]-6-methoxy)quinazoline

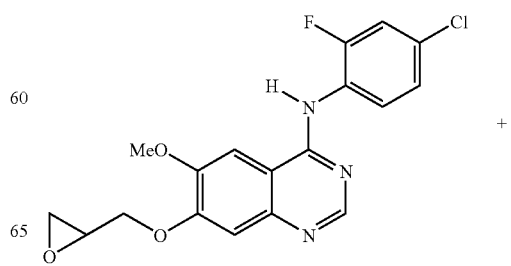

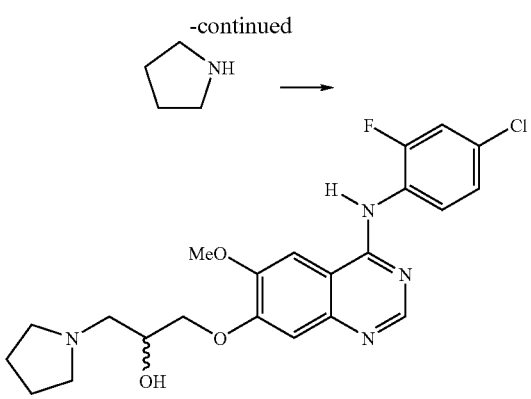

A solution of 4-(4-chloro-2-fluorophenylamino)-7-(2,3-epoxypropoxy)-6-methoxyquinazoline (56 mg, 0.15 mmol) and pyrrolidine (96 mg, 0.37 mmol) in a mixture of chloroform (500 μl) and ethanol (500 μl) was stirred at 40° C. for 5 hours. Methylene chloride (10 ml) was added and the mixture was poured onto silica and eluted with methylene chloride, followed by methylene chloride/methanol (98/2) followed by methylene chloride/methanol saturated with ammonia (97/3) and (95/5). The fractions containing the expected product were combined and the volatiles were removed under vacuum. The residue was triturated with 6.2N ethereal hydrogen chloride (25 μl). The precipitate was filtered and dried under vacuum to give the title product as the hydrochloride (31.5 mg, 41%).

MS-ESI: 447 [MH]$^+$ $^1$H NMR Spectrum (DMSO-d$_6$, CF$_3$COOD): 1.85–2.1 (m, 4H); 3.1–3.2 (m, 2H); 3.38 (d, 2H); 3.6–3.7-m, 2H); 4.05 (s, 3H); 425 (d, 2H); 4.4 (t, 1H); 7.43 (s, 1H); 7.45 (d, 1H); 7.6–7.7 (m, 2H); 8.2 (s, 1H); 8.9 (s, 1H)

The starting material was prepared as follows:

A solution of 7-benzyloxy-4-chloro-6-methoxyquinazoline (1.2 g, 4 mmol), (prepared for example as described in WO 00/47212 Example 1), and 4-chloro-2-fluoroaniline (444 μl, 4 mmol) in 2-propanol (40 ml) was refluxed for 1.5 hours. After cooling, the precipitate was collected by filtration, washed with 2-propanol then ether and dried under vacuum to give 7-benzyloxy-4-(4-chloro-2-fluorophenylamino)-6-methoxyquinazoline hydrochloride (1.13 g, 64%).

m.p. 239–242° C.

$^1$H NMR Spectrum: (DMSO-d$_6$) 4.0 (s, 3H); 5.36 (s, 2H); 7.39–7.52 (m, 9H); 8.1 (s, 1H); 8.75 (s, 1H)

MS-ESI: 410 [MH]$^+$

| Elemental analysis: | Found | C 59.2 | H 4.3 | N 9.4 |
|---|---|---|---|---|
| C$_{22}$H$_{17}$N$_3$O$_2$ClF 1 HCl | Requires | C 59.2 | H 4.1 | N 9.41% |

A solution of 7-benzyloxy-4-(4-chloro-2-fluorophenylamino)-6-methoxyquinazoline hydrochloride (892 mg, 2 mmol) in TFA (10 ml) was refluxed for 50 minutes. After cooling, the mixture was poured onto ice. The precipitate was collected by filtration, dissolved in methanol (10 ml) and basified to pH 11 with aqueous ammonia. After concentration by evaporation, the solid product was collected by filtration, washed with water then ether and dried under vacuum to give 4-(4-chloro-2-fluorophenylamino)-7-hydroxy-6-methoxyquinazoline as a yellow solid (460 mg, 72%).

m.p. 141–143° C.

$^1$H NMR Spectrum: (DMSO-d$_6$) 3.95 (s, 3H); 7.05 (s, 1H); 7.35 (d, 1H); 7.54–7.59 (m, 2H) 7.78 (s, 1H); 8.29 (s, 1H)

MS-ESI: 320–322 [MH]$^+$

To a solution of 7-hydroxy-6-methoxy-4-(2-fluoro-4-chlorophenylamino)quinazoline (5.56 g, 17.4 mmol) in DMF (100 ml) containing potassium carbonate (4.8 g, 34.8 mmol) was added 1-bromo-2,3-epoxypropane (1.49 ml, 17.4 mmol). The mixture was stirred at 60° C. for 3 hours. After cooling, water (400 ml) was added The precipitate was filtered and dried under vacuum at 60° C. for 2 hours over P$_2$O$_5$. The product was purified by column chromatography eluting with methylene chloride followed by methylene chloride/methanol saturated with ammonia 98/2. The fractions containing the expected product were combined and evaporated to give 4-(4-chloro-2-fluorophenylamino)-7-(2,3-epoxypropoxy)-6-methoxyquinazoline (2.82 g, 43%).

MS-ESI: 376–378 [MH]$^+$ $^1$H NMR Spectrum (DMSO-d$_6$): 2.8 (m, 1H); 2.92 (m, 1H); 3.45 (m, 1H); 3.98 (s, 3H); 4.02 (m, 1H); 4.55 (dd, 1H); 7.25 (s, 1H); 7.35 (d, 1H); 7.5–7.65 (m, 2H); 7.85 (s, 1H) 8.4 (s, 1H);9.6 (br s, 1H)

EXAMPLE 3

4-(4-Chloro-2-fluorophenylamino)-7-[2-hydroxy-3-(4-methylpiperazin-1-yl)propoxy]-6-methoxy)quinazoline

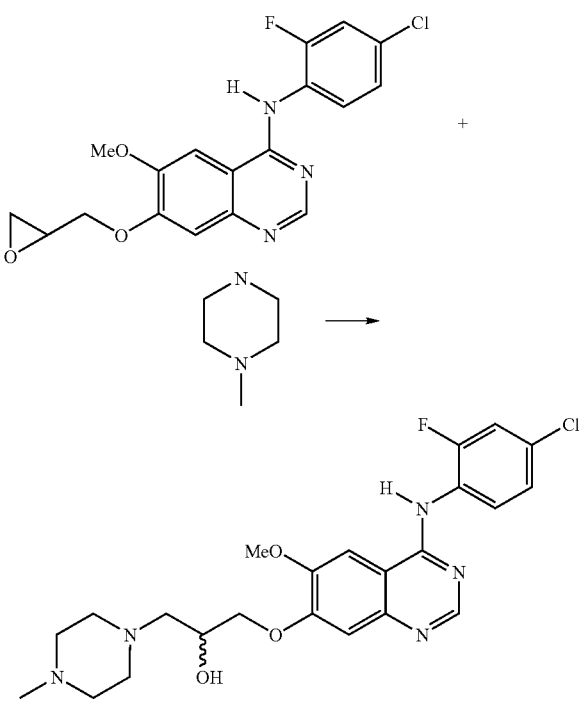

4-(4-Chloro-2-fluorophenylamino)-7-(2',3-epoxypropoxy)-6-methoxyquinazoline (56 mg, 0.15 mmol) was reacted with methylpiperazine (37 mg, 0.37 mmol) using a similar procedure to that described in Example 2. The title compound was isolated as the free base (45 mg, 63%) after column chromatography and evaporation of the volatiles.

MS-ESI: 476 [MH]$^+$ $^1$H NMR Spectrum (DMSO-d$_6$): 2.15 (s, 3H); 2.2–2.6 (m, 10H); 3.45 (m, 2H); 3.98 (s, 3H); 4.05 (m, 2H); 4.2 (m, 1H); 4.92 (d, 1H); 7.22 (s, 1H); 7.35 (d, 1H); 7.5–7.65 (m, 2H); 7.8 (s, 1H); 835 (s, 1H); 9.55 (s, 1H)

EXAMPLE 4

4-(4-Chloro-2-fluorophenylamino)-7-(2-hydroxy-3-(morpholino)propoxy)-6-methoxy)quinazoline

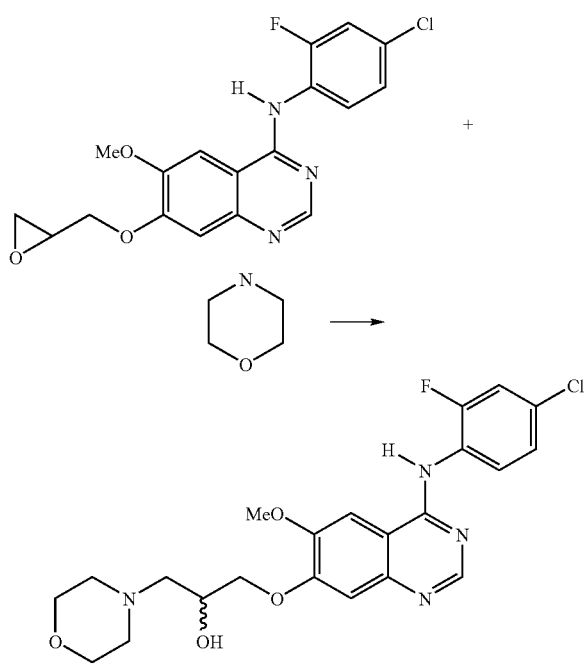

4-(4-Chloro-2-fluorophenylamino)-7-(2,3-epoxypropoxy)-6-methoxyquinazoline (56 mg, 0.15 mmol) was reacted with morpholine (32 mg, 0.37 mmol) using a similar procedure to that in Example 2, to give the title compound as the hydrochloride (17.5 mg, 22%) after salt formation.

MS-ESI: 463 [MH]$^+$ $^1$H NMR Spectrum (DMSO-d$_6$): 3.12 (m, 4H); 3.4 (m, 2H); 3.8 (m, 4H); 4.0 (s, 3H); 4.2 (m, 2H); 4.3–4.4 (br, 1H); 728 (s, 1H); 7.38 (d, 1H); 7.5–7.65 (m, 2H); 7.9 (s, 1H); 8.4 (s, 1H); 8.9–9.1 (br s, 1H); 9.7 (br s, 1H)

EXAMPLE 5

4-(4-Bromo-2-fluorophenylamino)-7-[2-hydroxy-3-(thiazolidin-3-yl)propoxy]-6-methoxy)quinazoline

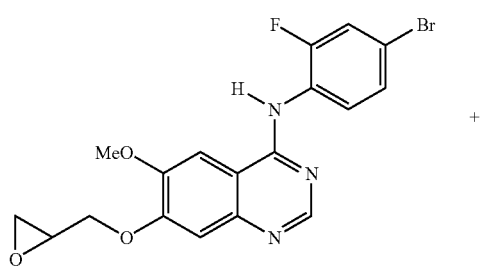

-continued

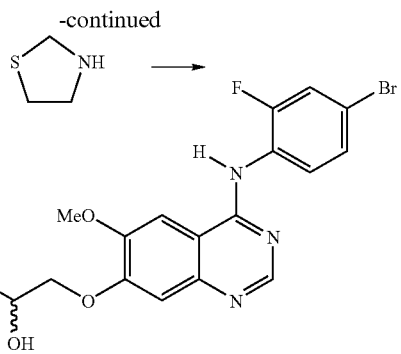

Thiazolidine (53 mg, 0.6 mmol) was added to a solution of 4-(4-bromo-2-fluorophenylamino)-7-(2,3-epoxypropoxy)-6-methoxyquinazoline (100 mg, 0.24 mmol) in a mixture of ethanol (1 ml) and chloroform (1 ml). The mixture was stirred at 40° C. for 24 hours. Methylene chloride (20 ml) was added and the mixture was poured onto an isolute® column of silica and eluted with methylene chloride (15 ml) followed by methylene chloride/ethylacetate/methanol (48/50/2) (60 ml) followed by methylene chloride/ethylacetate/methanol saturated with ammonia (46/50/4) (90 ml) and by (42/50/8) (150 ml). The fractions containing the expected product were combined and the volatiles were removed under (vacuum The residue was diluted with of isopropanol (2 ml) and 6N hydrogen chloride in isopropanol (25 µl) was added. The precipitate was filtered, washed with ether and dried under vacuum to give the title compound as the hydrochloride (65 mg, 48%).

MS-ESI: 509–511 [MH]$^+$ $^1$H NMR Spectrum (DMSO-d$_6$, CF$_3$COOD): 3.25 (m, 2H); 3.4–3.6 (m, 2H); 3.6–3.9 (br m, 2H); 4.05 (s, 3H); 4.25 (s, 2H); 4.4–4.5 (m, 1H); 4.5–4.6 (m, 2H); 7.42 (s, 1H); 7.5–7.62 (m, 2H); 7.8 (d, 1H); 8.12 (s 1H); 8.9 (s, 1H)

The starting material was prepared as follows:

A solution of 7-benzyloxy-4-chloro-6-methoxyquinazoline (8.35 g, 27.8 mmol), and 4-bromo-2-fluoroaniline (5.65 g, 29.7 mmol) in 2-propanol (200 ml) was heated at reflux for 4 hours. The resulting precipitate was collected by filtration, washed with 2-propanol and then ether and dried under vacuum to give 7-benzyloxy-4-(4-bromo-2-fluorophenylamino)-6-methoxyquinazoline hydrochloride (9.46 g, 78%).

$^1$H NMR Spectrum: (DMSO-d$_6$; CD$_3$COOD) 4.0 (s, 3H); 5.37 (s, 2H); 7.35–7.5 (m, 4H); 7.52–7.62 (m, 4H); 7.8 (d, 1H); 8.14 (9s, 1H); 8.79 (s, 1H)

MS-ESI: 456 [MH]$^+$

| Elemental analysis: | Found | C 54.0 | H 3.7 | N 8.7 |
|---|---|---|---|---|
| C$_{22}$H$_{17}$N$_3$O$_2$BrF 0.9 HCl | Requires | C 54.2 | H 3.7 | N 8.6% |

A solution of 7-benzyloxy-4-(4-bromo-2-fluorophenylamino)-6-methoxyquinazoline hydrochloride (9.4 g, 19.1 mmol) in TFA (90 ml) was heated at reflux for 50 minutes. The mixture was allowed to cool and was poured on to ice. The resulting precipitate was collected by filtration and dissolved in methanol (70 ml). The solution was adjusted to pH 9–10 with concentrated aqueous ammonia solution. The mixture was concentrated to half initial volume by evaporation. The resulting precipitate was collected by filtration, washed with water and then ether, and dried under vacuum to give 4-(4-bromo-2-fluorophenylamino)-7-hydroxy-6-methoxyquinazoline (5.66 g, 82%).

¹H NMR Spectrum: (DMSO-d₆; CD₃COOD) 3.95 (s, 3H); 7.09 (s, 1H); 7.48 (s, 1H); 7.54 (t, 1H); 7.64 (d, 1H); 7.79 (s, 1H); 8.31 (s, 1H)

MS-ESI: 366 [MH]⁺

| Elemental analysis: | Found | C 49.5 | H 3.1 | N 11.3 |
|---|---|---|---|---|
| $C_{15}H_{11}N_3O_2BrF$ | Requires | C 49.5 | H 3.0 | N 11.5% |

Using a similar procedure to the one described in Example 2 for the preparation of 4-(4-chloro-2fluorophenylamino)-7-(2,3-epoxypropoxy)-6-methoxyquinazoline, 7-hydroxy-6-methoxy-4-(2-fluoro-4-bromophenylamino) quinazoline (6 g, 16.5 mmol) was reacted with 1-bromo-2,3-epoxypropane (1.7 ml, 19.8 mmol) in DMF (50 ml) in the presence of potassium carbonate (4.55 g, 3.3 mmol) and purified as described to give 4-(4-bromo-2-fluorophenylamino)-7-(2,3-epoxypropoxy)-6-methoxyquinazoline (1.8 g, 26%).

MS-ESI: 420–422 [MH]⁺

¹H NMR Spectrum (DMSO-d₆): 2.75 (m, 1H); 2.9 (m, 1H); 3.42 (m, 1H); 3.97 (s, 3H); 4.02 (m, 1H); 4.55 (dd, 1H); 722 (s, 1H); 7.48 (d, 1H); 7.52 (dd, 1H); 7.65 (d, 1H); 7.82 (s, 1H); 8.37 (s, 1H); 9.58 (s, 1H)

HPLC retention time (min) 3.20

HPLC retention time were measured as follows:

TSK gel Super ® ODS 2 μm 4.6 mm×5 cm—eluting with a linear gradient of 0% to 100% CH₃CN in water containing 0.1% TFA over 7 min.—Flow rate: 1.4 ml/min—Detection U.V (254 nm) and LDD. Samples are dissolved in 1 drop DMSO and diluted with water.

EXAMPLE 6

4-(4-Bromo-2-fluorophenylamino)-7-(2,3-epoxypropoxy)-6-methoxyquinazoline (from Example 5) (100 mg, 0.24 mmol) was reacted with the appropriate amine using a similar procedure to that described in Example 5, to give the compounds described in Table I.

TABLE I

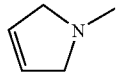

| Compound | R¹R²N | Weight (mg) | Yield (%) | MS-ESI [MH]⁺ | HPLC RT min | Note |
|---|---|---|---|---|---|---|
| 1 | 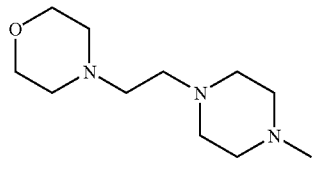 | 20 | 16 | 489–491 | 3.16 | a |
| 2 | 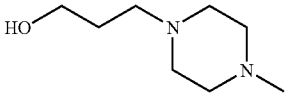 | 89 | 64 | 619–621 | 3.05 | b |
| 3 | 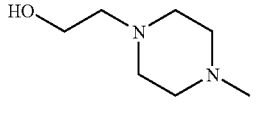 | 65 | 49 | 564–566 | 3.04 | c |
| 4 | 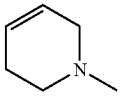 | 62 | 47 | 550–552 | 3.03 | d |
| 5 |  | 30 | 24 | 503–505 | 3.22 | e |
| 6 | tBuN(Me)— | 17 | 14 | 507–509 | 3.30 | f |
| 7 | iPrN(Me)— | 12 | 10 | 493–495 | 3.24 | g |
| 8 | iBuN(Me)— | 28 | 23 | 507–509 | 3.36 | h |

TABLE I-continued

[Structure: 4-(4-bromo-2-fluorophenylamino)-6-methoxy-7-[2-hydroxy-3-(R1R2N)propoxy]quinazoline]

| Compound | R¹R²N | Weight (mg) | Yield (%) | MS-ESI [MH]⁺ | HPLC RT min | Note |
|---|---|---|---|---|---|---|
| 9 | HO-CH₂CH₂-N(Me)- (with N-Me) | 24 | 19 | 495–497 | 3.10 | i |
| 10 | morpholino | 59 | 44 | 507–509 | 3.13 | j |
| 11 | Me₂N— | 17 | 14 | 465–467 | 3.12 | k |
| 12 | piperidin-1-yl | 25 | 20 | 505–507 | 3.25 | l |
| 13 | pyrrolidin-1-yl | 54 | 41 | 491–493 | 3.18 | m | a 4-(4-Bromo-2-fluorophenylamino)-7-(2,3-epoxypropoxy)-6-methoxyquinazoline was reacted with 3-pyrroline (41 mg) to give 4-(4-bromo-2-fluorophenylamino)-7-[2-hydroxy-3-(3-pyrrolin-1-yl)propoxy]-6-methoxyquinazoline hydrochloride. ¹H NMR Spectrum (DMSO, CF₃COOD): 3.45–3.55(m, 2H); 4.01(s, 3H); 4.05–4.2(m, 2H); 4.2–4.5(m, 5H); 6.0(s, 2H); 7.4(s, 1H); 7.5–7.65(m, 2H); 7.85(d, 1H); 8.2(s, 1H); 8.9(s, 1H)

b 4-(4-Bromo-2-fluorophenylamino)-7-(2,3-epoxypropoxy)-6-methoxyquinazoline was reacted with 1-(2-morpholinoethyl)piperazine (120 mg) to give 4-(4-bromo-2-fluorophenylamino)-7-[2-hydroxy-3-(4-(2-morpholinoethyl)piperazin-1-yl)propoxy]-6-methoxyquinazoline hydrochloride. ¹H NMR Spectrum (DMSO-d₆, CF₃COOD): 3.2–3.8(m, 18H); 3.9(br s, 4H); 4.08(s, 3H); 4.3(d, 2H); 4.55(br s, 1H); 7.5(s, 1H); 7.52–7.65(m, 2H); 7.8(d, 1H); 8.22(s, 1H); 8.9(s, 1H)

c 4-(4-Bromo-2-fluorophenylamino)-7-(2,3-epoxypropoxy)-6-methoxyquinazoline was reacted with 1-(3-hydroxypropyl)piperazine (87 mg), (Chem. Pharm. Bull. 1994, 42(4), 963–71), to give 4-(4-bromo-2-fluorophenylamino)-7-[2-hydroxy-3-(4-(3-hydroxypropyl)piperazin-1-yl)propoxy]-6--methoxyquinazoline hydrochloride. ¹H NMR Spectrum (DMSO-d₆, CF₃COOD): 1.75–1.95(m, 2H); 3.2–3.9 (m, 14H); 4.1(s, 3H); 4.3(s, 2H); 4.5–4.6(m, 1H); 7.5(s, 1H); 7.55–7.65(m, 2H); 7.75(d, 1H); 8.25(s, 1H); 8.85(s, 1H)

d 4-(4-Bromo-2-fluorophenylamino)-7-(2,3-epoxypropoxy)-6-methoxyquinazoline was reacted with 1-(2-hydroxyethyl)piperazine (78 mg) to give 4-(4-bromo-2-fluorophenylamino)-7-[2-hydroxy-3-(4-(2-hydroxyethyl)piperazin-1-yl)propoxy]-6-methoxyquinazoline hydrochloride. ¹H NMR Spectrum (DMSO-d₆, CF₃COOD): 3.3(br s, 2H); 3.3–3.9(m, 12H); 4.1(s, 3H); 4.25(d, 2H); 4.55(m, 1H); 7.5(s, 1H); 7.55–7.65(m, 2H); 7.8(d, 1H); 8.25(s, 1H); 8.9(s, 1H)

e 4-(4-Bromo-2-fluorophenylamino)-7-(2,3-epoxypropoxy)-6-methoxyquinazoline was reacted with 1,2,3,6-tetrahydropyridine (50 mg) to give 4-(4-bromo-2-fluorophenylamino)-7-[2-hydroxy-3-(1,2,3,6-tetrahydropyridin-1-yl)propoxy]-6-methoxyquinazoline hydrochloride. ¹H NMR Spectrum (DMSO-d₆, CF₃COOD): 3.25–3.5(m, 5H); 3.5–3.65(m, 1H); 3.75(d, 1H); 3.95(m, 1H); 4.02(s, 3H); 4.25(d, 2H); 4.5(m, 1H); 5.8(d, 1H); 5.95(br s, 1H); 7.45(s, 1H); 7.55–7.65(m, 2H); 7.8(d, 1H); 8.2(s, 1H); 8.9(s, 1H)

f 4-(4-Bromo-2-fluorophenylamino)-7-(2,3-epoxypropoxy)-6-methoxyquinazoline was reacted with N-tertbutyl-N-methylamine (52 mg) to give 4-(4-bromo-2-fluorophenylamino)-7-[2-hydroxy-3-(N-tertbutyl-N-methylamino)propoxy]-6-methoxyquinazoline hydrochloride.

g 4-(4-Bromo-2-fluorophenylamino)-7-(2,3-epoxypropoxy)-6-methoxyquinazoline was reacted with N-isopropyl-N-methylamine (44 mg) to give 4-(4-bromo-2-fluorophenylamino)-7-[2-hydroxy-3-(N-isopropyl-N-methylamino)propoxy]-6-methoxyquinazoline hydrochloride.

h 4-(4-Bromo-2-fluorophenylamino)-7-(2,3-epoxypropoxy)-6-methoxyquinazoline was reacted with N-(iso-butyl)-N-methylamine (52 mg) to give 4-(4-bromo-2-fluorophenylamino)-7-[2-hydroxy-3-(N-isobutyl-N-methylamino)propoxy]-6-methoxyquinazoline hydrochloride.

TABLE I-continued

![structure]

| Compound | $R^1R^2N$ | Weight (mg) | Yield (%) | MS-ESI $[MH]^+$ | HPLC RT min | Note |
|---|---|---|---|---|---|---| i 4-(4-Bromo-2-fluorophenylamino)-7-(2,3-epoxypropoxy)-6-methoxyquinazoline was reacted with N-(2-hydroxyethyl)-N-methylamine (45 mg) to give 4-(4-bromo-2-fluorophenylamino)-7-[2-hydroxy-3-(N-(2-hydroxyethyl)-N-methylamino)propoxy]-6-methoxyquinazoline hydrochloride. $^1$H NMR Spectrum (DMSO-$d_6$, CF$_3$COOD): 2.90(s, 3H); 3.2–3.35(m, 2H); 3.35–3.45(m, 2H); 3.82(br s, 2H); 4.02 (s, 3H); 4.25(s, 2H); 4.45(br s, 1H); 7.45(s, 1H); 7.5–7.65(m, 2H); 7.82(d, 1H); 8.2(s, 1H); 8.9(s, 1H)

j 4-(4-Bromo-2-fluorophenylamino)-7-(2,3-epoxypropoxy)-6-methoxyquinazoline was reacted with morpholine (52 mg) to give give 4-(4-bromo-2-fluorophenylamino)-7-[2-hydroxy-3-(morpholino)propoxy]-6-methoxyquinazoline hydrochloride. $^1$H NMR Spectrum (DMSO-$d_6$, CF$_3$COOD): 3.1–3.45(m, 4H); 3.5(t, 2H); 3.7–3.9(m, 2H); 3.95(d, 2H); 4.02(s, 3H); 4.3(d, 2H); 4.5(m, 1H); 7.45(s, 1H); 7.5–7.62(m, 2H); 7.8(d, 1H); 8.2(s, 1H); 8.9(s, 1H)

k 4-(4-Bromo-2-fluorophenylamino)-7-(2,3-epoxypropoxy)-6-methoxyquinazoline was reacted with dimethylamine (27 mg) to give 4-(4-bromo-2-fluorophenylamino)-7-(2-hydroxy-3-(N,N-dimethylamino)propoxy]-6-methoxyquinazoline hydrochloride. $^1$H NMR Spectrum (DMSO-$d_6$, CF$_3$COOD): 2.9(s, 3H); 2.95(s, 3H); 3.3(m, 2H); 4.05(s, 3H); 4.25(d, 2H); 4.45(m, 1H); 7.42(s, 1H); 7.5–7.65(m, 2H); 7.8(d, 1H); 8.2(s, 1H); 8.9(s, 1H)

l 4-(4-Bromo-2-fluorophenylamino)-7-(2,3-epoxypropoxy)-6-methoxyquinazoline was reacted with piperidine (51 mg) to give 4-(4-bromo-2-fluorophenylamino)-7-[2-hydroxy-3-(piperidin-1-yl)propoxy]-6-methoxyquinazoline hydrochloride. $^1$H NMR Spectrum (DMSO-$d_6$, CF$_3$COOD): 1.4–1.5(m, 1H); 1.7–1.9(m, 5H); 2.9–3.2(m, 2H); 3.3–3.4(m, 2H); 3.55(t, 2H); 4.02(s, 3H); 4.25(d, 2H); 4.5(m, 1H); 7.45(s, 1H); 7.5–7.6(m, 2H); 7.8(d, 1H); 8.2(s, 1H); 8.9(s, 1H)

m 4-(4-Bromo-2-fluorophenylamino)-7-(2,3-epoxypropoxy)-6-methoxyquinazoline was reacted with pyrrolidine (45 mg) to give 4-(4-bromo-2-fluorophenylamino)-7-[2-hydroxy-3-(pyrrolidin-1-yl)propoxy]-6-methoxyquinazoline hydrochloride. $^1$H NMR Spectrum (DMSO-$d_6$, CF$_3$COOD): 1.9–2.15(m, 4H); 3.2(m, 2H); 3.4(d, 2H); 3.7(m, 2H); 4.05(s, 3H); 4.3(d, 2H); 4.4(m, 1H); 7.42(s, 1H); 7.5–7.65 (m, 2H); 7.8(d, 1H); 8.2(s, 1H); 8.9(s, 1H)

EXAMPLE 7

4-(4-Chloro-2-fluorophenylamino)-7-(2,3-epoxypropoxy)-6-methoxyquinazoline (100 mg, 0.26 mmol) (from Example 4) was reacted with the appropriate amine (0.65 mmol) using, a similar procedure to that described in Example 4, to give the compound described in Table II.

TABLE II

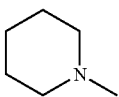

| Compound | $R^1R^2N$ | Weight (mg) | Yield (%) | MS-ESI $[MH]^+$ | HPLC RT min | Note |
|---|---|---|---|---|---|---|
| 1 | Me$_2$N— | 31 | 25 | 421–423 | 3.04 | a |
| 2 | (N-methylpiperidine) | 86 | 62 | 461–463 | 3.17 | b |

TABLE II-continued

| Compound | R¹R²N | Weight (mg) | Yield (%) | MS-ESI [MH]⁺ | HPLC RT min | Note |
|---|---|---|---|---|---|---|
| 3 | N-methylhexahydroazepine | 70 | 52 | 475–477 | 3.27 | c |
| 4 | HO-CH₂CH₂-N(Me)₂ | 43 | 34 | 451–453 | 3.03 | d |
| 5 | N-methylthiazolidine | 80 | 58 | 465–467 | 3.13 | e |
| 6 | N-methyl-2,5-dihydropyrrole | 69 | 51 | 445–447 | 3.09 | f |
| 7 | thiomorpholine (N-methyl) | 86 | 62 | 479–481 | 3.16 | g |
| 8 | 3-hydroxy-N-methylpyrrolidine | 48 | 37 | 463–465 | 3.04 | h |
| 9 | 4-(2-morpholinoethyl)-N-methylpiperazine | 40 | 31 | 575–577 | 2.99 | i |
| 10 | 1-(3-hydroxypropyl)-4-methylpiperazine | 72 | 53 | 520–522 | 2.97 | j |
| 11 | 1-(2-hydroxyethyl)-4-methylpiperazine | 64 | 48 | 506–508 | 2.96 | k |
| 12 | N-methylazetidine | 25 | 20 | 433–435 | 3.07 | l |

TABLE II-continued

| Compound | R¹R²N | Weight (mg) | Yield (%) | MS-ESI [MH]⁺ | HPLC RT min | Note |
|---|---|---|---|---|---|---|
| 13 | 2,5-dimethyl-2,5-dihydro-1H-pyrrol-1-yl (Me, N-Me, Me) | 7 | 6 | 473–475 | 3.23 | m |
| 14 | 4-methylpiperidin-1-yl | 38 | 30 | 475–477 | 3.29 | n |
| 15 | N-methyl-N-propargylamino | 55 | 42 | 445–447 | 3.13 | o |
| 16 | 2-methylpyrrolidin-1-yl | 18 | 15 | 461–463 | 3.18 | p |
| 17 | iPrN(Et)— | 73 | 54 | 463–465 | 3.23 | q |
| 18 | N-(2-cyanoethyl)-N-methylamino | 20 | 16 | 460–462 | 3.09 | r |
| 19 | iPr1N(Me)— | 52 | 40 | 449–451 | 3.17 | s |
| 20 | iBuN(Me)— | 36 | 28 | 463–465 | 3.3 | t |
| 21 | n-PrN(Et)— | 36 | 29 | 463–465 | 3.27 | u | a 4-(4-Chloro-2-fluorophenylamino)-7-(2,3-epoxypropoxy)-6-methoxyquinazoline was reacted with dimethylamine (29 mg) to give 4-(4-chloro-2-fluorophenylamino)-7-[2-hydroxy-3-(N,N-dimethylamino)propoxy]-6-methoxyquinazoline hydrochloride. ¹H NMR (DMSO-$d_6$, CF$_3$COOD): 2.87(s, 3H); 2.92(s, 3H); 3.3(m, 2H); 4.05(s, 2H); 4.22(d, 2H); 4.42(m, 1H); 7.45(s, 1H); 7.5(d, 1H); 7.62(dd, 1H); 7.7(dd, 1H); 8.2(s, 1H); 8.9(s, 1H)

b 4-(4-Chloro-2-fluorophenylamino)-7-(2,3-epoxypropoxy)-6-methoxyquinazoline was reacted with piperidine (55 mg) to give 4-(4-chloro-2-fluorophenylamino)-7-[2-hydroxy-3-(piperidin-1-yl)propoxy]-6-methoxyquinazoline hydrochloride. ¹H NMR Spectrum (DMSO-$d_6$): 1.4–1.5(m, 1H); 1.6–1.95(m, 5H); 2.45–3.05(m, 2H); 3.1–3.25(m, 2H); 3.55(br s, 2H); 4.02(s, 3H); 4.2(d, 2H); 4.5(m, 1H); 6.1(br s, 1H); 7.45(s, 1H); 7.47(d, 1H); 7.6(dd, 1H); 7.65(d, 1H); 8.25(s, 1H); 8.8(s, 1H); 9.75(br s, 1H)

c 4-(4-Chloro-2-fluorophenylamino)-7-(2,3-epoxypropoxy)-6-methoxyquinazoline was reacted with homopiperidine (64 mg) to give 4-(4-chloro-2-fluorophenylamino)-7-[2-hydroxy-3-(homopiperidin-1-yl)propoxy[-6-methoxyquinazoline hydrochloride. ¹H NMR Spectrum (DMSO-$d_6$, CF$_3$COOD): 1.6–1.8(m, 4H); 1.8–2.0(m, 4H); 3.20–3.35(m, 3H); 3.4–3.55(m, 3H); 4.02(s, 3H); 4.25(d, 2H); 4.45 (m, 1H); 7.45(s, 1H); 7.5(d, 1H); 7.62(dd, 1H); 7.7(d, 1H); 8.2(s, 1H); 8.9(s, 1H)

d 4-(4-Chloro-2-fluorophenylamino)-7-(2,3-epoxypropoxy)-6-methoxyquinazoline was reacted with N-methyl-N-(2-hydroxyethyl)amine (49 mg) to give 4-(4-chloro-2-fluorophenylamino)-7-[2-hydroxy-3-(N-(2-hydroxyethyl)-N-methylamino)propoxy]-6-methoxyquinazoline hydrochloride. ¹H NMR Spectrum (DMSO-$d_6$, CF$_3$COOD): 2.95(d, 3H); 3.2–3.55(m, 4H); 3.8(t, 2H); 4.02(s, 3H); 4.25(s, 2H); 4.5(m, 1H); 7.45(s, 1H); 7.5(d, 1H); 7.65(dd, 1H); 7.75(dd, 1H); 8.25(s, 1H); 8.9(s, 1H)

TABLE II-continued

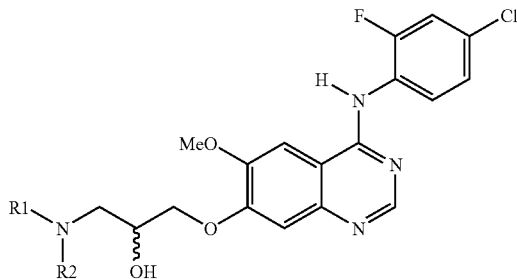

| Compound | R¹R²N | Weight (mg) | Yield (%) | MS-ESI [MH]⁺ | HPLC RT min | Note |
|---|---|---|---|---|---|---| e  4-(4-Chloro-2-fluorophenylamino)-7-(2,3-epoxypropoxy)-6-methoxyquinazoline was reacted with thiazolidine (58 mg) to give 4-(4-chloro-2-fluorophenylamino)-7-[2-hydroxy-3-(thiazolidin-1-yl)propoxy]-6-methoxyquinazoline hydrochloride. ¹H NMR Spectrum (DMSO-d₆, CF₃COOD): 3.25(t, 2H); 3.45–3.62(m, 2H); 3.7–3.9(m, 2H); 4.05(s, 3H); 4.28(d, 2H); 4.5(m, 1H); 4.6(m, 2H); 7.48(s, 1H); 7.5(d, 1H); 7.65(dd, 1H); 7.7(dd, 1H); 8.2(s, 1H); 8.9(s, 1H)

f  4-(4-Chloro-2-fluorophenylamino)-7-(2,3-epoxypropoxy)-6-methoxyquinazoline was reacted with 3-pyrroline (45 mg) to give 4-(4-chloro-2-fluorophenylamino)-7-[2-hydroxy-3-(3-pyrolin-1-yl)propoxy]-6-methoxyquinazoline hydrochloride. ¹H NMR Spectrum (DMSO-d₆, CF₃COOD): 3.4–3.6(m, 2H); 4.02(s, 3H); 4.15(d, 2H); 4.25(d, 2H); 4.35(dd, 2H); 4.40(m, 1H); 6.0(s, 2H); 7.45(s, 1H); 7.5(d, 1H); 7.67(dd, 1H); 7.7(d, 1H); 8.2(s, 1H); 8.9(s, 1H)

g  4-(4-Chloro-2-fluorophenylamino)-7-(2,3-epoxypropoxy)-6-methoxyquinazoline was reacted with thiomorpholine (67 mg) to give 4-(4-chloro-2-fluorophenylamino)-7-[2-hydroxy-3-(thiomorpholin-1-yl)propoxy]-6-methoxyquinazoline hydrochloride. ¹H NMR Spectrum (DMSO-d₆, CF₃COOD): 2.8–3.0(m, 2H); 3.1(t, 2H); 3.15–3.45(m, 4H); 3.5(d, 1H); 3.9(t, 2H); 4.05(s, 3H); 4.3(d, 1H); 4.55(m, 1H); 7.45(s, 1H); 7.5(d, 1H); 7.7–7.8(m, 2H); 8.25(s, 1H); 8.9(s, 1H)

h  4-(4-Chloro-2-fluorophenylamino)-7-(2,3-epoxypropoxy)-6-methoxyquinazoline was reacted with 3-hydroxypyrrolidine (57 mg) to give 4-(4-chloro-2-fluorophenylamino)-7-[2-hydroxy-3-(3-hydroxy-pyrrolidin-1-yl)propoxy]-6-methoxyquinazoline hydrochloride. ¹H NMR Spectrum (DMSO-d₆, CF₃COOD): 1.85–2.15(m, 2H); 3.1–3.5(m, 4H); 3.55–3.8(m, 2H); 4.02(s, 3H); 4.25(t, 2H); 4.4–4.55 (m, 2H); 7.45(s, 1H); 7.5(d, 1H); 7.7(dd, 1H); 7.75(dd, 1H); 8.15(s, 1H); 8.9(s, 1H)

i  4-(4-Chloro-2-fluorophenylamino)-7-(2,3-epoxypropoxy)-6-methoxyquinazoline was reacted with 1-(2-morpholinoethyl)-piperazine (130 mg) to give 4-(4-chloro-2-fluorophenylamino)-7-{2-hydroxy-3-[4-(2-morpholinoethyl)piperazin-1-yl]propoxy}-6-methoxyquinazoline hydrochloride. ¹H NMR Spectrum (DMSO-d₆, CF₃COOD): 3.25–3.75(m, 18H); 3.95(br s, 4H); 4.05(s, 3H); 4.3(d, 2H); 4.55(m, 1H); 7.48(s, 1H); 7.5(d, 1H); 7.62(dd, 1H); 7.68(dd, 1H); 8.2(s, 1H); 8.9(s, 1H)

j  4-(4-Chloro-2-fluorophenylamino)-7-(2,3-epoxypropoxy)-6-methoxyquinazoline was reacted with 1-(3-hydroxypropyl)-piperazine (94 mg) to give 4-(4-chloro-2-fluorophenylamino)-7-{2-hydroxy-3-[4-(3-hydroxypropyl)piperazin-1-yl]propoxy}-6-methoxyquinazoline hydrochloride. ¹H NMR Spectrum (DMSO-d₆, CF₃COOD): 1.8–1.9(m, 2H); 3.2–3.95(m, 14H); 4.02(s, 3H); 4.3(d, 2H); 4.55(m, 1H); 7.5(m, 2H); 7.65(dd, 1H); 7.7(dd, 1H); 8.25(s, 1H); 8.9(s, 1H)

k  4-(4-Chloro-2-fluorophenylamino)-7-(2,3-epoxypropoxy)-6-methoxyquinazoline was reacted with 1-(2-hydroxyethyl)-piperazine (85 mg) to give 4-(4-chloro-2-fluorophenylamino)-7-{2-hydroxy-3-[4-(2-hydroxyethyl)]piperazin-1-yl)propoxy}-6-methoxyquinazoline hydrochloride. ¹H NMR Spectrum (DMSO-d₆, CF₃COOD): 3.25–3.95(m, 14H); 4.05(s, 3H); 4.3(d, 2H); 4.55(m, 1H); 7.45(d, 1H); 7.5(s, 1H); 7.6–7.7(m, 2H); 8.3(s, 1H); 8.9(s, 1H)

l  4-(4-Chloro-2-fluorophenylamino)-7-(2,3-epoxypropoxy)-6-methoxyquinazoline was reacted with azetidine (37 mg) to give 4-(4-chloro-2-fluorophenylamino)-7-[2-hydroxy-3-(azetidin-1-yl)propoxy]-6-methoxyquinazoline hydrochloride.

m  4-(4-Chloro-2-fluorophenylamino)-7-(2,3-epoxypropoxy)-6-methoxyquinazoline was reacted with 2,5-dimethyl-3-pyrroline (63 mg) to give 4-(4-chloro-2-fluorophenylamino)-7-[2-hydroxy-3-(2,5-dimethyl-3-pyrrolin-1-yl)propoxy]-6-methoxyquinazoline hydrochloride.

n  4-(4-Chloro-2-fluorophenylamino)-7-(2,3-epoxypropoxy)-6-methoxyquinazoline was reacted with 4-methylpiperidine (64 mg) to give 4-(4-chloro-2-fluorophenylamino)-7-[2-hydroxy-3-(4-methylpiperidin-1-yl)propoxy]-6-methoxyquinazoline hydrochloride. ¹H NMR Spectrum(DMSO-d₆, CF₃COOD): 1.1(d, 3H); 1.35–1.75(m, 3H); 1.75–1.9(m, 2H); 3.1(td, 2H); 3.35(m, 2H); 3.5–3.65(m, 2H); 4.1(s, 3H); 4.3(d, 2H); 4.5(m, 1H); 7.45(s, 1H); 7.5(d, 1H); 7.65(dd, 1H); 7.7(d, 1H); 8.25(s, 1H); 8.9(s, 1H)

o  4-(4-Chloro-2-fluorophenylamino)-7-(2,3-epoxypropoxy)-6-methoxyquinazoline was reacted with N-(prop-2-yn-1-yl)-N-methylamine (45 mg) to give 4-(4-chloro-2-fluorophenylamino)-7-[2-hydroxy-3-(N-(prop-2-yn-1-yl)-N-methylamino)propoxy]-6-methoxyquinazoline hydrochloride. ¹H NMR Spectrum (DMSO-d₆): 2.9(s, 3H); 3.3–3.4(m, 2H); 3.9(s, 1H); 4.0(s, 3H); 4.19(s, 2H); 4.25(d, 2H); 4.42 (m, 1H); 6.15(br s, 1H); 7.4(s, 1H); 7.42(d, 1H); 7.6(dd, 1H); 7.65(d, 1H); 8.25(br s, 1H); 8.7(br s, 1H)

TABLE II-continued

|  |  | Weight | Yield | MS-ESI | HPLC RT |  |
|---|---|---|---|---|---|---|
| Compound | R¹R²N | (mg) | (%) | [MH]⁺ | min | Note | p 4-(4-Chloro-2-fluorophenylamino)-7-(2,3-epoxypropoxy)-6-methoxyquinazoline was reacted with 2-methylpyrrolidine (55 mg) to give 4-(4-chloro-2-fluorophenylamino)-7-[2-hydroxy-3-(2-methylpyrrolidin-1-yl)propoxy]-6-methoxyquinazoline hydrochloride. $^1$H NMR Spectrum (DMSO-d$_6$, CF$_3$COOD): 1.4(2d, 3H); 1.6–1.8(m, 1H); 1.9–2.1(m, 2H); 2.15–2.3(m, 1H); 3.15–3.35(m, 2H); 3.4–3.5(m, 1H); 3.5–3.7(m, 1H); 3.7–3.8(m, 1H); 4.05(s, 3H); 4.25(br s, 2H); 4.3–4.5(m, 1H); 7.45(d, 1H); 7.5(d, 1H); 7.62(dd, 1H); 7.7(d, 1H); 8.12(s, 1H); 8.95(s, 1H)

q 4-(4-Chloro-2-fluorophenylamino)-7-(2,3-epoxypropoxy)-6-methoxyquinazoline was reacted with N-isopropyl-N-ethylamine (57 mg) to give 4-(4-chloro-2-fluorophenylamino)-7-[2-hydroxy-3-(N-isopropyl-N-ethylamino)propoxy]-6-methoxyquinazoline hydrochloride. $^1$H NMR Spectrum (DMSO-d$_6$, CF$_3$COOD): 1.25–1.37(m, 9H); 3.1–3.45(m, 4H); 3.75(m, 1H); 4.05(s, 3H); 4.3(m, 2H); 4.4(m, 1H); 7.45(s, 1H); 7.47(d, 1H); 7.62(dd, 1H); 7.68(d, 1H); 8.22(s, 1H); 8.9(s, 1H)

r 4-(4-Chloro-2-fluorophenylamino)-7-(2,3-epoxypropoxy)-6-methoxyquinazoline was reacted with N-methyl-Beta-alaninenitrile (55 mg) to give 4-(4-chloro-2-fluorophenylamino)-7-[2-hydroxy-3-(N-(2-cyanoethyl)-N-methylamino)propoxy]-6-methoxyquinazoline hydrochloride. $^1$H NMR Spectrum (DMSO-d$_6$, CF$_3$COOD): 2.95(br s, 3H); 3.15(br s, 2H); 3.4(br s, 2H); 3.6(br s, 2H); 4.05(s, 3H); 4.25 (d, 2H); 4.5(br s, 1H); 7.45(s, 1H); 7.47(d, 1H); 7.6–7.72(m, 2H); 8.25(s, 1H); 8.9(s, 1H)

s 4-(4-Chloro-2-fluorophenylamino)-7-(2,3-epoxypropoxy)-6-methoxyquinazoline was reacted with N-isopropyl-N-methylamine (48 mg) to give 4-(4-chloro-2-fluorophenylamino)-7-[2-hydroxy-3-(N-isopropyl-N-methylamino)propoxy]-6-methoxyquinazoline hydrochloride. $^1$H NMR Spectrum(DMSO-d$_6$, CF$_3$COOD): 1.3(m, 6H); 2.8(s, 3H); 3.05–3.5(m, 2H); 3.5–3.75(m, 1H); 4.05(s, 3H); 4.25(d, 2H); 4.45(br s, 1H); 7.4–7.55(m, 2H); 7.65(dd, 1H); 7.7(dd, 1H); 8.22(s, 1H); 8.95(s, 1H)

t 4-(4-Chloro-2-fluorophenylamino)-7-(2,3-epoxypropoxy)-6-methoxyquinazoline was reacted with N-isobutyl-N-methylamine (57 mg) to give 4-(4-chloro-2-fluorophenylamino)-7-[2-hydroxy-3-(N-isobutyl-N-methylamino)propoxy]-6-methoxyquinazoline hydrochloride. $^1$H NMR Spectrum (DMSO-d$_6$, CF$_3$COOD): 1.0(m, 6H); 2.15(m, 1H); 2.95(s, 3H); 3.0(m, 1H); 3.05–3.35(m, 2H); 3.35–3.5(m, 1H); 4.02(s, 3H); 4.25(br s, 2H); 4.5(m, 1H); 7.45(d, 1H); 7.5(s, 1H); 7.70(dd, 1H); 7.85(d, 1H); 8.25 (s, 1H); 8.9(s, 1H)

u 4-(4-Chloro-2-fluorophenylamino)-7-(2,3-epoxypropoxy)-6-methoxyquinazoline was reacted with N-(n-propyl)-N-ethyl (57 mg) to give 4-(4-chloro-2-fluorophenylamino)-7-[2-hydroxy-3-(N-(n-propyl)-N-ethylamino)propoxy]-6-methoxyquinazoline hydrochloride. $^1$H NMR Spectrum (DMSO-d$_6$, CF$_3$COOD): 1.0(m, 3H); 1.25(t, 3H); 1.75(m, 2H); 3.05–3.2(m, 2H); 3.2–3.4(m, 4H); 4.02(s, 3H); 4.25(s, 2H); 4.5(br s, 1H); 7.4(s, 1H); 7.45(d, 1H); 7.6–7.75(m, 2H); 8.25(s, 1H); 8.9(s, 1H)

EXAMPLE 8

4-(4-Bromo-2-fluorophenylamino)-7-[2-hydroxy-3-(4-pyridylsulphanyl)propoxy]-6-methoxyquinazoline 4-Mercaptopyridine (93 mg) was added to a suspension of sodium hydride 60% (12 mg) in DMF (2 ml) under nitrogen. After stirring for 15 minutes 4-(4-bromo-2-fluorophenylamino)-7-(2,3-epoxypropoxy)-6-methoxyquinazoline (100 mg) (from Example 5) was added and the mixture was stirred for 3 hours at ambient temperature. The volatiles were removed under vacuum. The residue was partitioned between methylene chloride and water and the pH of the aqueous layer was adjusted to 7 with 1N HCl. The organic layer was separated, washed with water, followed by brine, dried (MgSO$_4$) and evaporated to give 4-(4-bromo-2-fluorophenylamino)-7-[2-hydroxy-3-(4-pyridylsulphanyl)propoxy]-6-methoxyquinazoline (20 mg).

$^1$H NMR Spectrum: (DMSOd$_6$) 3.2 (dd, 2H), 4.0 (s, 3H), 4.15 (m, 1H), 4.22 (d, 2H), 5.7 (d, 1H), 7.22 (s, 1H), 7.32 (d, 2H), 7.5 (d, 1H), 755 (dd, 1H), 7.68 (dd, 1H), 7.85 (s, 1H), 8.4 (d, 2H), 8.4 (s, 1H), 9.6 (s, 1H)

Mass Spectrum M$^-$H$^-$529 and 531

EXAMPLE 9

4-(4-Bromo-2-fluorophenylamino)-7-[2-hydroxy-3-(1-methylimidazol-2-ylsulphanyl)propoxy]-6-methoxyquinazoline

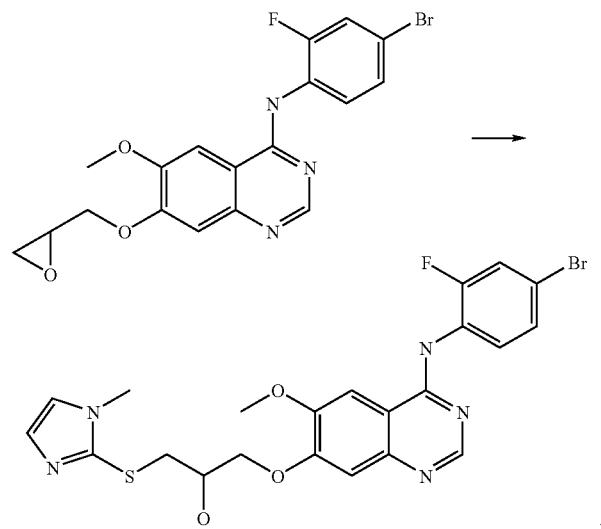

Using a procedure similar to that described for the preparation of Example 8,4-(4-bromo-2-fluorophenylamino)-7-(2,3-epoxypropoxy)-6-methoxyquinazoline (100 mg) (from Example 5) was reacted with 2-mercapto-1-methylimidazole (32.6 mg) to give 4-(4-bromo-2-fluorophenylamino)-7-[2-hydroxy-3-(1-methylimidazol-2-ylsulphanyl)propoxy]-6-methoxyquinazoline (65 ng).

$^1$H NMR Spectrum: (DMSOd$_6$) 3.15–3.35 (m, 2H), 3.6 (s, 3H), 3.95 (s, 3H), 4.1–4.25 (m, 3H), 5.8 (d, 1H), 6.95 (s, 1H), 7.2 (s, 1H), 7.25 (s, 1H), 7.5 (d, 1H), 7.55 (dd, 1H), 7.7 (d, 1H), 7.82 (s, 1H), 8.38 (s, 1H), 9.6 (br s, 1H)

Mass Spectrum: M$^+$H$^+$ 534.4 and 536.4

EXAMPLE 10

4-Chloro-2-fluoro-5-hydroxyphenylamino-7-[2-hydroxy-3-(pyrrolidin-1-yl)propoxy]-6-methoxyquinazoline

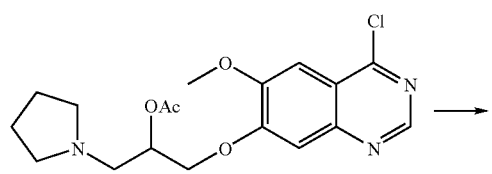

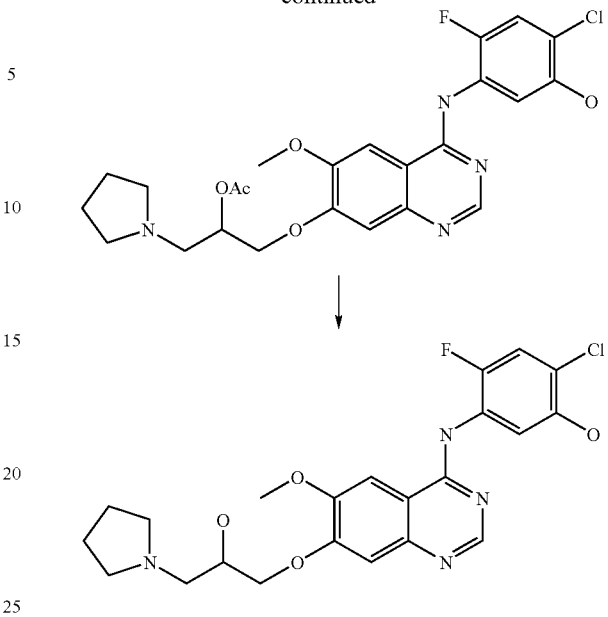

A suspension of 4-chloro-2-fluoro-5-hydroxyphenylamino-7-[2-acetoxy-3-(pyrrolidin-1-yl)propoxy]-6-methoxyquinazoline (170 mg) in methanol saturated with ammonia (6 ml) was stirred at ambient temperature for 2 hours. The volatiles were removed under vacuum. The residue was partitioned between ethyl acetate and water. The pH of the aqueous layer was adjusted to 6.5. The organic layer was separated, washed with water, dried (MgSO$_4$) and evaporated. The residue was triturated under diethyl ether, filtered, washed with ether and dried under vacuum to give 4-chloro-2-fluoro-5-hydroxyphenylamino-7-[2-hydroxy-3-(pyrrolidin-1-yl)propoxy]-6-methoxyquinazoline (20 mg).

$^1$H NMR Spectrum: (DMSOd$_6$, CF$_3$COOD) 1.9–2.0 (m, 2H), 2.0–2.1 (m, 2H), 3.1–3.2 (m, 2H), 3.4 (m, 2H), 3.6–3.7 (m, 2H), 4.03 (s, 3H), 4.25 (d, 2H), 4.4 (m, 1H), 7.15 (d, 1H), 7.42 (s, 1H), 7.55 (d, 1H), 8.1 (s, 1H), 8.9 (s, 1H)

Mass Spectrum: M$^+$H$^+$ 463.55

The starting material was prepared as follows:

A mixture of 7-hydroxy-6-methoxy-3-((pivaloyloxy)methyl)-3,4-dihydroquinazolin-4-one (40 g), (from Example 1), in DMF (400 ml) and potassium carbonate (36 g) was stirred at ambient temperature for 10 minutes then epibromohydrin (16.8 ml) was added and the reaction mixture heated at 70° C. for 1.5 hours. The mixture was poured onto ice/water (1.5 l) under stirring. The precipitate was collected by filtration, washed with water (1.6 l) and ether (500 ml) and dried under vacuum over phosphorus pentoxide to give the desired epoxide (46.7 g).

A portion of the above epoxide (8 g) was dissolved in chloroform (120 ml) and pyrrolidine (1.98 ml) was added. The reaction mixture was heated at reflux overnight, the solvent was evaporated and the crude product purified by flash chromatography using dichloromethane/methanol (95:5 an up to 40:60) as eluent. Evaporation of the solvent and trituration in ether/petroleum ether (1:1) gave 7-(2-hydroxy-3-(pyrrolidin-1-yl)propoxy)-6-methoxy-1-((pivaloyloxy)methyl)-3,4-dihydroquinazolin-4-one (7.8 g) as a white foam.

7-(2-Hydroxy-3-(pyrrolidin-1-yl)propoxy)-6-methoxy-3-((pivaloyloxy)methyl)-3,4-dihydroquinazolin-4-one (7.8 g) was stirred for 48 hours in a solution of methanol saturated with ammonia (200 ml). The solvent was evaporated and the solid obtained was washed with ether (2×) and ether/dichloromethane (95:5, 2×100 ml) to give the 7-(2-hydroxy-3-(pyrrolidin-1-yl)propoxy)-6-methoxy-3,4-dihydroquinazolin-4-one (5.5 g).

7-(2-Hydroxy-3-(pyrrolidin-1-yl)propoxy)-6-methoxy-3,4-dihydroquinazolin-4-one (5 g) was suspended in acetic anhydride (7.4 ml). The reaction mixture was stirred at ambient temperature for 90 minutes followed by addition of water (2.8 ml) and the reaction mixture was stirred an additional 2 hours in order to hydrolyse the diacetate byproduct. The mixture was cooled with an ice bath, more water (100 ml) was added and a solution of sodium hydroxide (2N) was slowly added to adjust the pH to 9.5. The product was extracted with dichloromethane (3 times) the organic phases were combined, washed with water, brine, dried over magnesium sulphate, filtered and the solvent evaporated to give 7-(2-acetoxy-3-(pyrrolidin-1-yl)propoxy)-6-methoxy-3,4-dihydroquinazolin-4-one (4.2 g) as a white solid.

7-(2-Acetoxy-3-(pyrrolidin-1-yl)propoxy)-6-methoxy-3,4-dihydroquinazolin-4-one (4.7 g) was suspended in thionyl chloride (55 ml), DMF (0.5 ml) was added and the mixture heated at reflux for 1 hour. The thionyl chloride was evaporated under vacuum, toluene was added and the solvent was evaporated. This process was repeated twice. The residue was taken up in ice/water, the pH adjusted to 7.5 with a saturated solution of sodium bicarbonate followed by sodium hydroxide 2N until pH 9 and the aqueous solution extracted twice with dichloromethane. The combined extracts were washed with water and brine, dried over magnesium sulphate and filtered. The filtrate was evaporated under vacuum and the residue triturated with ether to give 4-chloro-7-[2-acetoxy-3-(pyrrolidin-1-yl)propoxy]-6-methoxyquinazoline (4.1 g) as a white foam.

$^1$H NMR Spectrum: (CDCl$_3$+4 drops CD3COOD) 2.05 (s, 4H), 2.15 (s, 3H), 3.45 (br s, 4H), 3.65 (m, 2H), 4.05 (s, 3H), 4.4 (d, 2H), 5.65 (m, 1H), 7.4 (s, 1H), 7.55 (s, 1H), 8.9 (s, 1H).

A suspension of 4-chloro-7-[2-acetoxy-3-(pyrrolidin-1-yl)propoxy]-6-methoxyquinazoline (120 mg) and 4-chloro-2-fluoro-5-hydroxyaniline (56 mg), (as described in EP 61741 A2), in isopropanol (6 ml) containing G hydrogen chloride in isopropanol (58 μl) was stirred at 80° C. for 1.5 hours. After cooling ether (1 ml) was added and the precipitate was filtered, washed with ether and dried under vacuum to give 4-chloro-2-fluoro-5-hydroxyphenylamino-7-[2-acetoxy-3-(pyrrolidin-1-yl)propoxy]-6-methoxyquinazoline (170 mg).

$^1$H NMR Spectrum: (DMSOd$_6$) 1.9–2.0 (m, 2H), 2.0–2.1 (m, 2H), 2.18 (s, 3H), 3.1–3.25 (m, 2H), 3.5–3.7 (m, 4H), 4.05 (s, 3H), 4.4–4.55 (m, 2H), 5.6 (m, 1H), 7.2 (d, 1H), 7.42 (s, 1H), 7.55 (d, 1H), 8.3 (s, 1H), 8.8 (s, 1H)

EXAMPLE 11

4-Chloro-2-fluoro-5-hydroxyphenylamino-7-(2-acetoxy-3-piperidinopropoxy-6-methoxyquinazoline

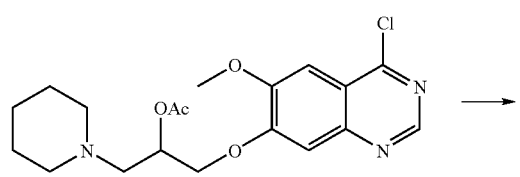

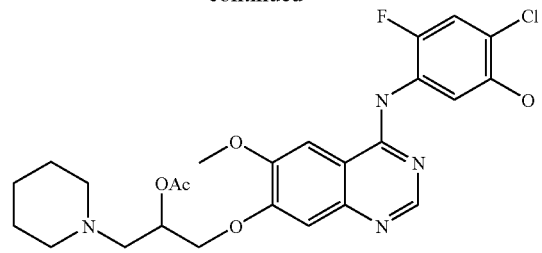

Using an analogous procedure to that described in Example 10, 4-chloro-7-(2-acetoxy-3-piperidinopropoxy)-6-methoxyquinazoline (120 mg) was reacted with 2-fluoro-4-chloro-5-hydroxyaniline (54 mg), (as described in EP 61741 A2), to give 4-chloro-2-fluoro-5-hydroxyphenylamino-7-(2-acetoxy-3-piperidinopropoxy)-6-methoxyquinazoline (160 mg).

$^1$H NMR Spectrum: (DMSOd$_6$) 1.3–1.5 (m, 1H), 1.6–1.9 (m, 5H), 2.15 (s, 3H), 2.9–3.1 (m, 2H), 3.4–3.6 (m, 4H), 4.05 (s, 3H), 4.4–4.5 (m, 2H), 5.65 (m, 1H), 7.2 (d, 1H), 7.42 (s, 1H), 7.55 (d, 1H), 8.32 (s, 1H), 8.8 (s, 1H)

Mass Spectrum: M$^+$H$^+$ 519.6 and 521.6

The starting material was prepared as follows:

Using an analogous procedure to that described in Example 10, 4-chloro-7-(2-acetoxy-3-piperidinopropoxy)-6-methoxyquinazoline was made.

$^1$H NMR Spectrum: (CDCl$_3$+4 drops CD$_3$COOD) 1.6 (m, 2H), 1.9 (m, 4H), 2.1 (s, 3H), 3.2 (br s, 4H), 3.5 (m, 2H), 4.05 (s, 3H), 4.35 (m, 2H), 5.7 (m, 1H), 7.4 (s, 1H), 7.5 (s, 1H), 8.9 (s, 1H)

EXAMPLES 12 AND 13

4-Bromo-2-fluoro-5-hydroxyphenylamino-7-[2-acetoxy-3-(pyrrolidin-1-yl)propoxy]-6-methoxyquinazoline 4-Bromo-2-fluoro-5-hydroxyphenylamino-7-[-hydroxy-3-(pyrrolidin-1-yl)propoxy]-6-methoxyquinazoline

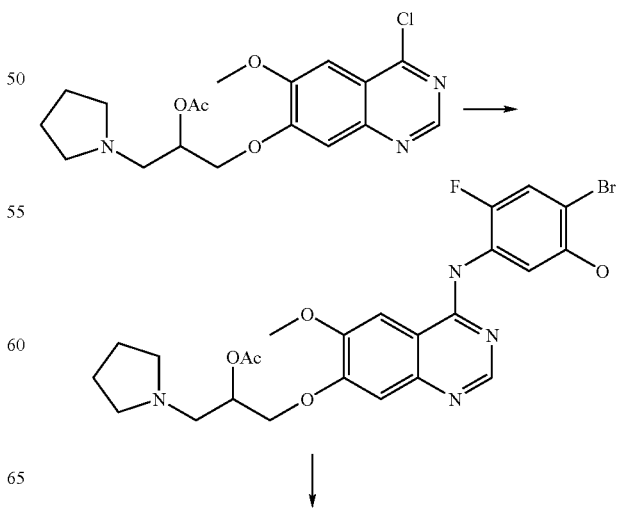

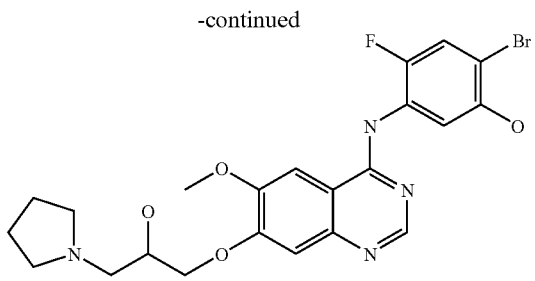

Using an analogous procedure to that described in Example 11, 4-chloro-7-[2-acetoxy-3-(pyrrolidin-1-yl)propoxy]-6-methoxyquinazoline (120 mg), (from Example 10), was reacted with 2-fluoro-4-bromo-5-hydroxyaniline (71 mg), (as described in EP 61741 A2), to give 4-bromo-2-fluoro-5-hydroxyphenylamino-7-[2-acetoxy-3-(pyrrolidin-1-yl)propoxy]-6-methoxyquinazoline (135 mg).

$^1$H NMR Spectrum (DMSOd$_6$, CF$_3$COOD) 1.9–2.0 (m, 2H), 2.05–2.15 (m, 2H), 2.15 (s, 3H), 3.15–3.25 (m, 2H), 3.6–3.8 (m, 4H), 4.05 (s, 3H), 4.4–4.6 (m, 2H), 5.65 (m, 1H), 7.2 (d, 1H), 7.42 (s, 1H), 7.62 (d, 1H), 8.2 (s, 1H), 8.9 (s, 1H)

Mass Spectrum: M$^+$H$^+$ 549.49 and 551.5

Using an analogous procedure to that described in Example 10, 4-bromo-2-fluoro-5-hydroxyphenylamino-7-[2-acetoxy-3-(pyrrolidin-1-yl)propoxy]-6-methoxyquinazoline (106 mg) was treated with methanol saturated with ammonia to give 4-bromo-2-fluoro-5-hydroxyphenylamino-7-[2-hydroxy-3-(pyrrolidin-1-yl)propoxy]-6-methoxyquinazoline (68 mg)

$^1$H NMR Spectrum (DMSOd$_6$, CF$_3$COOD) 1.9–2.0 (m, 2H), 2.1–2.2 (m, 2H), 3.1–3.25 (m, 2H), 3.4 (d, 2H), 3.6–3.7 (m, 2H), 4.05 (s, 3H), 4.25 (d, 1H), 4.4 (m, 1H), 7.2 (d, 1H), 7.45 (s, 1H), 7.65 (d, 1H), 8.2 (s, 1H), 8.9 (s, 1H)

Mass Spectrum M$^+$H$^+$ 507.47 and 509.47

EXAMPLE 14

The following illustrate representative pharmaceutical dosage forms containing the compound of formula I, or a pharmaceutically acceptable salt thereof (hereafter compound X), for therapeutic or prophylactic use in humans:

| (a) | Tablet I | mg/tablet |
|---|---|---|
| | Compound X | 100 |
| | Lactose Ph. Eur | 182.75 |
| | Croscarmellose sodium | 12.0 |
| | Maize starch paste (5% w/v paste) | 2.25 |
| | Magnesium stearate | 3.0 |
| (b) | Tablet II | mg/tablet |
| | Compound X | 50 |
| | Lactose Ph. Eur | 223.75 |
| | Croscamellose sodium | 6.0 |
| | Maize starch | 15.0 |
| | Polyvinylpyrrolidone (5% w/v paste) | 2.25 |
| | Magnesium stearate | 3.0 |
| (c) | Tablet III | mg/tablet |
| | Compound X | 1.0 |
| | Lactose Ph. Eur | 93.25 |
| | Croscarmellose sodium | 4.0 |
| | Maize starch paste (5% w/v paste) | 0.75 |
| | Magnesium stearate | 1.0 |
| (d) | Capsule | mg/capsule |
| | Compound X | 10 |
| | Lactose Ph. Eur | 488.5 |
| | Magnesium stearate | 1.5 |
| (e) | Injection I | (50 mg/ml) |
| | Compound X | 5.0% w/v |
| | 1 N Sodium hydroxide solution | 15.0% v/v |
| | 0.1 N Hydrochloric acid (to adjust pH to 7.6) | |
| | Polyethylene glycol 400 | 4.5% w/v |
| | Water for injection to 100% | |
| (f) | Injection II | 10 mg/ml |
| | Compound X | 1.0% w/v |
| | Sodium phosphate BP | 3.6% w/v |
| | 0.1 N Sodium hydroxide solution | 15.0% v/v |
| | Water for injection to 100% | |
| (g) | Injection III | (1 mg/ml, buffered to pH 6) |
| | Compound X | 0.1% w/v |
| | Sodium phosphate BP | 2.26%w/v |
| | Citric acid | 0.38%w/v |
| | Polyethylene glycol 400 | 3.5% w/v |
| | Water for injection to 100% | |

Note

The above formulations may be obtained by conventional procedures well known in the pharmaceutical art. The tablets (a)–(c) may be enteric coated by conventional means, for example to provide a coating of cellulose acetate phthalate.

The invention claimed is:

1. A compound of the formula (I):

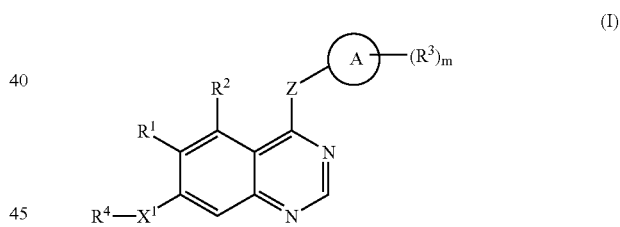

[wherein:
ring A is phenyl;
Z is —O—, —NH— or —S—;
m is an integer from 0 to 5 inclusive;
R$^1$ is hydrogen, hydroxy, halogeno, nitro, trifluoromethyl, cyano, C$_{1-3}$alkyl, C$_{1-3}$alkoxy, C$_{1-3}$alkylthio, or —NR$^5$R$^6$ (wherein R$^5$ and R$^6$, which may be the same or different, are hydrogen or C$_{1-3}$alkyl);
R$^2$ is hydrogen, hydroxy, halogeno, C$_{1-3}$alkyl, C$_{1-3}$alkoxy, trifluoromethyl, amino or nitro;
R$^3$ is hydroxy, halogeno, C$_{1-3}$alkyl, C$_{1-3}$alkoxy, C$_{1-3}$alkanoyloxy, trifluoromethyl, cyano, amino or nitro;
X$^1$ is —O—, —CH$_2$—, —S—, —SO—, —SO$_2$—, —NR$^7$—, —NR$^7$CO—, —CONR$^7$—, —SO$_2$NR$^7$— or —NR$^7$SO$_2$—, (wherein R$^7$ is hydrogen, C$_{1-3}$alkyl or C$_{1-3}$alkoxyC$_{2-3}$alkyl);
R$^4$ is selected from one of the following groups:
1) —Y$^1$X$^2$COR$^8$ [wherein —Y$^1$— is a C$_{2-5}$alkylene chain wherein each methylene group (other than that of the α-carbon) is optionally substituted by 1 substituent independently selected from hydroxy, halogeno, amino and $C_{1-4}$alkanoyloxy, provided that there is at least 1 and no more than 3 substituents on the $C_{2-5}$alkylene chain; $X^2$ is —O— or —$NR^9$— (in which $R^9$ is hydrogen, $C_{1-3}$alkyl or $C_{1-3}$alkoxy$C_{2-3}$alkyl) and $R^8$ is $C_{1-3}$alkyl, —$NR^{10}R^{11}$ or —$OR^{12}$ (wherein $R^{10}$, $R^{11}$ and $R^{12}$, which may be the same or different, are hydrogen, $C_{1-3}$alkyl or $C_{1-3}$alkoxy$C_{2-3}$alkyl)];

2) —$Y^2$—$X^3R^{13}$ [wherein $Y^2$ is $C_{2-5}$alkylene, $C_{3-5}$alkenylene or $C_{3-5}$alkynylene wherein each methylene group (other than that of the α-carbon) is optionally substituted by 1 substituent independently selected from hydroxy, halogeno, amino and $C_{1-4}$alkanoyloxy, provided that there is at least 1 substituent and no more than 3 substituents on the alkylene, alkenylene or alkynylene chain; $X^3$ is —O—, —S—, —SO—, —$SO_2$—, —OCO—, —$NR^7CO$—, —$CONR^7$—, —$SO_2NR^7$—, —$NR^7SO_2$— or —$NR^7$— (wherein $R^7$ is as defined above) and $R^{13}$ is hydrogen or $C_{1-3}$alkyl, wherein the $C_{1-3}$alkyl group may bear one or two substituents selected from oxo, hydroxy, halogeno and $C_{1-4}$alkoxy;

3) —$Y^1$—$X^6C_{1-5}$alkyl$R^{14}$ [wherein $Y^1$ is as defined above and $X^6$ is —O—, —S—, —SO—, —$SO_2$—, —$NR^7CO$—, —$CONR^7$—, —$SO_2NR^7$—, —$NR^7SO_2$— or —$NR^7$— (wherein $R^7$ is as defined above) and $R^{14}$ is $C_{3-7}$cycloalkyl or a 3 to 7 membered saturated or partially saturated heterocyclic group containing up to 3 ring heteroatoms selected independently from O, S and N, wherein the carbocyclic or heterocyclic group is optionally substituted by one or two substituents selected from oxo, hydroxy, halogeno, $C_{1-4}$alkyl, (wherein the $C_{1-4}$alkyl group is optionally substituted by 1 or 2 substituents selected from hydroxy, cyano, halogeno, amino, nitro, morpholino, $C_{3-5}$cycloalkyl, piperidin-1-yl and piperazin-1-yl), $C_{2-4}$alkenyl, $C_{2-4}$alkynyl, $C_{1-4}$hydroxyalkyl, $C_{1-4}$alkoxy, carbamoyl, $C_{1-3}$alkylcarbamoyl, N,N-di($C_{1-3}$alkyl)carbamoyl, $C_{2-4}$alkanoyl, $C_{1-4}$alkoxycarbonyl, $C_{1-4}$alkylthio, $C_{1-4}$alkylsulphinyl, $C_{1-4}$alkylsulphonyl, $C_{2-4}$alkanoylamino, N—$C_{1-3}$alkyl-$C_{2-4}$alkanoylamino, N—$C_{1-3}$alkylsulphamoyl, N,N-di-[$C_{1-3}$alkyl]sulphamoyl, $C_{1-3}$alkanesulphonylamino and N—$C_{1-3}$alkyl-$C_{1-3}$alkanesulphonylamino, or $R^{14}$ is a pyridone group, a phenyl group or a 5 or 6-membered aromatic heterocyclic group containing 1 to 3 ring heteroatoms independently selected from O, N and S, and wherein the pyridone, phenyl or heterocyclic group is optionally substituted by up to 5 substituents selected from halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, $C_{1-4}$alkylthio, $C_{1-4}$alkylsulphinyl, $C_{1-4}$alkylsulphonyl, N—$C_{1-3}$alkylsulphamoyl, N,N-di-[$C_{1-3}$alkyl]sulphamoyl, $C_{1-3}$alkanesulphonylamino, N—$C_{1-3}$alkyl-$C_{1-3}$alkanesulphonylamino, —$CONR^{10}R^{11}$ and —$NR^{10}COR^{11}$ (wherein $R^{10}$ and $R^{11}$ are as defined above)];

4) —$Y^1$—$X^4C_{1-5}$alkyl$X^5R^{15}$ [wherein $Y^1$ is as defined above and $X^4$ and $X^5$ which may be the same or different are each —O—, —S—, —SO—, —$SO_2$—, —$NR^7CO$—, —$CONR^7$—, —$SO_2NR^7$—, —$NR^7SO_2$— or —$NR^7$— (wherein $R^7$ is as defined above and $R^{15}$ is hydrogen or $C_{1-3}$alkyl)];

5) —$Y^1$—O—$C_{1-3}$alkyl (wherein $Y^1$ is as defined above) provided that $X^1$ is —O—, —S—, —SO— or —$SO_2$—;

6) —$Y^2$—$R^{16}$ {wherein —$Y^2$— is as defined above and $R^{16}$ is a saturated or partially saturated 3 to 7 membered heterocyclic ring containing up to 3 heteroatoms selected from O, S and N [wherein the heterocyclic ring is optionally substituted by up to 3 substitutents selected from oxo, hydroxy, halogeno, $C_{1-4}$alkyl, $C_{2-4}$alkenyl, $C_{2-4}$alkynyl and $C_{3-7}$cycloalkyl (wherein $C_{1-4}$alkyl, $C_{2-4}$alkenyl, $C_{2-4}$alkynyl and $C_{3-7}$cycloalkyl are themselves optionally substituted by up to 3 substituents selected from hydroxy, halogeno, cyano, $C_{1-3}$alkyl, $C_{1-3}$alkoxy, $C_{1-3}$alkanoyloxy, trifluoromethyl, amino, nitro and $R^{14}$ as defined above), $C_{1-4}$alkoxy, carbamoyl, $C_{1-4}$alkylcarbamoyl, N—N-di($C_{1-4}$alkyl)carbamoyl, $C_{2-4}$alkanoyl, $C_{1-4}$alkoxycarbonyl, $C_{3-7}$cycloalkyl, $C_{1-4}$alkylthio, $C_{1-4}$alkylsulphinyl, $C_{1-4}$alkylsulphonyl, $C_{2-4}$alkanoylamino, N—$C_{1-3}$alkyl-$C_{2-4}$alkanoylamino, N—$C_{1-3}$alkylsulphamoyl, N,N-di-[$C_{1-3}$alkyl]sulphamoyl, $C_{1-3}$alkanesulphonylamino and N—$C_{1-3}$alkyl-$C_{1-3}$alkanesulphonylamino or $R^{16}$ is a pyridone group, a phenyl group or a 5 or 6-membered aromatic heterocyclic group containing 1 to 3 ring heteroatoms independently selected from O, N and S, and wherein the pyridone, phenyl or heterocyclic group is optionally substituted by up to 5 substituents selected from halogeno, amino, $C_{1-4}$alkyl, $C_{1-4}$alkoxy, $C_{1-4}$hydroxyalkyl, $C_{1-4}$aminoalkyl, $C_{1-4}$alkylamino, $C_{1-4}$hydroxyalkoxy, carboxy, cyano, $C_{1-4}$alkylthio, $C_{1-4}$alkylsulphinyl, $C_{1-4}$alkylsulphonyl, N—$C_{1-3}$alkylsulphamoyl, N,N-di-[$C_{1-3}$alkyl]sulphamoyl, $C_{1-3}$alkanesulphonylamino, N—$C_{1-3}$alkyl-$C_{1-3}$alkanesulphonylamino, —$CONR^{10}R^{11}$ and —$NR^{10}COR^{11}$ (wherein $R^{10}$ and $R^{11}$ (as defined above)];

7) —$Y^2$—$X^6$—$R^{14}$ (wherein $Y^2$, $X^6$ and $R^{14}$ are as defined above); and 8) —$Y^2$—$NR^{17}R^{18}$ [wherein $Y^2$ is as defined above and $R^{17}$ and $R^{18}$ are independently selected from hydrogen, $C_{1-6}$alkyl, $C_{2-6}$alkenyl, $C_{2-6}$alkynyl or $C_{1-3}$alkoxy$C_{1-6}$alkyl (wherein any alkyl group in $R^{17}$ or $R^{18}$ is optionally substituted by up to 2 substituents selected from hydroxy, halogeno, $C_{1-3}$alkyl, $C_{1-3}$alkoxy, $C_{1-3}$alkanoyloxy, trifluoromethyl, cyano, amino or nitro)];

9) —$Y^3R^a$ (wherein $Y^3$ is $C_{1-5}$alkylene, $C_{2-5}$alkenylene or $C_{2-5}$alkynylene wherein each methylene group (other than that of the α-carbon) is optionally substituted by 1 substituent independently selected from hydroxy, halogeno, amino and $C_{1-4}$alkanoyloxy, provided that there are no more than 3 substituents on the alkylene, alkenylene or alkynylene chain; and $R^a$ is $C_{3-7}$cycloalkyl which is substituted by 1 substituent selected from hydroxy, amino and halogeno on the ring carbon lied to $Y^3$ and additionally optionally substituted by up to 3 substitutents selected from oxo, hydroxy, halogeno, $C_{1-4}$alkyl, $C_{2-4}$alkenyl, $C_{2-4}$alkynyl, $C_{1-4}$alkoxy, carbamoyl, $C_{1-4}$alkylcarbamoyl, N—N-di($C_{1-4}$alkyl)carbamoyl, $C_{2-4}$alkanoyl, $C_{1-4}$alkoxycarbonyl and $C_{3-7}$cycloalkyl (wherein $C_{1-4}$alkyl, $C_{2-4}$alkenyl, $C_{2-4}$alkynyl and $C_{3-7}$cycloalkyl are themselves optionally substituted by up to 3 substituents selected from hydroxy, halogeno, cyano, $C_{1-3}$alkyl, $C_{1-3}$alkoxy, $C_{1-3}$alkanoyloxy, trifluoromethyl, cyano, amino, nitro and $R^{14}$ as defined above)];

provided that when:

m is an integer from 1 to 3,
$R^1$ is methoxy; $R^2$ is hydrogen; Z is —NH—;
$R^3$ is halogeno or $C_{1-3}$alkyl; and
$X^1$ is —O—; then
$R^4$ is not selected from one of the following three groups:
  a) —$C_{2-5}$alkyl$R^{19}$ (wherein $R^{19}$ is piperidin-4-yl which may bear one or two substituents selected from hydroxy, halogeno, $C_{1-4}$alkyl, $C_{1-4}$hydroxyalkyl and $C_{1-4}$alkoxy);
  b) —$C_{2-5}$alkenyl$R^{19}$ (wherein $R^{19}$ is as defined above);
  c) —$C_{2-5}$alkynyl$R^{19}$ (wherein $R^{19}$ is as defined above);
  wherein any alkylene, alkenylene or alkynylene chain in groups a) to c) above are optionally substituted by one or more substituents selected from hydroxy, halogeno and amino;

or a salt thereof.

2. A compound according to claim 1 wherein $R^2$ is hydrogen.

3. A compound according to claim 1 or claim 2 wherein $R^1$ is hydrogen or methoxy.

4. A compound according to claim 1 wherein $R^3$ is hydroxy, halogeno, $C_{1-2}$alkyl, $C_{1-2}$alkoxy, trifluoromethyl, cyano, amino or nitro.

5. A compound according to claim 1 wherein m is 2 or 3.

6. A compound according to claim 1 wherein ring A bearing bearing $(R^3)_m$ is 2-fluoro-4-chloro-5-hydroxyphenyl, 2-fluoro-4-bromo-5-hydroxyphenyl, 2-fluoro-4-chlorophenyl or 2-fluoro-4-bromophenyl.

7. A compound according to claim 1 wherein $X^1$ is —O—, —S—, —$NR^7CO$— or —$NR^7SO_2$— (wherein $R^7$ is hydrogen, methyl or ethyl).

8. A compound according to claim 1 wherein $R^4$ is of the formula —$Y^2$—$R^{16}$, —$Y^2$—$NR^{17}R^{18}$ or —$Y^3$—$R^a$, wherein $Y^2$, $Y^3$, $R^a$, $R^{16}$, $R^{17}$ and $R^{18}$ are as defined in claim 1.

9. A compound according to claim 1 wherein the alkylene, alkenylene or alkynylene chain in $Y^1$ or $Y^2$ in $R^4$ is substitued by hydroxy or acetoxy, wherein $Y^1$, $Y^2$ and $R^4$ are as defined in claim 1.

10. A compound selected from
4-(4-bromo-2-fluorophenylamino)-7-[2-hydroxy-3-(4-methylpiperazin-1-yl)propoxy]-6-methoxy)quinazoline
4-(4-chloro-2-fluorophenylamino)-7-[2-hydroxy-3-(pyrrolidin-1-yl)propoxy]-6-methoxy) quinazoline
4-(4-chloro-2-fluorophenylamino)-7-[2-hydroxy-3-(4-methylpiperazin-1-yl)propoxy]-6-methoxy)quinazoline
4-(4-chloro-2-fluorophenylamino)-7-(2-hydroxy-3-(morpholino)propoxy)-6-methoxy) quinazoline
4-(4-bromo-2-fluorophenylamino)-7-[2-hydroxy-3-(thiazolidin-3-yl)propoxy]-6-methoxy) quinazoline
4-(4-bromo-2-fluorophenylamino)-7-[2-hydroxy-3-(3-pyrrolin-1-yl)propoxy]-6-methoxyquinazoline
4-(4-bromo-2-fluorophenylamino)-7-[2-hydroxy-3-(4-(2-morpholinoethyl)piperazin-1-yl)propoxy]-6-methoxyquinazoline
4-(4-bromo-2-fluorophenylamino)-7-[2-hydroxy-3-(4-(3-hydroxypropyl)piperazin-1-yl)propoxy]-6-methoxyquinazoline
4-(4-bromo-2-fluorophenylamino)-7-[2-hydroxy-3-(4-(2-hydroxyethyl)piperazin-1-yl)propoxy]-6-methoxyquinazoline
4-(4-bromo-2-fluorophenylamino)-7-[2-hydroxy-3-(1,2,3,6-tetrahydropyridin-1-yl)propoxy]-6-methoxyquinazoline
4-(4-bromo-2-fluorophenylamino)-7-[2-hydroxy-3-(N-tertbutyl-N-methylamino)propoxy]-6-methoxyquinazoline
4-(4-bromo-2-fluorophenylamino)-7-[2-hydroxy-3-(N-isopropyl-N-methylamino)propoxy]-6-methoxyquinazoline hydrochloride
4-(4-bromo-2-fluorophenylamino)-7-[2-hydroxy-3-(N-isobutyl-N-methylamino)propoxy]-6-methoxyquinazoline
4-(4-bromo-2-fluorophenylamino)-7-[2-hydroxy-3-(N-(2-hydroxyethyl)-N-methylamino) propoxy]-6-methoxyquinazoline
4-(4-bromo-2-fluorophenylamino)-7-[2-hydroxy-3-(morpholino)propoxy]-6-methoxyquinazoline
4-(4-bromo-2-fluorophenylamino)-7-(2-hydroxy-3-(N,N-dimethylamino)propoxy]-6-methoxyquinazoline
4-(4-bromo-2-fluorophenylamino)-7-[2-hydroxy-3-(piperidin-1-yl)propoxy]-6-methoxyquinazoline
4-(4-bromo-2-fluorophenylamino)-7-[2-hydroxy-3-(pyrrolidin-1-yl)propoxy]-6-methoxyquinazoline
4-(4-chloro-2-fluorophenylamino)-7-[2-hydroxy-3-(N,N,-dimethylamino)propoxy]-6-methoxyquinazoline
4-(4-chloro-2-fluorophenylamino)-7-[2-hydroxy-3-(piperidin-1-yl)propoxy]-6-methoxyquinazoline
4-(4-chloro-2-fluorophenylamino)-7-[2-hydroxy-3-(homopiperidin-1-yl)propoxy]-6-methoxyquinazoline
4-(4-chloro-2-fluorophenylamino)-7-[2-hydroxy-3-(N-(2-hydroxyethyl)-N-methylamino) propoxy]-6-methoxyquinazoline
4-(4-chloro-2-fluorophenylamino)-7-[2-hydroxy-3-(3-pyrrolin-1-yl)propoxy]-6-methoxyquinazoline
4-(4-chloro-2-fluorophenylamino)-7-[2-hydroxy-3-(thiomorpholin-4-yl)propoxy]-6-methoxyquinazoline
4-(4-chloro-2-fluorophenylamino)-7-[2-hydroxy-3-(3-hydroxypyrrolidin-1-yl)propoxy]-6-methoxyquinazoline
4-(4-chloro-2-fluorophenylamino)-7-{2-hydroxy-3-[4-(2-morpholinoethyl)piperazin-1-yl]propoxy}-6-methoxyquinazoline
4-(4-chloro-2-fluorophenylamino)-7-{2-hydroxy-3-[4-(2-hydroxyethyl)]piperazin-1-yl]propoxy}-6-methoxyquinazoline
4-(4-chloro-2-fluorophenylamino)-7-[2-hydroxy-3-(2,5-dimethyl-3-pyrrolin-1-yl)propoxy]-6-methoxyquinazoline
4-(4-chloro-2-fluorophenylamino)-7-[2-hydroxy-3-(4-methylpiperidin-1-yl)propoxy]-6-methoxyquinazoline
4-(4-chloro-2-fluorophenylamino)-7-[2-hydroxy-3-(2-methylpyrrolidin-1-yl)propoxy]-6-methoxyquinazoline
4-(4-chloro-2-fluorophenylamino)-7-[2-hydroxy-3-(N-(2-cyanoethyl)-N-methylamino) propoxy]-6-methoxyquinazoline
4-(4-chloro-2-fluorophenylamino)-7-[2-hydroxy-3-(N-isopropyl-N-methylamino)propoxy]-6-methoxyquinazoline
4-(4-chloro-2-fluorophenylamino)-7-[2-hydroxy-3-(N-isobutyl-N-methylamino)propoxy]-6-methoxyquinazoline
4-chloro-2-fluoro-5-hydroxyphenylamino-7-[2-hydroxy-3-(pyrrolidin-1-yl)propoxy]-6-methoxyquinazoline
4-chloro-2-fluoro-5-hydroxyphenylamino-7-(2-acetoxy-3-piperidinopropoxy)-6-methoxyquinazoline 4-bromo-2-fluoro-5-hydroxyphenylamino-7-[2-acetoxy-3-(pyrrolidin-1-yl)propoxy]-6-methoxyquinazoline
4-bromo-2-fluoro-5-hydroxyphenylamino-7-[2-hydroxy-3-(pyrrolidin-1-yl)propoxy]-6-methoxyquinazoline;
or a salt thereof.

11. A compound according to claim 1 in the form of a pharmaceutically acceptable salt.

12. A process for the preparation of a compound of the formula (I) as defined in claim 1 or a salt thereof which comprises:
(a) the reaction of a compound of the formula III:

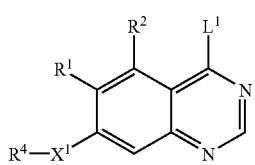

(III)

(wherein $R^1$, $R^2$, $X^1$ and $R^4$ are as defined in claim 1 and $L^1$ is a displaceable moiety), with a compound of the formula IV:

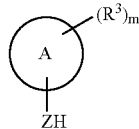

(IV)

(wherein ring A, Z, $R^3$ and m are as defined in claim 1);
(b) where the group of formula IIa:

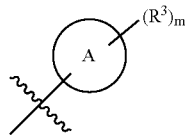

(IIa)

(wherein ring A, $R^3$ and m are as defined in claim 1) is a ring carrying one or more hydroxy groups, the deprotection of a compound of formula V:

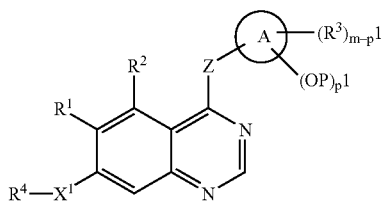

(V)

(wherein ring A, $X^1$, m, $R^1$, $R^2$, $R^3$, $R^4$ and Z are as defined in claim 1, P is a hydroxy protecting group and $p^1$ is an integer from 1 to 5 equal to the number of protected hydroxy groups and such that m-$p^1$ is equal to the number of $R^3$ substituents which are not protected hydroxy);
(c) compounds of formula (I) and salts thereof wherein the substituent $X^1$ is —O—, —S— or —$NR^7$—

(wherein $R^7$ is as defined in claim 1) can be prepared by the reaction of a compound of the formula VI:

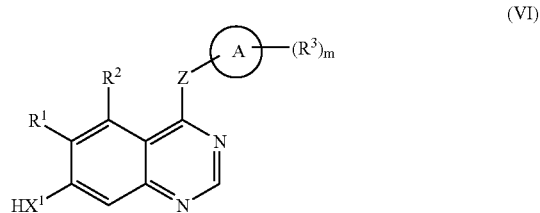

(VI)

(wherein ring A, m, $X^1$, $R^1$, $R^2$, $R^3$, and Z are as defined in claim 1) with a compound of formula VII:

$R^4$-$L^1$ (VII)

(wherein $R^4$ is as defined in claim 1 and $L^1$ is as defined above);
(d) the reaction of a compound of the formula VIII:

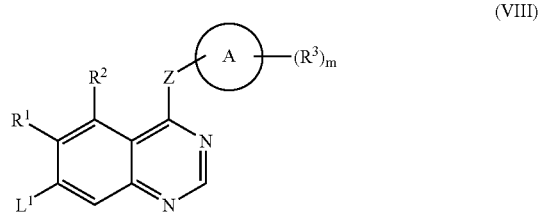

(VIII)

with a compound of the formula IX:

$R^4$—$X^1$—H (IX)

(wherein ring A, $R^1$, $R^2$, $R^3$, $R^4$, Z, m and $X^1$ are all as defined in claim 1 and $L^1$ is as defined above),
e) compounds of the formula (I) and salts thereof wherein $R^4$ is a 2hydroxypropyl chain substituted by —$NR^{17}R^{18}$ (wherein $R^{17}$ and $R^{18}$ are as defined in claim 1) or a saturated or partially saturated heterocyclic ring containing and linked through a ring nitrogen atom and containing up to 2 additional ring heteroatoms selected from O, S and N, can be prepared by reacting a compound of the formula X:

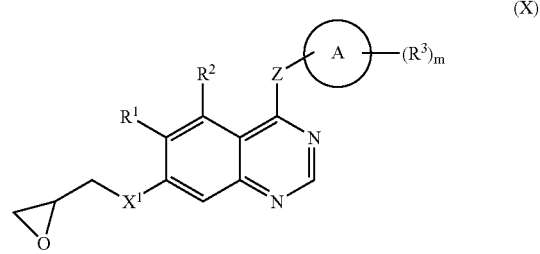

(X)

(wherein ring A, $R^1$, $R^2$, $R^3$, Z, m and $X^1$ are all as defined in claim 1) with the appropriate amine and analagous reactions may be used to produce compounds of the formula (1) wherein $R^4$ comprises longer hydroxy-substituted alkylene, alkenylene or alkynylene chains;
f) compounds of the formula (I) and salts thereof wherein the group in $R^4$ linked to —$Y^1$— or —$Y^2$— is linked via a N, O or S atom may be prepared by reacting a compound of the formula (XI):

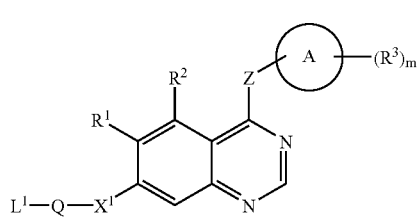

(wherein ring A, $X^1$, $R^1$, $R^2$, $R^3$, Z and m are as defined in claim 1, $L^1$ is as defined above and Q is —$Y^1$— or —$Y^2$— (wherein —$Y^1$— or —$Y^2$— are as defined in claim 1) with the appropriate compound containing a HN, HO or HS group;

and optionally preparing a pharmaceutically acceptable salt of a compound of the formula I reaction of the compound obtained with an acid or base whereby to obtain the desired pharmaceutically acceptable salt.

13. A pharmaceutical composition which comprises a compound of the formula (I) as defined in claims 1–3 and 4–10 or a pharmaceutically acceptable salt thereof, in association with a pharmaceutically acceptable excipient or carrier.

14. A method for producing an antiangiogenic and/or vascular permeability reducing effect in a warm-blooded animal in need of such treatment which comprises administering to said animal an effective amount of a compound of formula (I) as defined in claims 1–3 and 4–10 or a pharmaceutically acceptable salt.

* * * * *